United States Patent
Feuerstein et al.

(10) Patent No.: US 11,085,920 B2
(45) Date of Patent: Aug. 10, 2021

(54) NANODIAMOND PARTICLES AND RELATED DEVICES AND METHODS

(71) Applicant: Debina Diagnostics, Inc., Newtown Square, PA (US)

(72) Inventors: Giora Z. Feuerstein, Bryn Mawr, PA (US); Mark E. Sternberg, Bryn Mawr, PA (US)

(73) Assignee: Debina Diagnostics, Inc., Newtown Square, PA (US)

( * ) Notice: Subject to any disclaimer, the term of this patent is extended or adjusted under 35 U.S.C. 154(b) by 14 days.

(21) Appl. No.: 16/330,950

(22) PCT Filed: Sep. 6, 2017

(86) PCT No.: PCT/US2017/050257
§ 371 (c)(1),
(2) Date: Mar. 6, 2019

(87) PCT Pub. No.: WO2018/048887
PCT Pub. Date: Mar. 15, 2018

(65) Prior Publication Data
US 2019/0212331 A1      Jul. 11, 2019

Related U.S. Application Data

(60) Provisional application No. 62/522,036, filed on Jun. 19, 2017, provisional application No. 62/383,657, filed on Sep. 6, 2016.

(51) Int. Cl.
| | |
|---|---|
| *G01N 33/558* | (2006.01) |
| *G01N 33/543* | (2006.01) |
| *G01N 33/533* | (2006.01) |
| *G01N 21/64* | (2006.01) |
| *G01N 33/58* | (2006.01) |

(52) U.S. Cl.
CPC .......... *G01N 33/533* (2013.01); *G01N 21/64* (2013.01); *G01N 21/6428* (2013.01); *G01N 33/54346* (2013.01); *G01N 33/558* (2013.01); *G01N 33/587* (2013.01); *G01N 2800/226* (2013.01)

(58) Field of Classification Search
CPC .... G01N 33/533; G01N 21/64; G01N 33/587; G01N 21/6428; G01N 33/54346; G01N 33/558; G01N 2800/226; G01N 21/6458; G01N 2201/0221; G01N 21/6489; A61K 49/0056; A61K 49/0065; B01L 2300/0816
See application file for complete search history.

(56) References Cited

U.S. PATENT DOCUMENTS

| | | | |
|---|---|---|---|
| 5,380,646 A | 1/1995 | Knight et al. | |
| 7,993,216 B2 | 8/2011 | Lee | |
| 9,465,035 B2 | 10/2016 | Shirakawa et al. | |
| 2008/0102036 A1 | 5/2008 | Poss et al. | |
| 2008/0188413 A1 | 8/2008 | Chuang et al. | |
| 2010/0055089 A1 | 3/2010 | Varner et al. | |
| 2013/0177528 A1 | 7/2013 | Markland et al. | |
| 2013/0196347 A1 | 8/2013 | Turkcan et al. | |
| 2013/0303960 A1* | 11/2013 | Courtney | C07K 16/2812 604/5.02 |
| 2014/0017812 A1* | 1/2014 | Smith | G01N 33/558 436/501 |
| 2015/0010900 A1 | 1/2015 | Eshoo et al. | |
| 2015/0147276 A1 | 5/2015 | Ingber et al. | |

FOREIGN PATENT DOCUMENTS

| | | |
|---|---|---|
| JP | 2009-119561 A | 6/2009 |
| JP | 2012-206863 A | 10/2012 |
| WO | WO 1994/009036 A1 | 4/1994 |
| WO | WO 2014/121819 A1 | 8/2014 |
| WO | WO 2015/038967 A1 | 3/2015 |

(Continued)

OTHER PUBLICATIONS

Zhang et al. ("Nanostructuring of Biosensing Electrodes with Nanodiamonds for Antibody Immobilization", ACSNano, vol. 8(2), pp. 1419-1428, published Jan. 7, 2014). (Year: 2014).*

(Continued)

*Primary Examiner* — Tracy Vivlemore
*Assistant Examiner* — Nam P Nguyen
(74) *Attorney, Agent, or Firm* — Wolf, Greenfield & Sacks, P.C.

(57) ABSTRACT

Nanodiamond particles and related devices and methods, such as nanodiamond particles for the detection and/or quantification of analytes, are generally described. In some embodiments, the device comprises a plurality of nanodiamond particles and a species bound to the nanodiamond particles. In certain embodiments, the plurality of nanodiamond particles may be exposed to a sample suspected of containing an analyte. In some cases, the analyte may bind to the species such that the presence of the analyte in the sample may be detected. In some embodiments, the devices, systems, and methods described herein are useful for the detection of an analyte in a sample obtained from a subject for, for example, diagnostic purposes. In some cases, the systems, devices, and methods described herein may be useful for diagnosing, prevent, treating, and/or managing a disease or bodily condition. In an exemplary embodiment, such systems, devices, and methods described herein may be useful for detecting and/or quantifying the presence of a virus (e.g., ebola) in a subject and/or a sample obtained from the subject.

11 Claims, 34 Drawing Sheets

(56) References Cited

FOREIGN PATENT DOCUMENTS

WO  WO 2015/087334 A1  6/2015
WO  WO 2018/048477 A1  3/2018

OTHER PUBLICATIONS

International Search Report and Written Opinion for PCT/US2017/050257 dated Nov. 7, 2017.
International Search Report and Written Opinion for PCT/US2017/025742 dated Jun. 15, 2017.
Baidoo et al., Design and Synthesis of a Short-Chain Bitistatin Analogue for Imaging Thrombi and Emboli. Bioconjugate Chem. 2004;16:1068-75. Epub Aug. 28, 2004.
Carbajo et al., NMR structure of bitistatin—a missing piece in the evolutionary pathway of snake venom disintegrins. FEBS Journal. 2015;282:341-60.
Juliano et al., Disintegrin Interaction with $\alpha_v\beta_3$ Integrin on Human Umbilical Vein Endothelial Cells: Expression of Ligand-Induced Binding Site on $\beta_3$ Subunit. Experimental Cell Research. 1996;225:132-42.
Knight et al., Imaging Pulmonary Emboli and Deep Venous Thrombi with $^{99m}$Tc-Bitistatin, a Platelet-Binding Polypeptide from Viper Venom. The Journal of Nuclear Medicine. Jun. 2000;41(6):1056-64.
Knight et al., In Vitro Platelet Binding Compared with In Vivo Thrombus Imaging Using $\alpha_{IIb}\beta_3$-Targeted Radioligands. Thromb Haemost. 1998;80(05):845-51.
Knight et al., Platelet binding and biodistribution of [$^{99m}$Tc]rBitistatin in animal species and humans. Nuclear Medicine and Biology. 2007;34:855-63.
Knight et al., Functional expression of bitistatin, a disintegrin with potential use in molecular imaging of thromboembolic disease. Protein Expression and Purification. 2005;39:307-19. Epub Dec. 8, 2004.
Marcinkiewicz et al., EC3, a Novel Heterodimeric Disintegrin from Echis carinatus Venom, Inhibits $\alpha 4$ and $\alpha 5$ Integrins in an RGD-independent Manner. Journal of Biological Chemistry. Apr. 1999;274:12468-73.
Mark et al., Microfluidic lab-on-a-chip platforms: requirements, characteristics and applications. Chemical Society Reviews. 2010;39:1153-82. Epub Jan. 25, 2010.
Shebuski et al., Characterization and platelet inhibitory activity of bitistatin, a potent arginine-glycine-aspartic acid-containing peptide from the venom of the viper *Bitis arietans*. Journal of Biological Chemistry. Dec. 1989;264:21550-6.
Swanson et al., Lateral Flow Assay with Near-Infrared Dye for Multiplex Detection. Clinical Chemistry. 2013;59(4):641-8.
Ivukina et al., Fluorescent nanodiamond bioconjugates on the base of barnase:barstar module. Dokl Biochem Biophys. Sep.-Oct. 2011;440:231-3. doi: 10.1134/S1607672911050115. Epub Nov. 19, 2011.
Knight et al., Preliminary evaluation of labeled disintegrins (snake venom peptides) for thrombus imaging. J Nucl Chem. Jun. 1993;34(5):66P.
Say et al., Luminescent nanodiamonds for biomedical applications. Biophys Rev. Dec. 2011;3(4):171-184. doi: 10.1007/s12551-011-0056-5. Epub Oct. 11, 2011. Review.
Weng et al., Fluorescent nanodiamonds for specifically targeted bioimaging: Application to the interaction of transferrin with transferrin receptor. Diam Rel Mat. Feb. 2009;18(2-3):587-591. Doi: 10.1016/j.diamond.2008.07.012.
Opitz et al., Green flourescent nanodiamond conjugates and their possible applications for biosensing. Proc of SPIE. 2010;7759:775914.1-8.

* cited by examiner

F-NDP-Bt          PBS

Aggregation: Dose Response Curves

FLOW CYTOMETRY DOT PLOTS

FLOW CYTOMETRY DOT PLOTS ns and Methods, each of 15
NANODIAMOND PARTICLES AND RELATED DEVICES AND METHODS

RELATED APPLICATIONS

This application is a national stage filing under 35 U.S.C. § 371 of international application number PCT/US2017/050257, filed Sep. 6, 2017, which claims priority under 35 U.S.C. § 119(e) to U.S. Provisional Application No. 62/383,657, filed Sep. 6, 2016, and entitled "Engineering And Utility Of Fluorescent Nanodiamond Particles (F-NDP) For Diagnostics And Treatment Of Blood Clots In Human And Veterinary Medicine," and to U.S. Provisional Application No. 62/522,036, filed Jun. 19, 2017, and entitled "Nanodiamond Particles And Related Devices And Methods," each of which is incorporated herein by reference in its entirety for all purposes.

TECHNICAL FIELD

Nanodiamond particles and related devices and methods, such as nanodiamond particles for the detection and/or quantification of analytes, are generally described. In addition, the present invention relates to the field of medical and veterinary diagnostics and treatment. More specifically, the invention relates to a diagnostic reagent, tool, and system that are specific for detection of platelets and blood clots. In addition, the invention relates to detection of internal body bleeding sites in a variety of diseases and trauma conditions.

BACKGROUND

Cardiovascular diseases, such as stroke and heart attack, are the leading cause of mortality in developed countries. Deaths from strokes and heart attacks are predominantly the consequence of blood clots (thrombi) formed in the cerebral and cardiac vessels or thrombo-embolic events (TEE) associated with blood clots formed in remote vessels (e.g., peripheral venous system, cardiac atria appendixes). While several factors are well known to contribute to a fatal TEE (e.g., atherosclerosis vascular disease) there is a clear "diagnostic and prognostic gap" in the assessment of the specific and "total clot burden" in individuals that carry known risk factors (e.g., atherosclerotic vascular disease), let alone factors not yet fully vetted as predictive of TEE. Invariably, clinical presentation of consequences of blood flow occlusion by thrombi leading to stroke or heart attack command prompt medical investigations in search for the TEE culprits. Such investigations are mostly hospital-based imaging tests, such as angiography, CAT scans, MRI, and ultrasound. The current technologies are important for timely and successful management of strokes and heart attacks, yet several important limiting factors must be addressed. First, the general population, especially elderly people who carry cardiovascular risks, often have limited access to hospital-based technologies to assess blood clots in vessels. Second, even in hospitals, access to these imaging technologies has a certain time requirement associated with the tests and their evaluation by specialists. In the case of a stroke, where the treatment window is limited to three to four and a half hours after the onset of the event, much of the time is spent in establishing patient eligibility for thrombolysis treatment, often to the extent of missing the critical window for treatment.

On the other extreme, once a diagnosis of cardiac arrhythmia, such as atrial fibrillation (chronic, relapsing) is made, the risk of TEE mandates lifelong treatment with anticoagulants even though the presence of clots in the cardiac chambers (appendixes) is unknown. These few examples point to a major "diagnostic gap" of TEE risks, which due to lack of early diagnosis and preventative measures often results in fatal outcomes. Early assessment of whole body clot burden or TEE risk, in ambulatory settings, that allows easy and broad access and affordable cost, is needed.

Furthermore, immunochromographic assays, such as lateral flow assays, are generally used to detect the presence or absence of an analyte such as an antigen in a sample. However, such assays generally lack automated processing, accurate quantification methods, and may, in some cases, require subjective interpretation, leading to false positives and/or false negatives.

Accordingly, improved devices and methods are needed.

SUMMARY

Nanodiamond particles and related devices and methods, such as nanodiamond particles (e.g., fluorescent nanodiamond particles) for the detection and/or quantification of analytes, are generally described. The subject matter of the present invention involves, in some cases, interrelated products, alternative solutions to a particular problem, and/or a plurality of different uses of one or more systems and/or articles.

In one aspect, diagnostic agents are provided. In some embodiments, the diagnostic agents comprise a fluorescent nanodiamond particle chemically bonded to a polypeptide and/or polynucleotide.

In another aspect, fluidic devices are provided. In some embodiments, the fluidic device comprises a sample inlet, a reservoir in fluidic communication with the sample inlet, the reservoir comprising a plurality of fluorescent nanodiamond particles, a plurality of a first species bound to the plurality of fluorescent nanodiamond particles, a detection region in fluidic communication with the reservoir, the detection region comprising a plurality of a second species bound to the detection region, and a control region in fluidic communication with the detection region, the control region comprising a plurality of a third species bound to the control region.

In yet another aspect, systems are provided. In some embodiments, the system comprises a sample inlet, a reservoir in fluidic communication with the sample inlet, the reservoir comprising a plurality of fluorescent nanodiamond particles, a plurality of a first species bound to the plurality of fluorescent nanodiamond particles, a detection region in fluidic communication with the reservoir, the detection region comprising a plurality of a second species bound to the detection region and a detector configured to quantify a fluorescent emission at the detection region.

In some embodiments, the system comprises a sample inlet, a reservoir in fluidic communication with the sample inlet, the reservoir comprising a plurality of fluorescent nanodiamond particles, a plurality of a first species bound to the plurality of fluorescent nanodiamond particles, a detection region in fluidic communication with the reservoir, the detection region comprising a plurality of a second species bound to the detection region and a detector configured to quantify an infrared signal at the detection region.

In yet another aspect, methods are provided. In some embodiments, the method comprises introducing, into a fluidic channel of a fluidic device, a sample suspected of containing an analyte, exposing the sample to a species bound to a plurality of fluorescent nanodiamond particles such that the analyte, if present, binds to at least a portion of the species bound to the plurality of fluorescent nanodiamond particles, removing any fluorescent nanodiamond particles and species not bound to the analyte, and quantifying a fluorescence emission of the plurality of fluorescent nanodiamond particles bound to the analyte.

In some embodiments, the method comprises administering, to a subject (e.g., a human, a mammal) suspected of having a particular analyte, a plurality of fluorescent nanodiamond particles bound to a species such that the species may bind to the analyte, if present, and detecting a fluorescent emission of the plurality of fluorescent nanodiamond particles comprising the species bound to, if present, the analyte.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 15A shows an in situ carotid bifurcation region image indicating fluorescence of a carotid arterial clot after treatment visible via IVIS imaging after exposure of the carotid bifurcation zone. FIGS. 15B and 15C are high magnification images of fluorescence emanating from the carotid bifurcation in vivo suggesting accumulation of FNDP in the clot. FIG. 15D shows ex vivo fluorescence of carotid artery bifurcation denoting one branch that shows fluorescence corresponding to the clot location within the carotid bifurcation. FIGS. 15E and 15F show confocal images taken on an Olympus IX83, showing that FNDP fluorescence is detected at an excitation of 543 nm and an emission of 655-755 nm.

FIG. 16A shows an ex vivo fluorescent image of a carotid artery from saline-treated control. FIG. 16B shows an ex vivo fluorescent image of a carotid artery from an IV FNDP-treated animal showing fluorescence localized to the branch with clot. FIGS. 16C-F show confocal images taken on an Olympus IX83. FIG. 16G is a graph showing the number of FNDPs present in carotid clot lysates from animals treated locally via the external carotid artery or intravenously as compared with saline treated controls.

FIG. 17A shows images of plasma clots obtained from fluorescence microscope Olympus IX81 analysis, under 100× magnification. FIG. 17B shows images of plasma clots obtained in an IVIS 50 imaging system. Wavelengths used for measurement: excitation Cy5.5 BkG (580-610 nm), emission Cy5.5 (695-770 nm). For background subtraction: excitation GFP (445-490 nm), emission Cy5.5 (695-770 nm). Exposure time: 1 minute. Arrows point the localization of the clot.

FIG. 18A shows an image of the implanted glass capillaries filled with F-NDP-Bt (4 mg/ml) or PBS (control). Exposure time was 5 seconds. FIG. 18B shows an image of a rat aorta filled with F-NDP-Bt. The rat aorta was dissected from a euthanized female rat, washed with PBS to remove residues of coagulated blood, and filled with 300 µl of F-NDP-Bt suspension (2 mg/ml) in PBS.

FIG. 20A shows the percentage of all platelets, FIG. 20B shows the percentage of CD62 +ve platelets, and FIG. 20C shows the percentage of GPIIb/IIIa +ve platelets bound to the 700 nm and 200 nm probes at various concentrations. Data shown are the mean (+), the line within the box represents the median, upper and lower edges of the box represents $75^{th}$ and $25^{th}$ percentiles, and upper and lower whiskers represent the $95^{th}$ and $5^{th}$ percentiles.

(FIG. 26A) F-NDP suspensions were scanned for fluorescence in a fluorescence plate reader for a range of excitation and emissions. The fluorescence is normalized by subtracting a blank well and log 10 processed. (FIG. 26B) Capillaries were filled with indicated density of F-NDP in PBS and analyzed by IVIS imaging using 5 seconds exposure. Insert indicates representative images of capillaries. Average fluorescence is presented in the plot. (FIG. 26C) Comparison of fluorescence intensity for different concentrations of F-NDP(NV) as function of exposure time. Error bars represent SD for three to five independent experiments. *Difference between F-NDP(NV) and F-NDP(NVN) (P<0.01)

(FIG. 28A) Capillaries filled with F-NDP (NV) (4 mg/ml), F-NDP(NVN) (4 mg/ml), or PBS were positioned under abdominal skin patch of euthanized rat. Positions of capillaries are indicated by arrows. (FIG. 28B) Capillary filled with F-NDP(NV) (4 mg/ml) covered by rat quadriceps muscles ranged from 2 mm (flanking) to 5.9 mm (in the center). (FIG. 28C) Capillaries filled with F-NDP (4 mg/ml) or PBS were inserted into porcine axillary vein. (FIG. 28D) Capillaries filled with F-NDP (4 mg/ml) or PBS were covered with porcine skin (2.5 mm) free of subdermis (FIG. 28E) Intensity of fluorescence for different concentrations of F-NDP(NV) through 2.5 mm porcine skin free of subdermis. (FIG. 28F) Porcine axillary veins filled with F-NDP(NV) (2 mg/ml) or PBS and covered with 8 mm porcine skin including dermis and subdermis. (FIG. 28G) Capillaries filled with F-NDP(NV) (20 mg/ml), F-NDP (NVN) (20 mg/ml) and PBS (same volume) covered with porcine skin containing increased thickness of adipose tissue (presented on the insert). (FIG. 28H) Representative ultrasound of human carotid artery showing the artery 11.89 mm below the surface.

(FIGS. 29A-29F) Images of fluorescence recorded by an IVIS scanner designed for whole animal imaging using a 580-610 nm excitation and a 695-770 nm emission passband with 2 second exposure. Auto-fluorescence was subtracted based on excitation at 445-490 nm (FIG. 29A, FIG. 29B) In situ fluorescence imaging of carotid arterial clot after treatment in duplicate animals by IVIS (separation of neck particle by dissection) Scale bar=1 cm. (FIGS. 29C-29F) Ex-vivo fluorescence of isolated carotid artery after F-NDP(NV)-Bit treatment (FIG. 29C, FIG. 29D) or with vehicle control of saline (FIG. 29E, FIG. 29F). Scale bar=1 mm. (FIGS. 29G-29J) Confocal image stacks were taken on Olympus FV 1000. F-NDP(NV)-Bit fluorescence was detected at an excitation of 543 nm and an emission of 655-755 nm. Background fluorescence was collected from the same excitation, with emissions of 555-625 nm and was subtracted from the foreground. Scale bar=1 mm. Fluorescence of carotid artery after F-NDP(NV)-Bit treatment (FIG. 29G, FIG. 29H) or with saline treatment (FIG. 29I, FIG. 29J). (FIG. 29K) In situ images of a FeCl3—generated clot carotid artery compared with untreated contralateral artery. (FIGS. 29L-29N) Clots dissolved with RIPA lysis buffer and replicates are combined together to form a lysate. Aliquots of the lysate was then deposited onto a cover glass (10 μL) and imaged with 20× objective. Scale bar=100 □m. (FIG. 29K) Large numbers of F-NDP(NV)-Bit are visible. (FIG. 29L) After IV treatment at low dose (1 mg), F-NDP(NV)-Bit are found in the lysate at the site of clot formation. (FIG. 29N) Almost no fluorescent particles are detected in saline control.

(FIGS. 30A-30J) images of fluorescence are performed on an IVIS scanner designed whole animal imaging using a 580-610 nm excitation and a 695-770 nm emission passband with 2 second exposure. Autofluorsesence was subtracted based on excitation at 445-490 nm. (FIGS. 30A-30C) Gross image indicating fluorescence of carotid arterial clot after treatment in triplicate animals is visible via IVIS imaging after exposure of artery. Scale bar=1 cm. (FIGS. 30D-30I) Ex-vivo fluorescence of carotid artery after F-NDP(NV)-Bit treatment (FIGS. 30D-30F) or with saline treatment (FIGS. 30G-30I) Scale bar=1 mm. (FIGS. 30J-30O) Confocal image stacks taken on Olympus FV 1000. F-NDP(NV)-Bit fluorescence is detected at an excitation of 543 nm and an emission of 655-755 nm. Scale bar=1 mm. Fluorescence of carotid artery after F-NDP(NV)-Bit treatment (FIGS. 30J-30L) or with saline treatment (FIGS. 30M-30O). (FIG. 30P) Lysates from solubilized carotid arteries are imaged and F-NDP(NV)-Bit are counted by hemocytometer. Contralateral untreated control is presented in insert. Scale bar=100 μm (FIG. 30Q) Total number of F-NDP(NV)-Bit detected per carotid bifurcation in the clotted side compared with the contralateral control as counted by hemocytometer. (FIG. 30R, FIG. 30S) Brightness after subtraction of background via IVIS (FIGS. 30D-30I) and LSCM (FIGS. 30J-30O) imaging of treated and contralateral untreated carotid bifurcations. Error bars represent standard deviation. *=p<0.05, **=p<0.01 vs control by t-test.

DETAILED DESCRIPTION

Figure 1A:
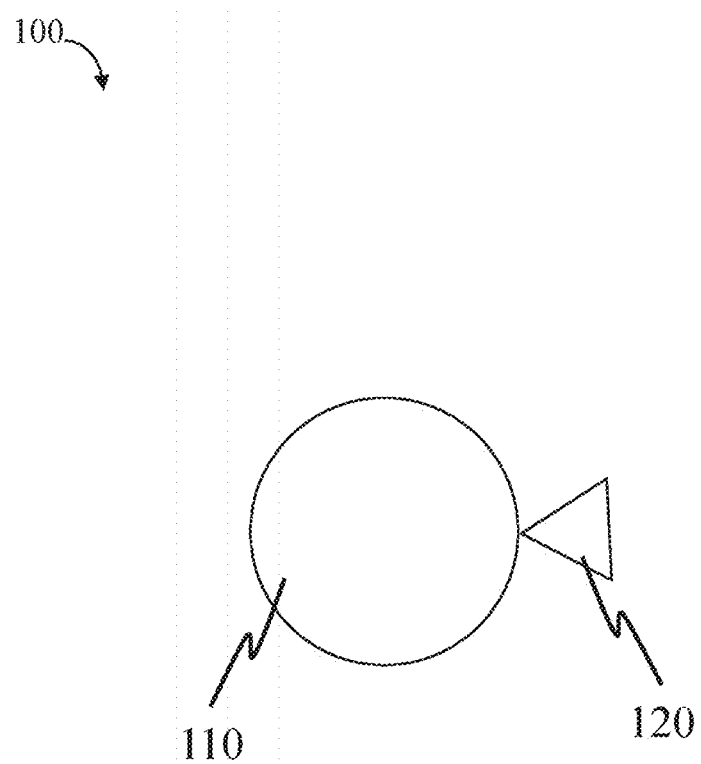
FIG. 1A is a schematic illustration of a system including fluorescent nanodiamond particles, according to one set of embodiments.

Nanodiamond particles and related devices and methods, such as nanodiamond particles for the detection and/or quantification of analytes, are generally described. In some embodiments, the present invention provides diagnostic agents and methods for risk assessment of subjects, including both humans and non-human animals at risk of thromboembolic events (TEE), which are the main cause of cardiovascular death from strokes and heart attacks. The diagnostic agents and methods of the invention enable assessment of the total body burden of intravascular clots and detection of nascent thrombi at common predilection sites for clot formation using non-radiation (e.g., X-ray), non-MRI, and non-ultrasound techniques. The technology generally comprises a non-invasive, telemetry-based fluorescent recording system suitable for use in a fast and affordable ambulatory setting. The invention includes multiple innovative scientific and engineering breakthroughs.

The invention is based, at least in part, on the recognition that fluorescent nano-diamond particles (NDP-F) functionalized with a species (e.g., a polypeptide such as the disintegrin Bitistatin (Bt), immunoglobulins such as IgG, and/or bovine serum albumin (BSA)) may have the innate ability to bind e.g., avidly to activated platelet fibrinogen receptors (PFR). For example, data presented herein demonstrate successful coupling of Bt to NDP-F and retention of Bt bioactivity. The methods, reagents, and de novo protocols used to accomplish the invention are not known to the inventors as having been reported by others before.

In some embodiments, the device comprises a plurality of nanodiamond particles and a species (e.g., a polypeptide, a polynucleotide) bound to the nanodiamond particles. In certain embodiments, the plurality of nanodiamond particles may be exposed to a sample suspected of containing an analyte. In some cases, the analyte may bind to the species such that the presence of the analyte in the sample may be detected. In some embodiments, the devices, systems, and methods described herein are useful for the detection of an analyte in a sample obtained from a subject for, for example, diagnostic purposes. In some cases, the systems, devices, and methods described herein may be useful for diagnosing, prevent, treating, and/or managing a disease or bodily condition. In an exemplary embodiment, such systems, devices, and methods described herein may be useful for detecting and/or quantifying the presence of a virus (e.g., ebola) in a subject and/or a sample obtained from the subject.

Advantageously, as compared to traditional systems for quantifying analytes (e.g., viruses, bacteria, toxins, environmental pollutants, etc.) in a sample from a subject, the systems and methods described herein may comprise quantification of the amount of analyte present in the sample.

The present invention may also enable broad scale survey of TEE risks that may be applicable in many medical emergency and life-threatening conditions beyond strokes and heart attacks. The technology not only can be used for individuals suspected to be at risk for TEE but also can be periodically deployed as part of primary health care office assessments, no different than annual mammography, lipids tests, or physical examinations. For example, in some embodiments, the present invention monitors fluorescent light emittance and is expected to be highly affordable, minimally invasive (requiring only a single injection of a safe dose of nanoparticles), and can be conducted and interpreted in an ambulatory setting by a trained emergency medical technician or a primary care physician, similar to ECG monitoring.

One general aspect of the invention is an imaging agent for detection of a thrombus in a subject. The agent is composed, in an exemplary embodiment, of three elements, as follows: i) a fluorescent nano-diamond particle (NDP-F); ii) a ligand that functionalizes the NDP-F, such as a —COOH, —OH, —NH$_2$, or —C=O moiety; and iii) a protein attached to the ligand. The three can be bonded together in any order and by any type of chemical bonds, but are typically covalently bonded in the order described. The objective of the imaging agent is to specifically bind the agent to a discrete biological target in a human or non-human animal body.

Yet another aspect of the invention is a diagnostic method for detection of activated platelets. In some cases, the diagnostic method is based in large part on the ability of a species such as a polypeptide (e.g., bitistatin, BSA, human IgG) to bind to a specific antigen (e.g., PFR) with high affinity and/or avidity. In some embodiments, the polypeptide (e.g., bitistatin) is configured to target the NDP-F to e.g., activated platelets, and thus sites of thrombus formation. In some embodiments, the fluorescence of the NDP-F allows non-invasive and relatively harmless imaging of the location and size of the thrombus, or multiple thrombi. In certain embodiments, the diagnostic method is qualitative, and in other embodiments it is semi-quantitative or quantitative. In some embodiments, the method comprises: i) administering to a subject suspected of having, or potentially having, one or more sites of thrombus, a detectable amount of the diagnostic agent of the invention, ii) allowing sufficient time for the diagnostic agent to localize to the site(s) of thrombus, and iii) detecting the diagnostic agent by detecting fluorescence emission after excitation with a suitable electromagnetic stimulus (e.g., excitation light, such as emission from a hand held device). It is to be understood that, in some embodiments, in step iii) the act of excitation can be omitted if the fluorescent tag is intrinsically fluorescent in the subject's body. The step of administering can be any action that results in introduction of the imaging agent into the systemic blood stream of the subject. It thus may be, for example and without limitation, via intravenous injection or infusion.

Yet further, and in accordance with the method described immediately above, the invention includes a method of detecting clots or clot formation in subjects. As with the method described above, this method can be considered a method of detecting or imaging clots, clot formation, platelet activation, or pathological zones that form a risk for clot formation, such as an atherosclerotic vascular plaque or inflammation. The method steps are those described above. For example, in some embodiments, a clot in a subject may be detected by administering a plurality of nanodiamond particles functionalized with a species (e.g., a polypeptide such as bitistatin) which may bind to at least a portion of a clot.

As those of skill in the art will immediately recognize, the diagnostic and imaging methods of the present invention, by virtue of introduction of a non-natural bio-active substance into a subject's body, do not relate solely to collection of data regarding a biological event, but instead relate to physical and physiological changes to the subject's body. For example, introduction of the non-naturally occurring imaging agent into the blood stream of a subject physically alters the make-up of the blood stream. In addition, binding of the imaging agent to activated platelets alters the body's natural ability to interact with the activated platelets, and thus the clotting cascade. Other physical and physiological changes upon administration of the imaging agent of the invention will be apparent to the skilled artisan.

The present invention also encompasses kits for practicing the methods of the invention. Broadly speaking, a kit according to the invention includes the imaging agent of the invention in packaged form suitable for distribution, delivery, and/or storage for use in a method of the invention. In customary fashion, the package is made of a suitable material, such as, but not limited to, a cardboard or plastic box and the like, a metal container and the like, or a foil pouch or the like. In some embodiments, the kit includes sufficient imaging agent in a container for a single administration, whereas in other embodiments, the kit includes sufficient imaging agent for two or more administrations. In embodiments where the kit includes sufficient imaging agent for two or more administrations, the imaging agent can be supplied in a single container for multiple uses or in two or more containers, each containing sufficient imaging agent for a single use. In some cases, a combination of single-use and multiple-use containers can be included in a kit. In certain embodiments, the kit (regardless of how many containers of imaging agent are provided in the kit) can be provided in packaged combination with one or more reagents or devices for administration of the imaging agent to a subject. As such, and without limitation, a kit of the invention can include, in packaged combination, the imaging agent with an antiseptic (e.g., ethanol swabs or pads or iodine swabs or pads), one or more syringes, one or more needles adapted to connect with a syringe, and/or one or more pieces of gauze and/or adhesive to facilitate closure and healing of the site of administration.

In some embodiments, a plurality of nanodiamond particles (e.g., NDP-F) bound to a species such as a polypeptide or polynucleotide may be introduced into a sample suspected of containing an analyte. In certain embodiments, the polypeptide and/or polynucleotide may be selected such that, if present, the polypeptide and/or polynucleotide binds to the analyte.

In some embodiment, if an analyte is present in the sample, the analyte, the species, and/or the nanodiamond particle may bind such that the presence of the analyte may be detected. In some cases, the detection of the analyte comprises quantification of an emission (e.g., a fluorescent emission, a near infrared emission) by the nanodiamond particle. In some embodiments, quantification of the emission comprises quantification of a relative intensity and/or quantification of a wavelength of the emission. Without wishing to be bound by theory, in some cases, the intensity of the emission may be proportional (e.g., directly proportional, exponentially proportional, logarithmically proportional) to the amount of analyte present in the sample.

In some embodiments, the plurality of (fluorescent) nanodiamond particles are administered to a subject. In certain embodiments, the plurality of nanodiamond particles may be administered orally, rectally, vaginally, nasally, or uretherally to the subject. In some cases, the plurality of nanodiamond particles are administered surgically (e.g., implanted) and/or injected (e.g., into the systemic circulation, intraoccularly, into the spinal system, e.g., via syringe).

In another exemplary embodiment, the plurality of nanodiamond particles (e.g., the plurality of nanodiamond particles comprising a species bound to the nanodiamond particles) may be administered to a subject (e.g., for the detection of an analyte suspected of being present in the subject). For example, in some cases, the plurality of nanodiamond particles comprising the species may be administered to the subject and, upon detection of an emission (e.g., fluorescent emission, near infrared emission) of the nanodiamond particles, demonstrate the presence of an analyte in the subject. In some cases, the analyte may be at least a portion of a (blood) clot capable of binding to the nanodiamond particles. In some embodiments, a detection device configured to measure and/or detect a fluorescent emission and/or a near infrared emission may be applied to the subject (e.g., on or near the skin, at a location internal of the subject) such that, if the analyte is present, the emission is detected and/or quantified.

As described above, the methods, devices, and systems described herein may be useful for determining and/or quantifying the amount of analyte present in a sample. In some embodiments, the sample is a fluid. In certain embodiments, the sample is whole blood. In certain embodiments, the sample is obtained from a subject such as whole blood, plasma, urine, sputum, sweat, and/or other biological fluids. Methods for collecting such samples are known in the art. In some embodiments, the sample is introduced into a fluidic device (e.g., a fluidic device comprising a reservoir comprising a plurality of nanodiamond particles).

In certain embodiments, the sample may be diluted (e.g., prior to determining and/or quantifying the amount of analyte present in the sample). For example, in certain embodiments, a buffer solution may be added to the fluidic device comprising the plurality of nanodiamond particles before, during, and/or after introducing the sample to the fluidic device such that the sample is diluted. In some embodiments, the buffer solution is contained within a reservoir in fluidic communication with one or more components of the fluidic device. The sample may be diluted in a buffer solution prior to, or during, the introduction of the plurality of nanodiamond particles to the sample. In some embodiments, an analyte in a sample is readily determinable without any subsequent process steps. In some cases, the analyte is present in a subject and the nanodiamond particles may be administered to the subject, as described above.

The term 'nanodiamond particle' generally refers to a diamond particle having an average cross-sectional dimension of less than 1 micrometer (e.g., less than or equal to 900 nanometers, less than or equal to 800 nanometers, less than or equal to 700 nanometers, less than or equal to 600 nanometers, less than or equal to 500 nanometers, less than or equal to 400 nanometers, less than or equal to 300 nanometers, less than or equal to 200 nanometers, less than or equal to 100 nanometers, less than or equal to 90 nanometers, less than or equal to 80 nanometers, less than or equal to 70 nanometers, less than or equal to 60 nanometers, less than or equal to 50 nanometers, less than or equal to 40 nanometers, less than or equal to 30 nanometers, less than or equal to 20 nanometers, or less than or equal to 10 nanometers). In some cases, the nanodiamond particle may have an average cross-sectional dimension of greater than or equal to 5 nanometers, greater than or equal to 10 nanometers, greater than or equal to 20 nanometers, greater than or equal to 30 nanometers, greater than or equal to 40 nanometers, greater than or equal to 50 nanometers, greater than or equal to 60 nanometers, greater than or equal to 70 nanometers, greater than or equal to 80 nanometers, greater than or equal to 90 nanometers, greater than or equal to 100 nanometers, greater than or equal to 200 nanometers, greater than or equal to 300 nanometers, greater than or equal to 400 nanometers, greater than or equal to 500 nanometers, greater than or equal to 600 nanometers, greater than or equal to 700 nanometers, greater than or equal to 800 nanometers, or greater than or equal to 900 nanometers. Combinations of the above-referenced ranges are also possible (e.g., less than 1 micrometer and greater than or equal to 5 nanometers, less than or equal to 700 nanometers and greater than or equal to 100 nanometers). Other ranges are also possible. Those of ordinary skill in the art would be capable of selecting suitable methods for determining the average cross-sectional dimension of a nanodiamond based upon the teachings of this specification.

Without wishing to be bound by theory, in some cases, the nanodiamond particles described herein may be auto-fluorescent (e.g., the nanodiamond particles emit fluorescent light e.g., after absorption of electromagnetic radiation). In some cases, the nanodiamond particles may comprise one or more atomistic-type defects (e.g., a point defect such as a nitrogen-vacancy (NV) center, a point defect such as a nitrogen-vacancy-nitrogen (NVN) defect, combinations thereof) which result in near-infrared fluorescence and/or photoluminescence that may be detected and/or quantified. Other defects are also possible (e.g., Si-vacancy defects). In certain embodiments, the nanodiamond particles fluoresce in response to an applied electromagnetic radiation.

For example, in some embodiments, the nanodiamond particle may be excited (e.g., by applying electromagnetic radiation having a first wavelength) such that the nanodiamond particle emits a detectable emission (e.g., an electromagnetic radiation having a second wavelength, different than the first wavelength). In a particular set of embodiments, if an analyte is present in a sample, the analyte binds to the nanodiamond particle (e.g., binds to a species bound to the nanodiamond particle) such that an emission from the nanodiamond particle may be detected and/or quantified. In some cases, detection of an emission of nanodiamond particles in a subject may indicate that the nanodiamond particles are bound to the suspected analyte. In some such cases, the emission may be quantified (e.g., to determine the relative amount of analyte present in the subject).

In another set of embodiments, the sample suspected of containing the analyte may be added to a fluidic device such that, if present, the analyte binds to the nanodiamond particles (e.g., to the species bound to the nanodiamond particles) and to a detection region in the fluidic device. In some such embodiments, the presence of an emission indicates the presence of the analyte in the sample. In some cases, the intensity and/or wavelength of the emission may be quantified.

As described herein, in some embodiments, the systems, devices, and methods comprise a plurality of nanodiamond particles and a species bound to the plurality of nanodiamond particles. Advantageously, the devices and methods described herein may, in some embodiments, permit the analysis of analytes from whole blood without additional filtering or separation steps and/or have relatively high sensitivity as compared to certain existing analyte quantification methods.

As illustrated in FIG. 1A, in some embodiments, device 100 comprises a plurality of nanodiamond particles 110 associated with a species 120 (e.g., a species which may bind to an analyte, if present). In some embodiments, the nanodiamond particles are associated with (e.g., bound to) the species via functionalization of the nanodiamond particle. For example, in some embodiments, a nanodiamond particle is associated with a species via formation of a bond, such as an ionic bond, a covalent bond, a hydrogen bond, Van der Waals interactions, and the like. The covalent bond may be, for example, a carbon-carbon, carbon-oxygen, oxygen-silicon, sulfur-sulfur, phosphorus-nitrogen, carbon-nitrogen, metal-oxygen, or other covalent bond. The hydrogen bond may be, for example, between hydroxyl, amine, carboxyl, thiol, and/or similar functional groups. For example, the species may include a functional group, such as a thiol, aldehyde, ester, carboxylic acid, hydroxyl, and the like, wherein the functional group forms a bond with the nanodiamond particle. In some cases, the species may be an electron-rich or electron-poor moiety wherein interaction between the nanodiamond particle and the species comprises an electrostatic interaction.

For example, the species may be associated with a functionalized nanodiamond particle comprising a —COOH, —OH, —NH$_2$, —SH, or —C=O functional group by reacting the functionalized nanodiamond particle and the species in the presence of a cross-linking agent. Non-limiting examples of suitable cross-linking agents include carbodiimides such as 1-ethyl-3-[3-dimethylaminopropyl] carbodiimide hydrochloride (EDC); amine-reactive compounds such as N-Hydroxysuccinimide ester, imidoester, and hydromethylphosphine; sulfhydryl-reactive compounds such as maleimide, pyridyl disulfides, and iodoacetyl; aldehyde-reactive compounds such as hydrazide and alkoxyamine; and photoreactive cross-linking agents such as aryl azides and diazirine. Other cross-linking agents are also possible. Those of ordinary skill in the art would be capable of selecting suitable cross-linking agents based upon the type of species selected and the teachings of this specification.

In some embodiments, the species may bind with a target analyte. In some cases, the species may comprise a biological or a non-biological (chemical) group capable of binding another biological or chemical molecule in a sample (e.g., a biological or chemical molecule present on an analyte). For example, the species may include a functional group, such as a thiol, aldehyde, ester, carboxylic acid, hydroxyl, amine, polyethelene glycol and the like, wherein the functional group forms a bond with the analyte. In some cases, the species may be an electron-rich or electron-poor moiety wherein interaction between the analyte and the species comprises an electrostatic interaction.

In some embodiments, the species and analyte interact via a binding event between pairs of biological molecules including proteins, nucleic acids, glycoproteins, carbohydrates, hormones, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a protein/receptor pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, and a metal ion/chelating agent pair. Specific non-limiting examples of species include peptides, proteins, DNA, RNA, and PNA. Other species and binding pairs are also possible. In an exemplary embodiment, the species is an antibody (e.g., an antibody to a target analyte).

In an exemplary embodiment, the species and analyte interact via an antibody/antigen pair binding event.

In another exemplary embodiments, the species and analyte interact via a protein/receptor pair binding event. For example, the species may comprise a protein such as disintegrin (e.g., Bitistatin) and the analyte may comprise a receptor molecule such as a fibrinogen receptor.

In some embodiments, the species and the analyte interact via a binding event between pairs of biological molecules including proteins, nucleic acids, glycoproteins, carbohydrates, hormones, or the like.

In some embodiments, the species is selected from the group consisting of (poly)peptides, (poly)nucleotides, and ligands. In an exemplary embodiment, the species is a polypeptide, such as a protein, an antibody, and/or an antigen. For example, in some embodiments, the antibody is an immunoglobulin such as IgA, IgG, IgM, IgE, or the like, In another exemplary embodiment, the species is a (poly) nucleotide (e.g., an oligonucleotide), such as DNA or RNA. In yet another exemplary embodiment, the species is a disintegrin such as albolabrin, applagin, barbourin, batroxostatin, bitistatin, obtustatin, schistatin, echistatin, elegantin, eristicophin, flavoridin, halysin, kistrin, mojastin, rubistatin, tergeminin, salmosin or triflavin. In some embodiments, the species may comprise a protein such as serum albumin (e.g., bovine serum albumin).

Examples of suitable nanodiamond particles functionalized with a species (e.g., Bitistatin) are discussed in more detail in U.S. Provisional Patent Application No. 62/383, 657, filed Sep. 6, 2016, entitled "Engineering and Utility of Fluorescent Nanodiamond Particles (NDP-F) for Diagnostics and Treatment of Blood Clots in Human and Veterinary Medicine," which is incorporated herein by reference in its entirety. Other functionalization methods are also possible.

Non-limiting examples of analytes that may be detected and/or quantified include a biological compound, a drug, a macromolecule, a salt, an electrolyte, an enzyme, a nucleic acid (e.g., a (poly)nucleotide), a carbohydrate, a (poly) peptide, a protein, a lipid, a phosphate, a sulfonate, a virus, a pathogen, a bacterium, a fungus, an oxidant, a reductant, a toxin, a surfactant, and combinations thereof.

In an exemplary set of embodiments, the analyte is a virus (e.g., ebola, Marburg, Bundibugyo, sudan, junin, lassa, MERS, small pox, Zika, pertussis, rubella, rubeola). In some embodiments, the analyte is a bacterial toxin (e.g., anthrax). In some embodiments the analyte is a biological entity associated with a particular parasite and/or fungus. Advantageously, the systems and methods described herein may be useful for the detection and/or quantification of viruses such as ebola.

In yet another exemplary set of embodiments, the analyte is a receptor molecule (e.g., a fibrinogen receptor). Advantageously, the systems and methods described herein may be useful for the detection of blood clots.

In some cases, the analyte may comprise a marker/antigen for a particular disease or condition. For example, in some cases, the analyte may be a marker/antigen associated with blood clots, traumatic brain injury, bone diseases (e.g., osteroporosis, osteoarthrosis), inflammation and/or (auto) immune diseases (e.g., Crohn, psoriasis) ulcers, cardiac ischemia and stroke, atherosclerosis, muscle diseases, Alzheimer's/Parkinson's, tumors and tumor metastasis, or others. For example, the systems and methods described herein may be useful for the detection and/or diagnosis in a subject of blood clots, traumatic brain injury, inflammation and/or (auto)immune diseases (e.g., Crohn's, psoriasis), ulcers, cardiac ischemia and stroke, atherosclerosis, muscle diseases, Alzheimer's/Parkinson's, tumors and tumor metastasis, or others.

Figure 1B:
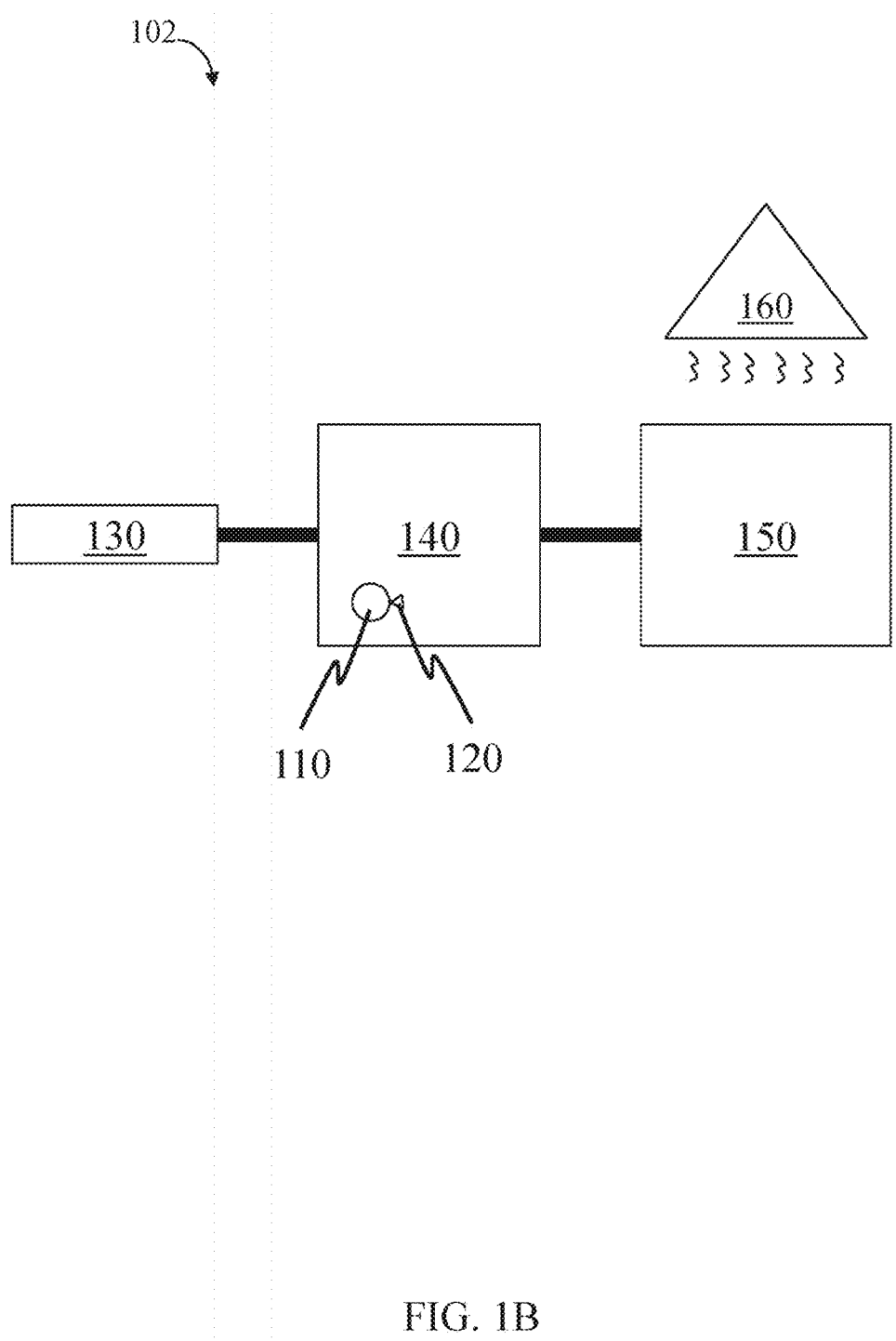
FIG. 1B is a schematic illustration of a system including fluorescent nanodiamond particles, according to one set of embodiments.

In some embodiments, the plurality of nanodiamond particles and the species associated with the nanodiamond particles are present (e.g., in a reservoir) and/or introduced into a fluidic device. For example, as illustrated in FIG. 1B, fluidic device 102 comprises a sample inlet 130 and a reservoir 140 in fluidic communication with sample inlet 130. In certain embodiments, reservoir 140 comprises a plurality of (fluorescent) nanodiamond particles 110 (and species 120 associated with nanodiamond particle 110).

In certain embodiments, a sample may be introduced to the sample inlet such that the sample flows into the reservoir and the sample interacts with the plurality of nanodiamond particles and species. In some embodiments, an analyte, if present in the sample, binds to the species.

In some cases, detection region 150 may be positioned downstream of, and/or in fluidic communication with, reservoir 140.

In certain embodiments, a detector 160 may be positioned proximate detection region 150. The detector, in some cases, may be configured to quantify an emission (e.g., an intensity of the emission, a wavelength of the emission) at the detection region. In some cases, the emission may be fluorescent and/or near-infrared. For example, the analyte, if present, may bind to the species. In some such cases, the analyte may bind to a second species (e.g., an antibody) associated with (e.g., bound to) the detection region. In some embodiments, the analyte bound to the second species and the first species (associated with the nanodiamond particles) may be detected and/or quantified by measuring (e.g., via the detector) the emission of the nanodiamond particles.

In some embodiments, a detector may be positioned proximate a region of a subject suspected of containing an analyte and/or a clot. For example, the plurality of (fluorescent) nanodiamond particles functionalized with a species may be administered to a subject, and the detector may be positioned proximate the subject such that any nanodiamond particles bound to the analyte and/or clot may be detected (e.g., via an emission of the nanodiamond particles).

Any suitable detector may be used with the devices and methods described herein. For example, in some embodiments, the detector may be an optical detector (e.g., fluorescence detectors, visible light and/or UV detectors, near infrared detectors, microscopes).

In some embodiments, the emission is a fluorescent emission. In certain embodiments, the wavelength of the emission is greater than or equal to 250 nm, greater than or equal to 300 nm, greater than or equal to 350 nm, greater than or equal to 400 nm, greater than or equal to 450 nm, greater than or equal to 500 nm, greater than or equal to 550 nm, greater than or equal to 600 nm, or greater than or equal to 650 nm. In certain embodiments, the wavelength of the emission is less than or equal to 700 nm, less than or equal to 650 nm, less than or equal to 600 nm, less than or equal to 550 nm, less than or equal to 500 nm, less than or equal to 450 nm, less than or equal to 400 nm, less than or equal to 350 nm, or less than or equal to 300 nm. Combinations of the above-referenced ranges are also possible (e.g., greater than or equal to 250 nm and less than or equal to 700 nm). Other ranges are also possible.

In certain embodiments, the emission is a near infrared emission. In some embodiments, the wavelength of the emission is greater than 700 nm, greater than or equal to 750 nm, greater than or equal to 800 nm, greater than or equal to 850 nm, greater than or equal to 900 nm, or greater than or equal to 950 nm. In certain embodiments, the wavelength of the emission is less than or equal to 1000 nm, less than or equal to 950 nm, less than or equal to 900 nm, less than or equal to 850 nm, less than or equal to 800 nm, or less than or equal to 750 nm. Combinations of the above-referenced ranges are also possible (e.g., greater than 700 nm and less than or equal to 1000 nm). Other ranges are also possible.

In some embodiments, the nanodiamond particle may emit a fluorescent and/or near infrared emission upon excitation by electromagnetic radiation having a particular wavelength. For example, in some embodiments, the nanodiamond particle may be exposed to electromagnetic radiation having a wavelength of greater than or equal to 250 nm, greater than or equal to 300 nm, greater than or equal to 350 nm, greater than or equal to 400 nm, greater than or equal to 450 nm, greater than or equal to 500 nm, greater than or equal to 550 nm, greater than or equal to 600 nm, greater than or equal to 650 nm, greater than or equal to 700 nm, greater than or equal to 750 nm, greater than or equal to 800 nm, greater than or equal to 850 nm, greater than or equal to 900 nm, or greater than or equal to 950 nm (e.g., such that the nanodiamond particle emits a fluorescent emission and/ or near infrared emission in one of the above-referenced ranges). In certain embodiments, the nanodiamond particle may be exposed to electromagnetic radiation having a wavelength of less than or equal to 1000 nm, less than or equal to 950 nm, less than or equal to 900 nm, less than or equal to 850 nm, less than or equal to 800 nm, or less than or equal to 750 nm, less than or equal to 700 nm, less than or equal to 650 nm, less than or equal to 600 nm, less than or equal to 550 nm, less than or equal to 500 nm, less than or equal to 450 nm, less than or equal to 400 nm, less than or equal to 350 nm, or less than or equal to 300 nm. Combinations of the above-referenced ranges are also possible (e.g., greater than or equal to 250 nm and less than or equal to 1000 nm, greater than or equal to 550 nm and less than or equal to 650 nm). Other ranges are also possible.

While much of the description herein is in the context of (fluorescent) nanodiamond particles, those of ordinary skill in the art would understand, based upon the teachings of this specification, that other particles are also possible. For example, in some embodiments, the device may comprise a particle such as a nanoparticle (e.g., a silica nanoparticle, a sapphire nanoparticle, a garnet nanoparticle, a ruby nanoparticle) having an emission in one of the above referenced ranges associated with a species (e.g., a species capable of binding to one or more target analytes). In some cases, the particle may be autofluorescent. In other cases, the particle may be functionalized with (e.g., associated with) a fluorescent molecule.

Figure 2A:
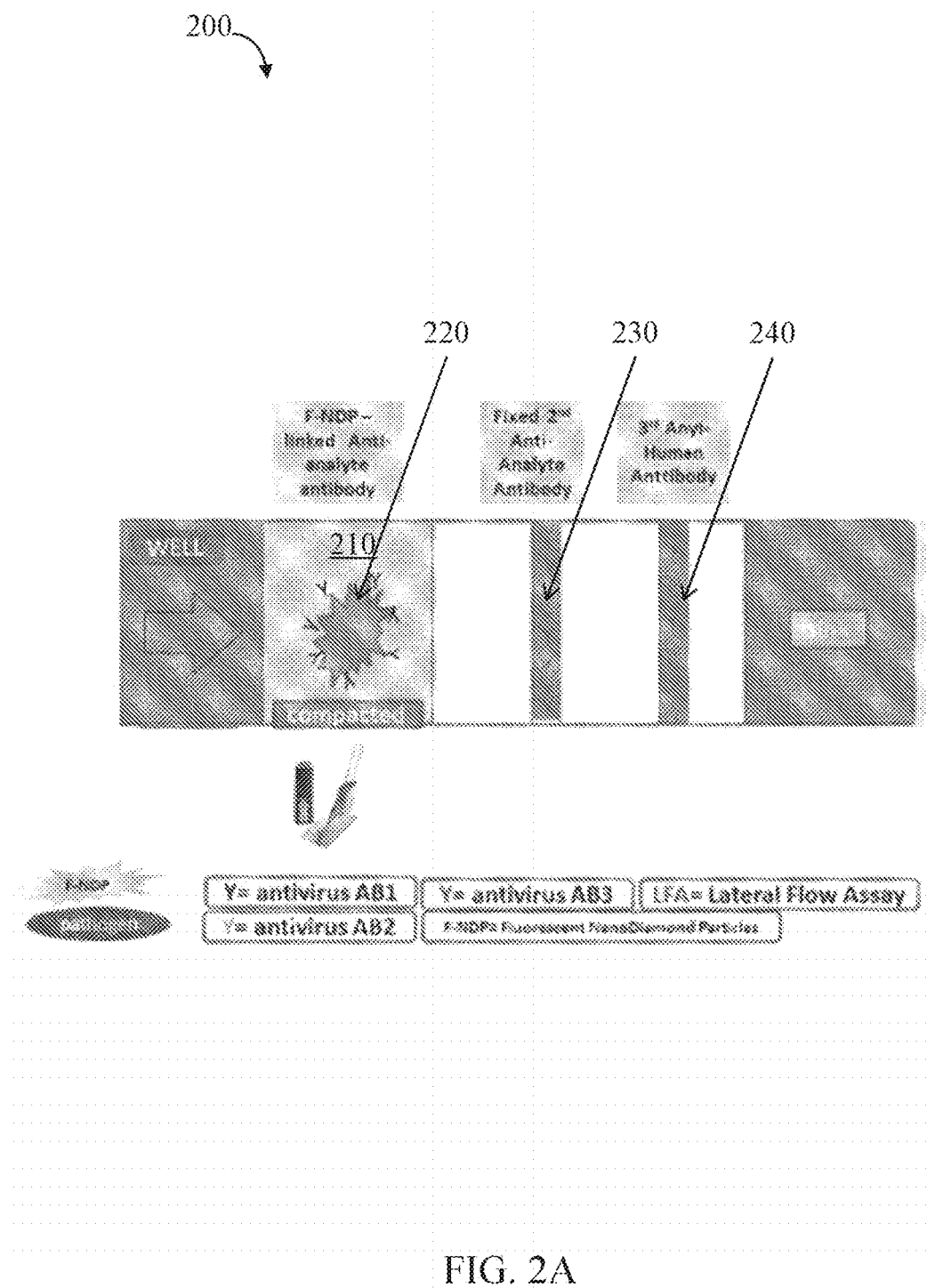
FIG. 2A is a schematic illustration of a system including fluorescent nanodiamond particles for detection of an analyte, according to one set of embodiments.

In some embodiments, the fluidic device (e.g., comprising a sample inlet and a reservoir comprising a plurality of nanodiamond particles and a species associated with the nanodiamond particles) comprises a lateral flow assay configuration (e.g., in a lateral flow device). Those of ordinary skill in the art would understand, based upon the teachings of this specification, how to incorporate a plurality of nanodiamond particles and a species associated (e.g., bound) to the nanodiamond particles into a lateral flow assay device. For example, as illustrated schematically in FIG. 2A, in an exemplary embodiment, system 200 comprises a lateral flow assay format. In certain embodiments, system 200 comprises reservoir 210 comprising a plurality of fluorescent nanodiamond particles 220 bound to a first species. Downstream of reservoir 210, in certain embodiments, is a second reservoir 230 comprising a second species (e.g., a first antibody to a target analyte) and a third reservoir 240 comprising a third species (e.g., a second antibody capable of binding to the antibody to the target analyte). In certain embodiments, the first species and the second species are the same.

Figure 2B:
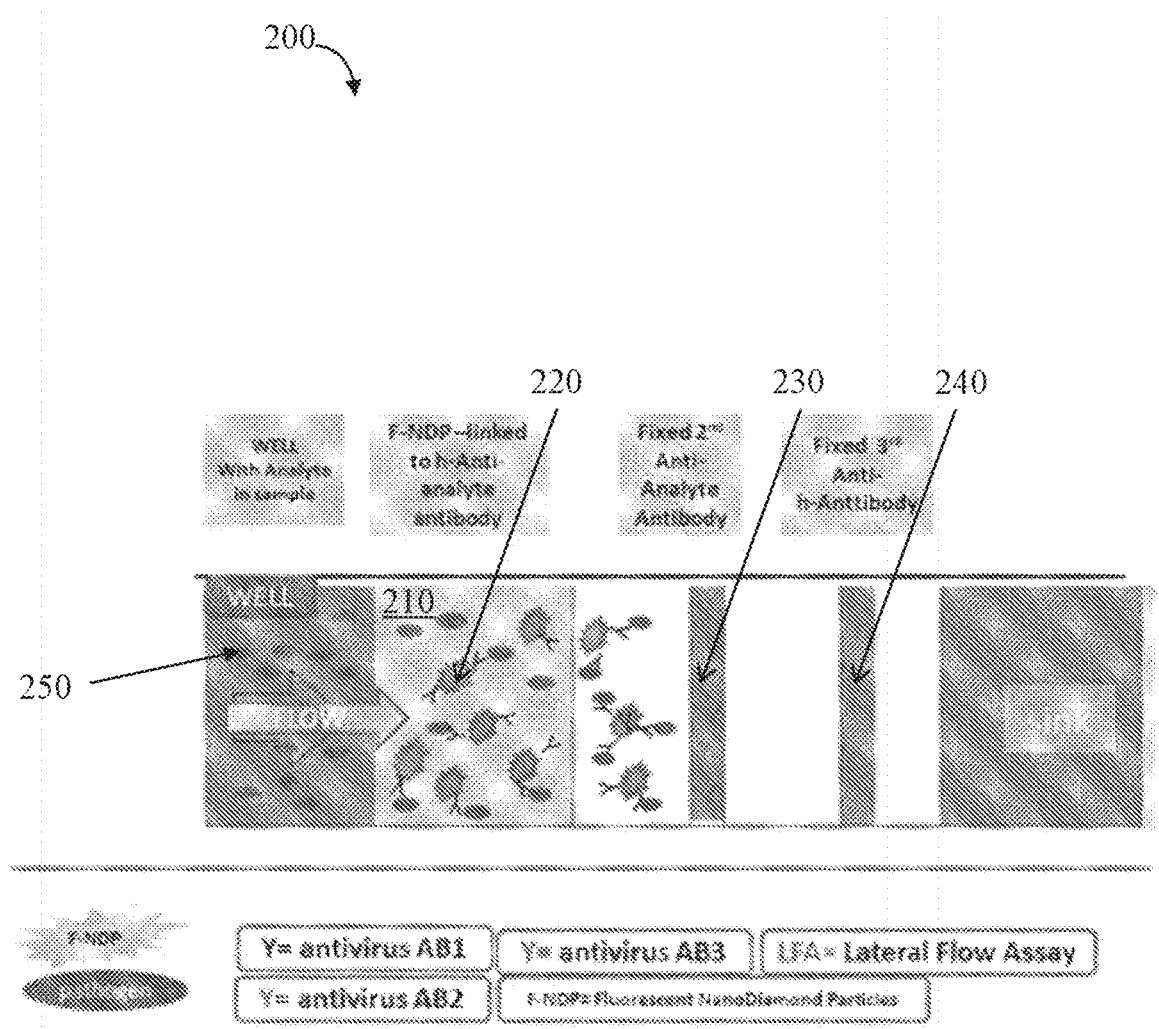
FIG. 2B is a schematic illustration of a system including fluorescent nanodiamond particles for detection of an analyte upon introduction of a sample suspected of containing the analyte, according to one set of embodiments.
Figure 2C:
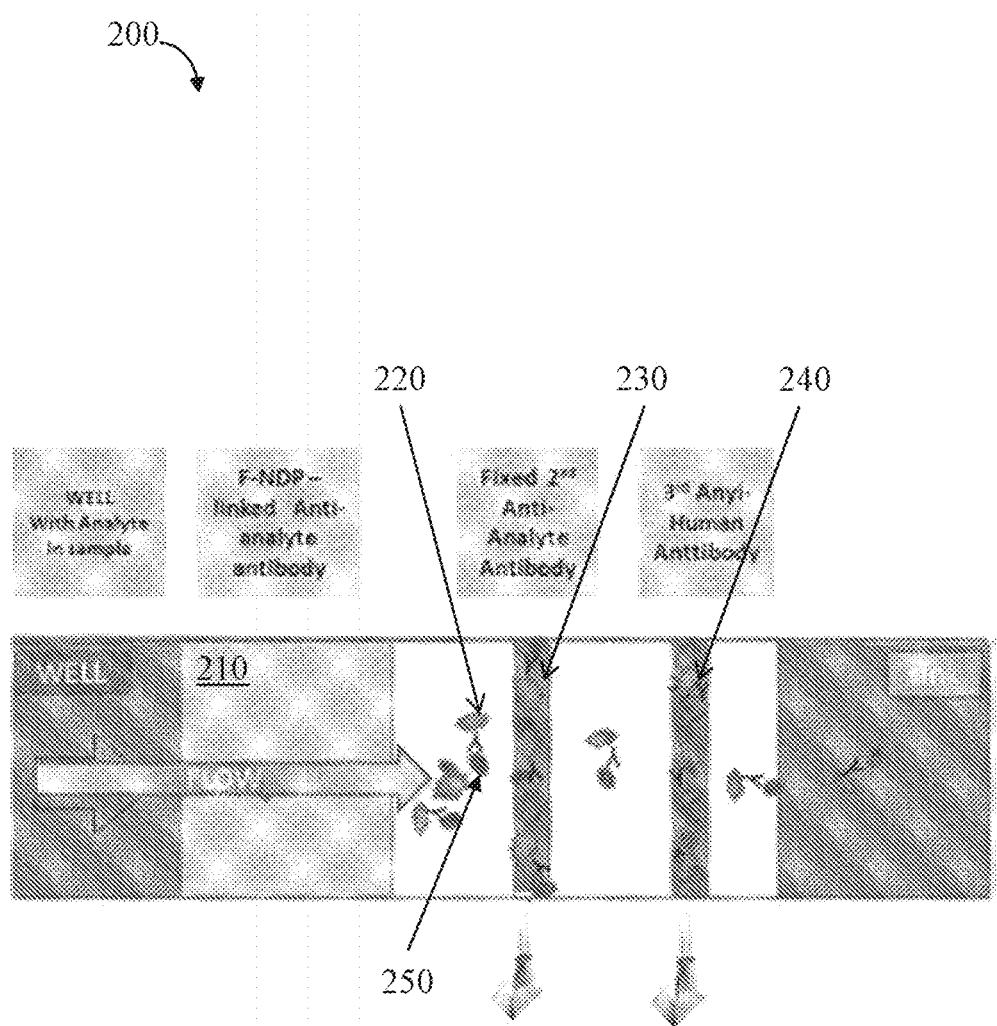
FIG. 2C is a schematic illustration of a system including fluorescent nanodiamond particles for detection of an analyte after introduction of a sample suspected of containing the analyte, according to one set of embodiments.

Now referring to FIG. 2B, a sample suspected of containing an analyte 250 may be introduced into system 200 (e.g., such that the sample flows and interacts with reservoir 210). In some embodiments, at least a portion of analyte 250 binds to the species on plurality of fluorescent nanodiamond particles 220. As illustrated in FIG. 2C, as the sample suspected of containing analyte 250 flows along the system, at least a portion of the analytes 250 (e.g., now bound to the species and/or plurality of fluorescent nanodiamond particles 220) bind to the second species in reservoir 230. In some cases, at least a portion of plurality of fluorescent nanodiamond particles 220 not bound to the analyte may be captured in reservoir 240 (e.g., where the third species is capable of binding to the first species).

In some cases, the devices and systems herein may be multiplexed. That is to say, in some embodiments, the devices may comprise two or more, three or more, four or more, or five or more fluidic components and/or reservoirs comprising a plurality of nanodiamond particles. In some such embodiments, more than one analyte may be detected, if present in the sample, in a single device. In certain embodiments, one or more analytes may be detected in a device comprising a plurality of fluidic components and/or reservoirs comprising a plurality of nanodiamond particles.

In an exemplary embodiment, a sample suspected of containing an analyte may be introduced into a fluidic channel of a fluidic device, exposing the sample to a species bound to a plurality of fluorescent nanodiamond particles such that the analyte, if present, binds to at least a portion of the species bound to the plurality of fluorescent nanodiamond particles. In some embodiments, any fluorescent nanodiamond particles and species not bound to the analyte may be removed and a fluorescence emission of the plurality of fluorescent nanodiamond particles bound to the analyte may be quantified. As described herein, in some cases, the amount of analyte present in the sample may be correlated with the intensity of the fluorescence emission.

In another exemplary embodiment, a system comprises a sample inlet, a reservoir in fluidic communication with the sample inlet, the reservoir comprising a plurality of fluorescent nanodiamond particles, a plurality of a first species bound to the plurality of fluorescent nanodiamond particles, and a detection region in fluidic communication with the reservoir, the detection region comprising a plurality of a second species bound to the detection region. In some cases, the detector may be configured to quantify a fluorescent emission at the detection region and/or configured to quantify an infrared signal at the detection region.

In yet another exemplary embodiment, a fluidic device comprises a sample inlet, a reservoir in fluidic communication with the sample inlet, the reservoir comprising a plurality of fluorescent nanodiamond particles, a plurality of a first species bound to the plurality of fluorescent nanodiamond particles, and a detection region in fluidic communication with the reservoir, the detection region comprising a plurality of a second species bound to the detection region. In some embodiments, the fluidic device may further comprise a control region in fluidic communication with the detection region, the control region comprising a plurality of a third species bound to the control region. In some such embodiments, the third species may be the same or different as the first species and/or the second species. For example, the first species bound to the plurality of fluorescent nanodiamond particles may be a first antibody (e.g., capable of binding selectively to the target analyte), the second species may be the first antibody or may be a second antibody different than the first antibody (e.g., capable of binding selectively to the target analyte), and the third species may be an anti-antibody to the first antibody. The control region may provide an indication, if an emission is present, that the system is working properly (e.g., the plurality of nanodiamond particles were properly featured and introduced into the sample).

In some embodiments, the fluidic device comprises an absorbent material. In some embodiments, an absorbent region comprising the absorbent material is positioned downstream of, and in fluidic communication with, the detection region and/or the control region. In some cases, the absorbent material is associated with one or more components (e.g., the reservoir, the detection region) of the fluidic device. In some cases, the absorbent material may at least partially drive the flow of the sample in the fluidic device (e.g., wicking). In other embodiments, capillary action may at least partially drive the flow of the sample in the fluidic device.

Non-limiting examples of suitable absorbent materials include solid materials, porous materials, particles, powders, and gels. In some embodiments, the absorbent material may comprise fabric, cellulose, cotton, and/or a polymer. Those of ordinary skill in the art would be capable of selecting suitable absorbent materials based upon the teachings of this specification.

In another exemplary embodiment, the methods described herein comprise administering, to a subject suspected of having a particular analyte (e.g., present in the bloodstream), a plurality of fluorescent nanodiamond particles bound to a species such that the species may bind to the analyte, if present, and detecting a fluorescent and/or near infrared emission of the plurality of fluorescent nanodiamond particles comprising the species bound to, if present, the analyte. In some cases, detecting a fluorescent emission indicates the presence of a blood clot in the subject. In certain embodiments, detecting a fluorescent emission indicates the presence of a virus (e.g., ebola, Marburg, Bundibugyo, sudan, junin, lassa, MERS, etc.) in the subject.

As should be evident, in some embodiments, the present invention also provides a diagnostic agent for detection or imaging of thrombotic events in a human or non-human animal, where the agent comprises a fluorescent nanodiamond particle chemically bonded to disintegrin Bitistatin (Bt). In certain embodiments, the fluorescent nanodiamond particle and the Bt are covalently bonded. The diagnostic agent may be fluorescent as a result of an intrinsic property of the nanodiamond particle. In some embodiments, the diagnostic agent emits a detectable electromagnetic signal when excited by an electromagnetic source.

Additional exemplary embodiments relate to a method for diagnosis or prognosis of a thrombo-embolic event. In these embodiments, the method comprises: administering to a subject suspected of having suffered from or suspected of being at risk of, a thrombo-embolic event, a diagnostically effective amount of the diagnostic agent of the invention; allowing sufficient time for the diagnostic agent to localize to the site(s) of thrombus; and detecting the diagnostic agent by detecting fluorescence emission of the diagnostic agent. The method can be practiced as a method of detection of activated platelets and/or a method of detecting clots or clot formation in subjects.

Another exemplary embodiment of the invention relates to a kit. The kit may include the diagnostic agent of the invention in packaged form suitable for distribution, delivery, and/or storage for use in a diagnostic method (e.g., a diagnostic method for detection of a thrombus). The packaged form may include a suitable material for distribution, delivery, and/or storage of the diagnostic agent. In certain embodiments, the kit further comprises, in packaged combination, one or more reagents or devices for administration of the diagnostic agent of the invention to a subject. The kit can also include a device that emits excitation energy for the diagnostic agent, and preferably further includes a detector for detection of emission response from the diagnostic agent. In a particular exemplary embodiment, the device (e.g., a device that emits excitation energy, a detector for detection of emission response) is a hand-held device.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

A "subject" or a "patient" refers to any mammal (e.g., a human), for example, a mammal that may be susceptible to a disease or bodily condition. Examples of subjects or patients include a human, a non-human primate, a cow, a horse, a pig, a sheep, a goat, a dog, a cat or a rodent such as a mouse, a rat, a hamster, or a guinea pig. Generally, the invention is directed toward use with humans. A patient may be a subject diagnosed with a certain disease or bodily condition or otherwise known to have a disease or bodily condition. In some embodiments, a patient may be diagnosed as, or known to be, at risk of developing a disease or bodily condition. In other embodiments, a patient may be suspected of having or developing a disease or bodily condition, e.g., based on various clinical factors and/or other data. In some cases, the patient may be diagnosed with having or developing a particular disease or bodily condition after the detection and/or quantification of an analyte (e.g., a virus, an antigen, an antibody) in a sample obtained from the patient. In some embodiments, a subject may demonstrate health benefits, e.g., upon administration of the fluorescent nanodiamond particles.

As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. If two or more fluids are present, each fluid may be independently selected among essentially any fluids (liquids, gases, and the like) by those of ordinary skill in the art.

The following examples are intended to illustrate certain embodiments of the present invention, but do not exemplify the full scope of the invention.

EXAMPLES

Prophetic Example 1

The following example demonstrates an exemplary functionalized fluorescent nanodiamond particle with a species (e.g., for binding to anti-human IgG-AP).

Figure 3:
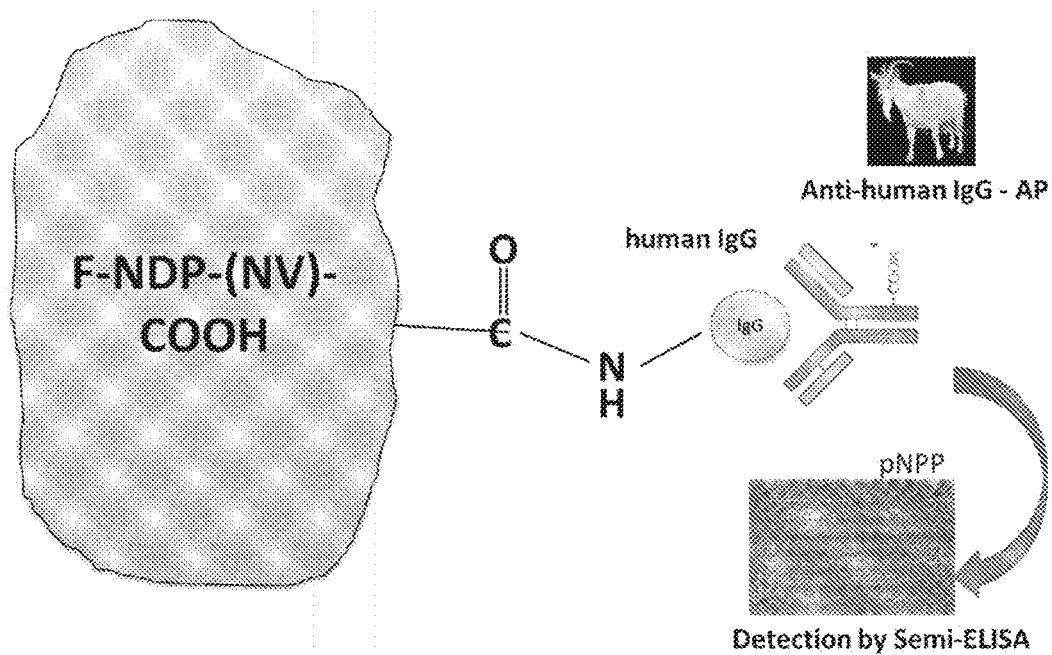
FIG. 3 is a schematic illustration of an exemplary fluorescent nanodiamond particle functionalized with a species such as human IgG, according to one set of embodiments.

FIG. 3 illustrates the conjugation of a fluorescent nanodiamond particle (F-NDP), functionalized with a carboxylic acid group, and bound to a species (e.g., Bitistatin). Such functionalized F-NDPs can be used, for example, to image and detect the presence of blood clots using external scanners (e.g., detectors for UV and/or NIR emissions).

Example 2

The following example demonstrates the incorporation of fluorescent nanodiamond particles into an exemplary system such as a lateral flow assay format.

Figure 4:
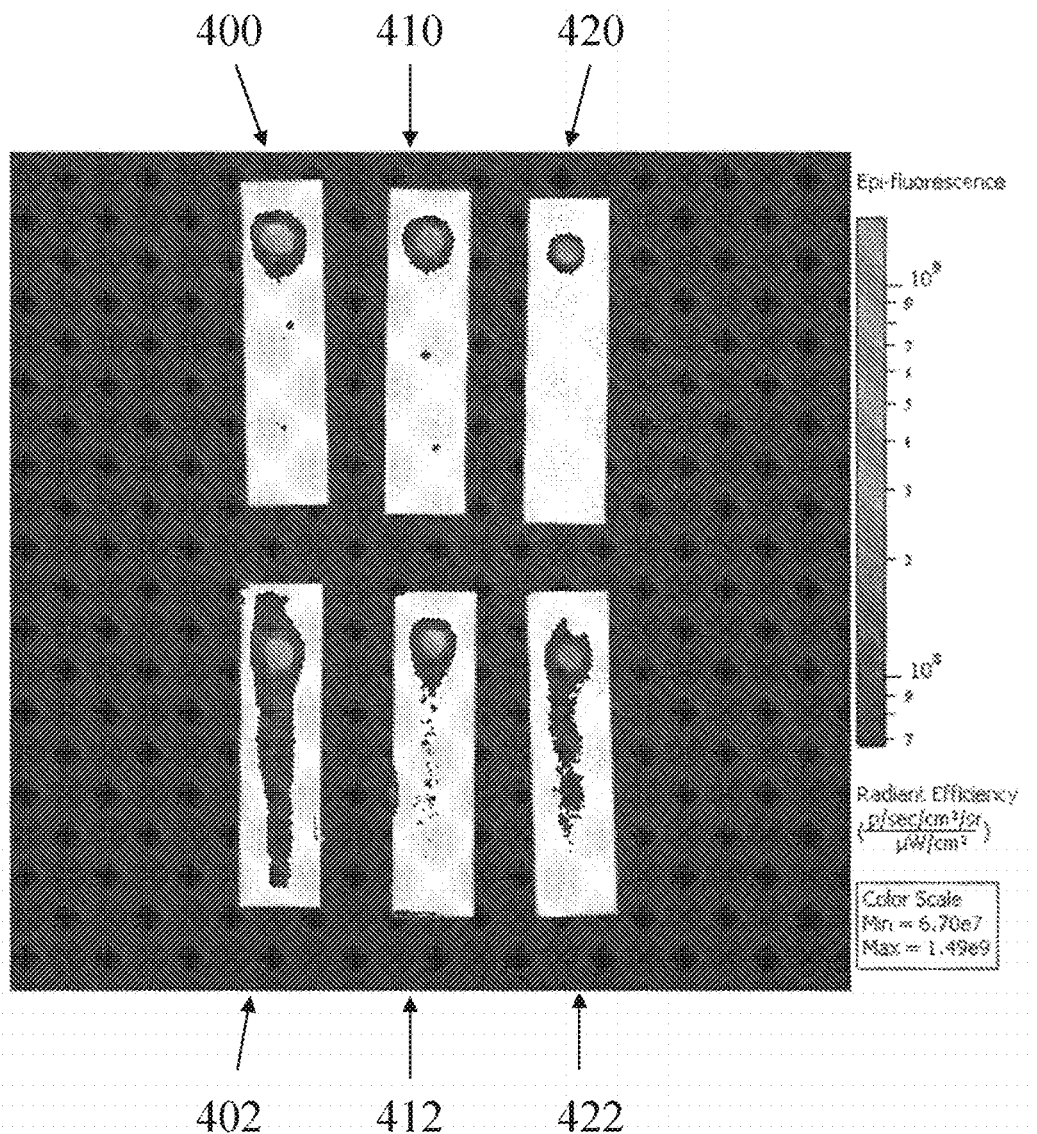
FIG. 4 is a photograph of an exemplary system including a reservoir comprising a plurality of fluorescent nanodiamond particles, according to one set of embodiments.

FIG. 4 shows the loading of three exemplary systems (system 400, system 410, and system 420), each with a reservoir of fluorescent nanodiamond particles (shown as the dot in each system) placed on a nitrocellulose substrate. Upon introduction of water to system 400, water with 1% Tween 20 to system 410, and 10 mM sodium phosphate with 1% Tween 20 to system 420, flow of the fluorescent nanodiamond particles along the substrate of each device was observed (system 402, system 412, and system 422 respectively).

Example 3

The following example demonstrates the use of fluorescent nanodiamond particles (F-NDP) conjugated with a species (e.g., human IgG) for the detection of an analyte (e.g., anti-human IgG).

Figure 5:
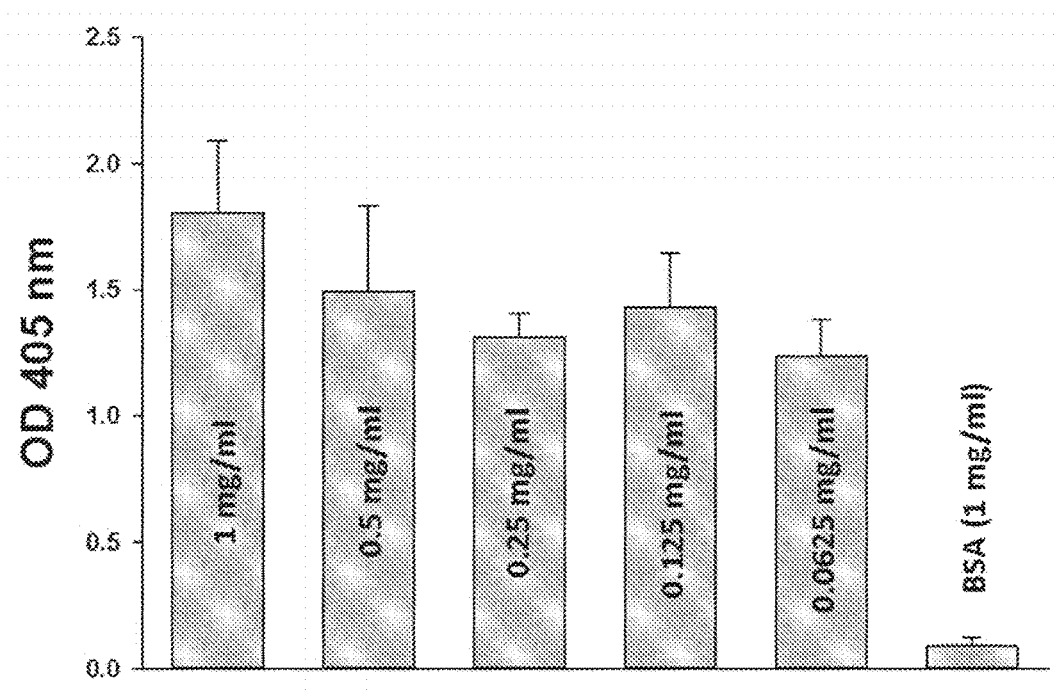
FIG. 5 is a plot of semi-ELISA for detection of human IgG bound to fluorescent nanodiamond particles at various concentrations versus control (bovine serum albumin (BSA)), according to one set of embodiments.

FIG. 5 shows a plot of semi-ELISA for detection of human IgG coupled to the F-NDP NV (700 nm). F-NDP were coupled to human IgG, or BSA (control), which were used in concentrations as indicated, per 1 mg of F-NDP. 0.2 mg of each F-NDP-IgG or F-NDP-BSA sample were used for semi-ELISA, which was performed on a U-shape bottom 96-well plate. The plate was blocked overnight with 3% BSA in PBST. F-NDP-IgG were blocked with 3% BSA in PBST by incubation for 1 hour at 37° C. Blocking agent was removed by centrifugation (1,000 g) at room temperature and washed 2× with PBST. Goat anti-human IgG APconjugated (Sigma Inc.), diluted 1:5000, was added and incubated for 1 hr. as above. Final washing was performed as above, and p-nitrophenyl phosphate substrate (pNPP) to alkaline phosphatase (AP) was added. Color was developed for 30 min, and NDP samples on plate were centrifuged. Supernatant was transferred to a flat bottom 96-well plate and read using an ELISA plate reader under 405 nm wave length. Error bars represent four repeats in semi-ELISA from the same samples.

Example 4

Figure 6:
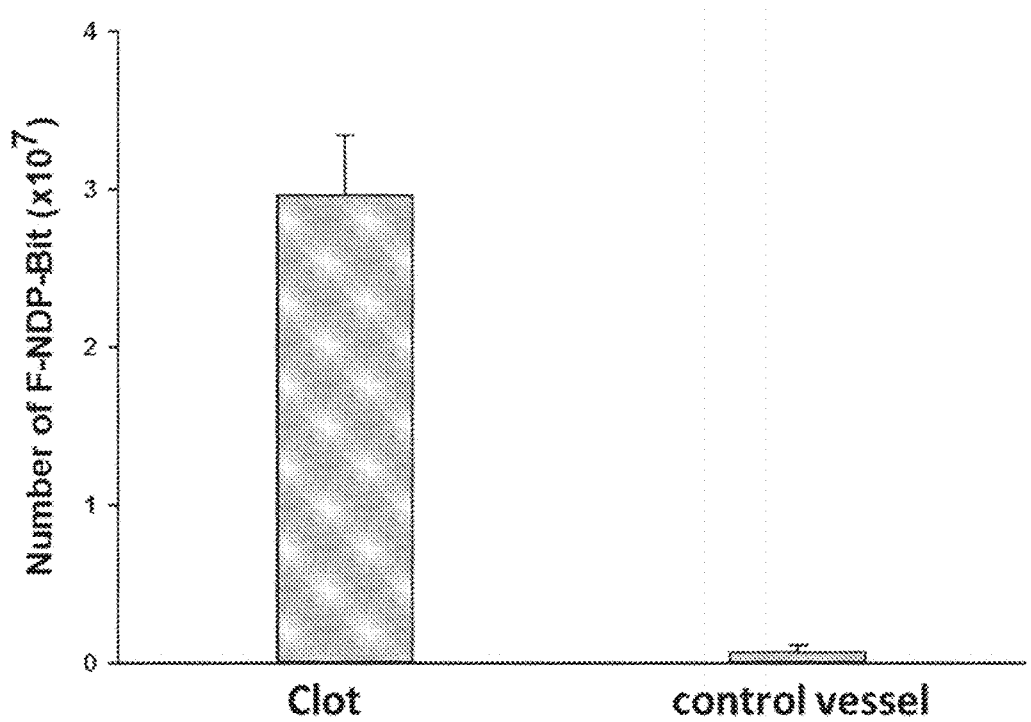
FIG. 6 is a plot of the quantification of fluorescent nanodiamond particles functionalized with bitistatin in a carotid artery clot versus control vessels in rats, according to one set of embodiments.

The following example demonstrates the use of F-NDPs functionalized with a species (e.g., Bitistatin (Bt)) for the detection of blood clots. FIG. 6 shows the accumulation number of F-NDP-Bt in carotid arteries in rats with generated clots. Carotid arteries with generated clots or not (control) were dissected from rats at the end of the experiments. Vessels were solubilized with 12 N HCl by overnight incubation at 60° C. in a ratio of 100 mg per ml. The resulting solution was diluted 10× with water and centrifuged using 14,000 rpm at room temperature and re-suspended in the same volume of water. F-NDP-Bt were counted using a hemocytometer with fluorescence microscope (40× objective, TRITC wavelengths). Presented numbers show total accumulated particles. Error bars represent standard deviation from three rats (clot value=2.8±0.38× $10^7$; control value=6.6±4.7×$10^5$)

Figure 7A:
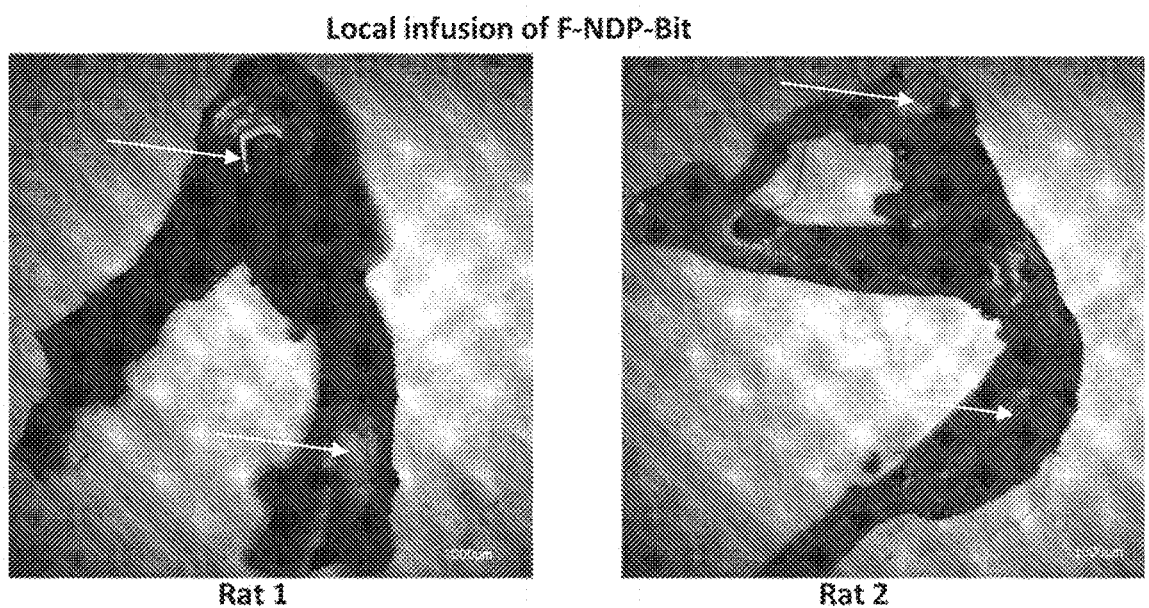
FIG. 7A shows scanning confocal microscopy images of carotid arteries from rats with generated clots with fluorescent nanodiamond particles introduced, according to one set of embodiments.

FIG. 7A is a scanning confocal microscope (SCM) image of carotid arteries from rats with a generated clot. Generation of a clot was performed using ferric chloride. F-NDP-Bt suspension was injected locally, close to the clot. Rats were euthanized, and carotid arteries with clots were dissected. Imaging was performed using SCM. Wavelengths used for measurement: excitation Cy5.5 BkG (580-610 nm), emission Cy5.5 (695-770 nm). For background subtraction: excitation GFP (445-490 nm), emission Cy5.5 (695-770 nm). NIR detection of F-NDP—Bit is indicated by the white arrows.

Figure 7B:
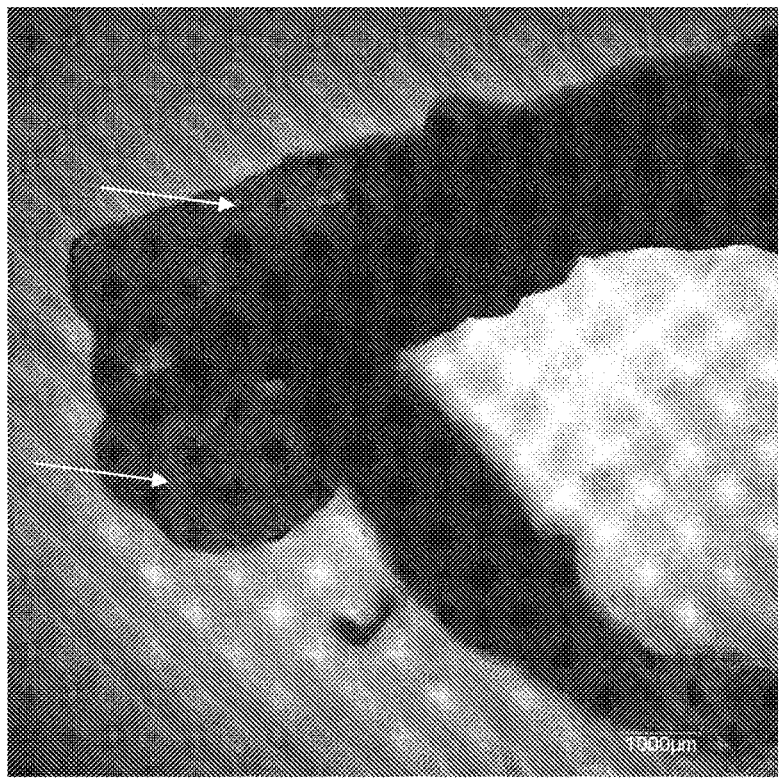
FIG. 7B shows a scanning confocal microscopy image of a carotid artery from a rat with a generated clot with fluorescent nanodiamond particles introduced, according to one set of embodiments.

FIG. 7B shows a scanning confocal microscope image of carotid arteries from rats with generated clot. Generation of a clot was performed using ferric chloride. F-NDP-Bt suspension was systemically injected to the animal tail. The rat was euthanized, and the carotid artery with clots was dissected. Imaging was performed using SCM. Wavelengths used for measurement: excitation Cy5.5 BkG (580-610 nm), emission Cy5.5 (695-770 nm). For background subtraction: excitation GFP (445-490 nm), emission Cy5.5 (695-770 nm). NIR detection is indicated by white arrows.

Figure 8:
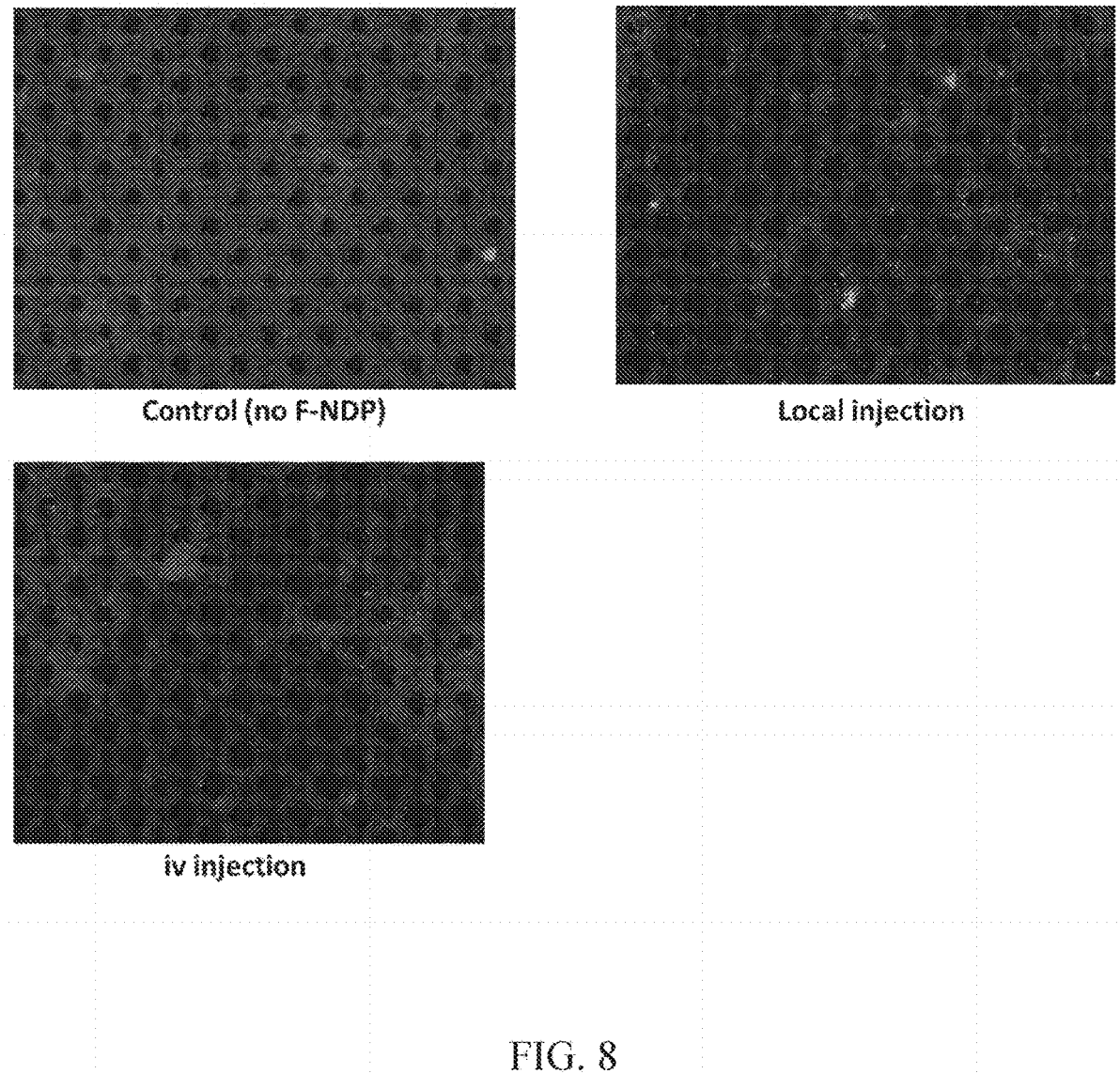
FIG. 8 shows images of tissue suspensions of clots treated or not with fluorescent nanodiamond particles, injected systematically to the femoral vein close to a clot generated in carotid artery, according to one set of embodiments.

FIG. 8 shows images of tissue suspensions of clots treated or not with F-NDP-Bt, injected systematically to the femoral vein close (locally) to the clot generated in carotid artery. Tissues of the clot were manually homogenized in the presence of RIPA buffer (Triton X-100 based) in ratio one vein for 100 ml. Suspension of the lysate was applied on glass slide and immediately analyzed under the microscope. Magnification 100×.

Example 5

The following example demonstrates the functionalization of F-NDP (i.e., NDP-F) with a polypeptide (e.g., Bitistatin (Bt)) and the detection of one or more analytes and/or blood clots.

The methodology of coupling proteins/peptides to carboxyl-functionalized NDP-F is described herein. Preservation of the active domains responsible for the biological action of the coupled proteins/peptides remains challenging, and is generally considered to be a trial and error endeavor. A major innovation of the present invention is the demonstration of a concentration-dependent association of the engineered NDP-F-Bt agent to purified PFR. The selection of Bt was based on the high selectivity/specificity of Bt to the PFR, concomitant with negligible interactions with other RGD-dependent integrins, such as receptors for vitronectin (avb3) and fibronectin (a5b1). The present strategy to utilize Bt for clot imaging differs significantly from previous studies aimed at demonstrating the utility of Tc99-Bitistatin to map blood clots in vivo. The present imaging strategy is based on the innate near infrared (NIR) fluorescence emitted upon excitation of the NDP-F, thereby eliminating high radioactivity exposure required by other imaging techniques. It is also envisioned that coupling Bt (or other polypeptides) to a nanoparticle will be beneficial for the extension of the lifetime of the Bt at the site of its biological target.

Figure 9:
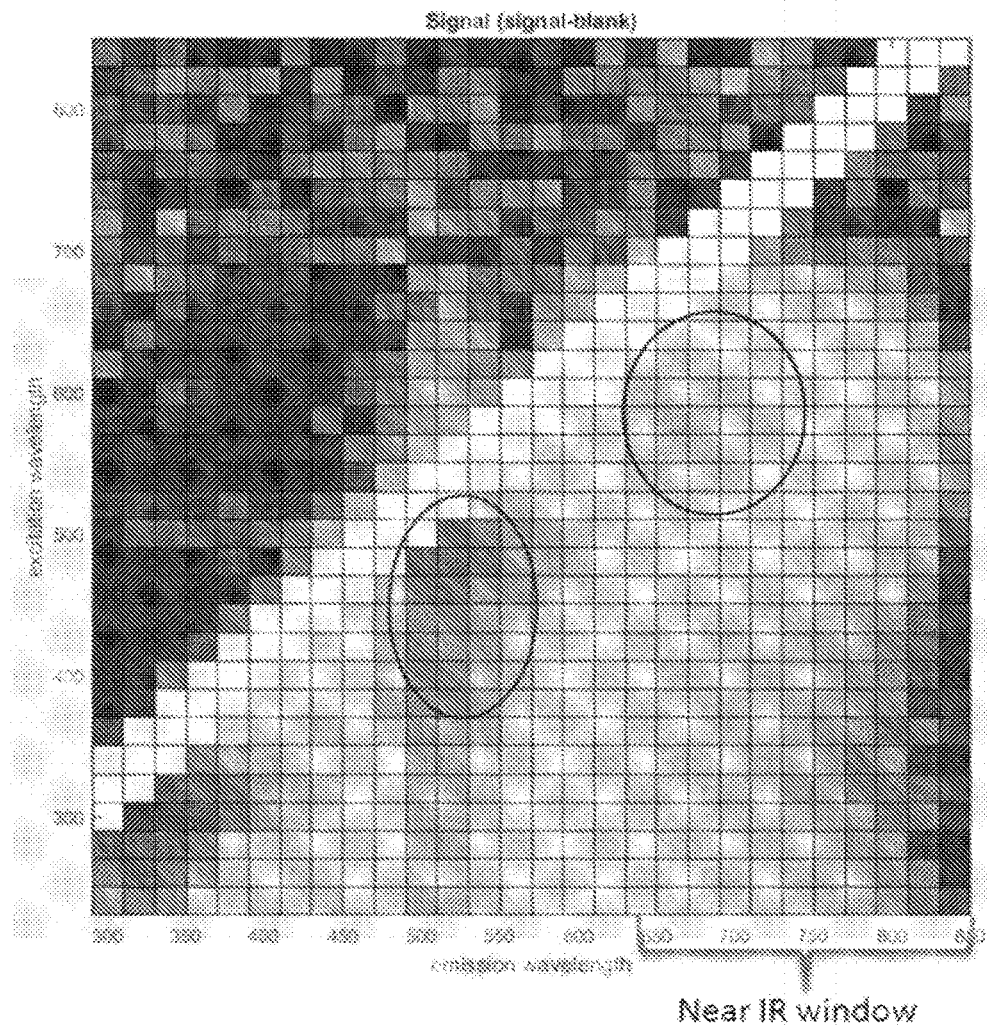
FIG. 9 is a fluorescence scan result showing two dimensional screening of excitation vs. emission wavelengths to optimize fluorescence of NDP-Fs used in the exemplary embodiment. The figure shows optimization of the maximal fluorescence for NDP-Fs. The heat map represents the results of fluorescence screening in the entire spectrum of excitation vs. emission wavelengths. The experiment was performed using a Tecan plate reader. NDP-Fs were applied on a 96-well plate (0.3 mg/0.1 ml) as a suspension in PBS. The blank, or negative control, was established using PBS alone.

Fluorescent nano-diamond particles (NDP-F or FNDP) functionalized by carboxyl groups (—COOH) were purchased from Adamas Nanotechnologies, Inc. (Raleigh, N.C.). Size distribution analysis revealed the peak of the diameter of the NDP was 734.5 (±223.6, SD) nm. Optimization of fluorescence for the NDPs was performed by 2D screening of excitation vs. emission wavelengths (FIG. 9). Two areas of optimal fluorescence were established for NDPs, which should be useful for application in medical imaging (circled on FIG. 9). Detailed screening revealed two optimal correlations of excitation vs. emission wavelengths: 480 nm vs. 520 nm, and 565 nm vs. 700 nm. The first correlation represents the typical green fluorescence, whereas the second is characterized by the long Stokes shift of fluorescence with near IR emission. The near IR emission is very useful for detection in vivo because it is in the optical therapeutic window of autofluorescence of factors present in human and non-human animal non-invasive imaging environments (e.g., water, hemoglobin, oxyhemoglobin, melanin).

The NDP-Fs were found to be resistant to photobleaching. Exposure of the slides containing NDPs to intense fluorescence light resulted in no changes in the intensity of their fluorescence in the time points up to 5 hours (data not shown).

Bitistatin is generally derived from snake venom and belongs to the disintegrin family of proteins. It has previously been investigated as a potential reagent for detection of deep venous thrombosis (DVT) using radioactive tags. This RGD-disintegrin showed desirable parameters for detection of DVT when compared with other snake venom disintegrins, such as kistrin and barbourin. Therefore, this fibrinogen receptor-binding ligand was selected for coupling to NDP-Fs for the purpose of detecting activated platelets (or their aggregates) in clots present in the venous circulation (vein thrombus).

Bitistatin is generally an 83-amino acid polypeptide, which originally was isolated from venom of *Bitis arietants*. This naturally occurring polypeptide was purified from the same snake venom using methodology developed in the laboratory for purification of other snake venom disintegrins (Marcinkiewicz, Cezary, et al. "EC3, a novel heterodimeric disintegrin from Echis carinatus venom, inhibits α4 and α5 integrins in an RGD-independent manner." Journal of Biological Chemistry 274.18 (1999): 12468-12473; incorporated herein by reference). Briefly, this method includes two steps of reverse phase HPLC with application of $C_{18}$ column and a linear gradient of acetonitrile as a protein elution agent. Purity of the obtained Bt was tested by SDS-PAGE and quantified by digitization of bands on standard protein gels by Coomassie blue staining. The content of Bt was estimated at over 98% in the final protein preparation. This preparation was suspended in PBS for coupling to NDPs.

The active site of Bt was characterized and found to include an RGD motif, which is important for ligand binding to certain integrins, such as αIIbβ3, αvβ3, and α5β1. Bt is quite selective in that it has been shown to bind only the PFR, αIIbβ3 integrin, which is exclusively expressed on circulating platelets. The aspartic acid in the RGD sequence was recognized by site-directed mutagenesis of recombinant proteins and short peptide synthesis as the most essential amino acid for disintegrin binding to the fibrinogen receptor. It was hypothesized by the inventors that coupling of Bt to NDPs that were functionalized by an attached amine group could affect the activity of disintegrin by engagement with carboxyl groups present in the side chain of the aspartic acid. Therefore, NDPs functionalized by a carboxyl group were selected to attach the Bt on NDPs surfaces.

Coupling of carboxyl (—COOH) groups present on NDPs to $NH_2$ groups present on Bt was performed using a standard protocol developed previously (Grabarek and Gergely, 1990). This method was based on the application of the cross-linker 1-ethyl-3-[3-dimethylaminopropyl]carbodiimide hydrochloride (EDC), which activates carboxyl groups to bind amine groups by forming an O-acylisourea intermediate that quickly reacts with an amino group to form an amide bond. O-acylisourea generally undergoes quick hydrolysis. Therefore, to increase the efficiency of coupling, sulfo-N-hydroxysuccinimide (sulfo-NHS) was added to the reaction mixture to generate an amine-reactive sulfo-NHS ester.

BSA was coupled in parallel to the control NDPs.

A detailed description of an exemplary suitable coupling procedure follows:

Two samples of NDP, each containing 2 mg in 1.8 ml of 0.1M MES, 0.5M NaCl, pH 6.0, were prepared. Sample A contained 1 mg Bt per 1 mg NDPs. Sample B contained 1 mg BSA per 1 mg NDPs, and served as a control.

To each sample, 0.72 mg EDC was added and the mixture incubated at room temperature (about 21° C. to 25° C.). with gentle rotating for 15 minutes. After incubation, 2.5 μl of 2-mercaptoethanol (to give a final concentration of 20 mM) was added to quench the EDC and stop the carboxyl group activation.

The activated NDPs were transferred to 1.5 ml centrifuge tubes and centrifuged at 10,000×g for 5 minutes at room temperature. The NDP pellets were washed twice with 1 ml PBS and suspended in coupling buffer (PBS). One milligram of either Bt or BSA in 1 ml of PBS was added to each sample tube. The tubes were incubated for two hours at room temperature with gentle rotating. Ten μl of 1M Hydroxylamine-HCl (350 mg in 5 ml PBS) was added to each tube for quenching (final concentration of Hydroxylamine-HCl should be about 10 mM).

The sample tubes were centrifuged at 10,000×g for 5 minutes at room temperature. The supernatants were saved for protein concentration determination to check coupling efficiency. The NDP-F-Bt particles were washed three times with 1 ml PBS each time. The washed particles were suspended in a volume of PBS to achieve a concentration of 1 mg/ml.

Coupling efficiency was evaluated using immune detection of Bt on the surface of NDPs (NDP-Bt). For ease of reference in this document, the detection method is called semi-ELISA. Broadly speaking, polyclonal antibody against Bt was developed commercially in rabbits (Chemicon/Millipore Inc.) using purified native polypeptide as the antigen. The saturated concentration of Bt was estimated at 1 mg per 1 mg NDPs. A representative plot from three independent experiments is presented in FIG. 10.

An exemplary suitable assay for determining coupling efficiency follows:

Using a 96-well plate having a U-shaped bottom and that has previously been blocked by incubation overnight at 4° C. with 5% BSA in PBS, 200 μl of an NDP-F-Bt or NDP-F-BSA solution (1 mg/ml NDP in PBS) was each applied to a separate well. The plate was centrifuged for 10 minutes at 1,000×g. The supernatant was removed and the plate gently shaken by vortexing to disperse and re-suspend the pellet of NDP-F.

200 μl of 10% goat serum in PBST (PBS+0.05% Tween-20) was added and mixed a few times by intensive aspiration and releasing from a pipet tip. The mixture was incubated for one hour at 37° C. with slow agitation. The mixture was centrifuged as above and washed three times with 200 μl of PBST. After each centrifugation, the pellet was dispersed by vortexing. After the final wash, 100 μl of anti-bitistatin (5 μg/ml in PBST) was added to the wells and incubated for one hour at room temperature. The plate was then washed three times with PBST as described above. To each pellet, 100 μl of a 1:2000 dilution of goat anti-rabbit IgG AP conjugate (from Sigma) in PBST was added to the wells and the mixture incubated for one hour at 37° C. The mixture was centrifuged at 1,000×g for 10 minutes, and the pellet was washed three times with PBST as above.

150 μl of the AP substrate pNPP (from Sigma) was added and color was developed for approximately 30 minutes (until the intensity of the yellow color was visible) at room temperature with gentle agitation. The reaction was blocked by adding 100 μl of 3 M NaOH (this step is optional). The plate was then centrifuged and 100 μl of the supernatant was transferred to a 96-well plate (flat bottom). The absorbance of the supernatant was measured at 405 nm using an ELISA plate reader.

The activity of NDP-Bt was tested using PFR purified from platelets, αIIbβ3 integrin (Millipore Inc.). Two types of assays were applied to confirm the presence of disintegrin on NDP-Bt, including binding of soluble PFR to NDP-F-Bt and adhesion of NDP-F-Bt to fibrinogen receptor immobilized on the surface (plastic or glass). Binding of soluble PFR was determined on the basis of the functional "sandwich" ELISA, which is referred to herein as a functional semi-ELISA. In this case, immune-detection of αIIbβ3 integrin bound to the NDP-Bt was performed using a polyclonal antibody against the αIIβ integrin subunit (purchased from Santa Cruz Inc.).

An exemplary suitable protocol for a functional semi-ELISA for detecting binding of fibrinogen receptor to NDP-F-Bt follows:

Using a 96-well plate having a U-shaped bottom and that has previously been blocked by incubation overnight at 4° C. with 5% BSA in PBS, 200 μl of an NDP-F-Bt or NDP-F-BSA suspension (1 mg/ml NDP in PBS) was each applied to a separate well. The plate was centrifuged for 10 minutes at 1,000×g. The supernatant was removed and the plate gently shaken by vortexing to disperse the pellet of NDP-F. 200 μl of 3% BSA PBST (PBS+0.05% Tween-20) was added and the composition was mixed a few times by intensive aspiration and releasing from a pipet tip. The mixture was incubated for one hour at 37° C. with slow agitation. Alternatively, the blocking step may be performed in a tube before application on the 96-well plate. The mixture was centrifuged as above and washed three times with 200 µl of PBST. After each centrifugation, the pellet was dispersed by vortexing.

Figure 11:
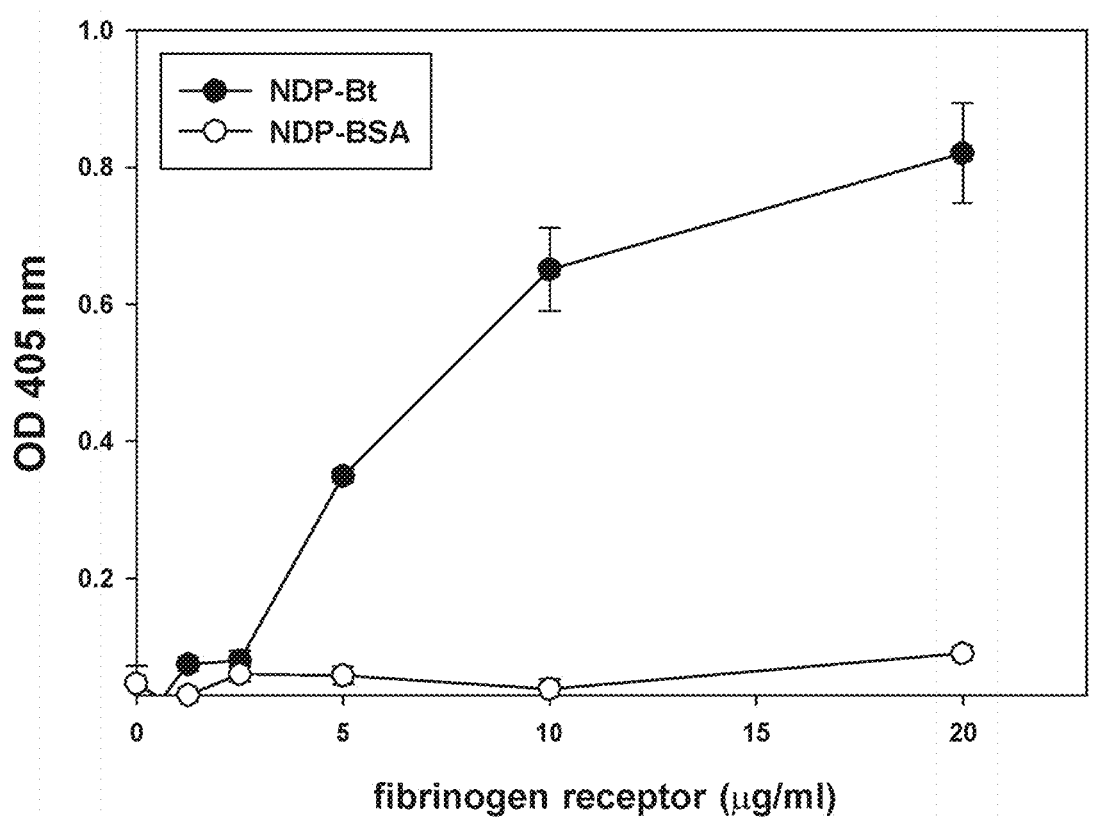
FIG. 11 is a line graph showing interaction of purified integrin with NDPs in semi-ELISA. The experiment was performed using a U-shape bottom 96-well plate. The plate was blocked overnight with 5% BSA, whereas NDPs were blocked with 3% BSA by incubation for 1 hour at 37° C. before application on the plate. Blocked NDPs were added to the wells (0.2 mg per well) and the plate was centrifuged (10,000×g) at room temperature. Platelet Fibrinogen Receptor (PFR) at the indicated concentrations was added in 0.1 ml of Hanks' Balanced Salt Solution (HBSS) containing $Ca^{2+}$ (as $CaCl_2$) and $Mg^{2+}$ (as $MgCl_2$) at physiological concentrations to each well and incubated for 1 hour at 37° C. NDPs were washed three times by centrifugation of the plate (1,000×g) at room temperature and primary polyclonal antibody against the fibrinogen receptor was added (2 µg/ml). Incubation was performed for one hour at 37° C., and samples were washed three times, as described above. Goat anti-rabbit IgG AP conjugated (Sigma Inc.), diluted 1:3000, was added and incubated for one hour as above. Final washing was performed as above and substrate (pNPP) was added to AP. Color was developed for 30 minutes, and NDP samples on the plate were centrifuged at 10,000×g at room temperature to collect the NDP as a pellet. Supernatant was transferred to flat bottom 96-well (0.1 ml) plates and read using an ELISA plate reader at 405 nm wavelength.

Fibrinogen receptor was then added at the desired concentrations (i.e., the amounts required to generate a dose-response); see FIG. 11 (in 200 µl of HBSS containing physiological concentrations of $Ca^{2+}$ and $Mg^{2+}$ and incubated for one hour at 37° C. The plate was then washed three times with PBST as above. Next, 100 µl of anti-fibrinogen receptor (2 µg/ml from Santa Cruz Inc.) polyclonal antibody in PBST was added to the wells and incubated for one hour at room temperature. The plate was washed three times with PBST as above. To the pellets, 100 µl of a 1:3000 dilution of goat anti-rabbit IgG AP conjugate (from Sigma) in PBST was added to the wells and incubated for one hour at 37° C. The mixture was centrifuged at 1,000×g for 10 minutes, and the pellets washed three times with PBST as above.

150 µl of the AP substrate pNPP (from Sigma) was added and color was developed for approximately 30 minutes at room temperature with gentle agitation. The reaction was blocked by adding 100 µl of 3 M NaOH (this step is optional). The plate was centrifuged and 100 µl of supernatant was transferred to the well of a 96-well plate (flat bottom). The absorbance of the supernatant was measured at 405 nm using an ELISA plate reader.

As can be seen from FIG. 11, the PFR bound to the NDP-Bt in a dose-dependent manner, whereas the control NDP-BSA were not active in this assay.

Figure 12:
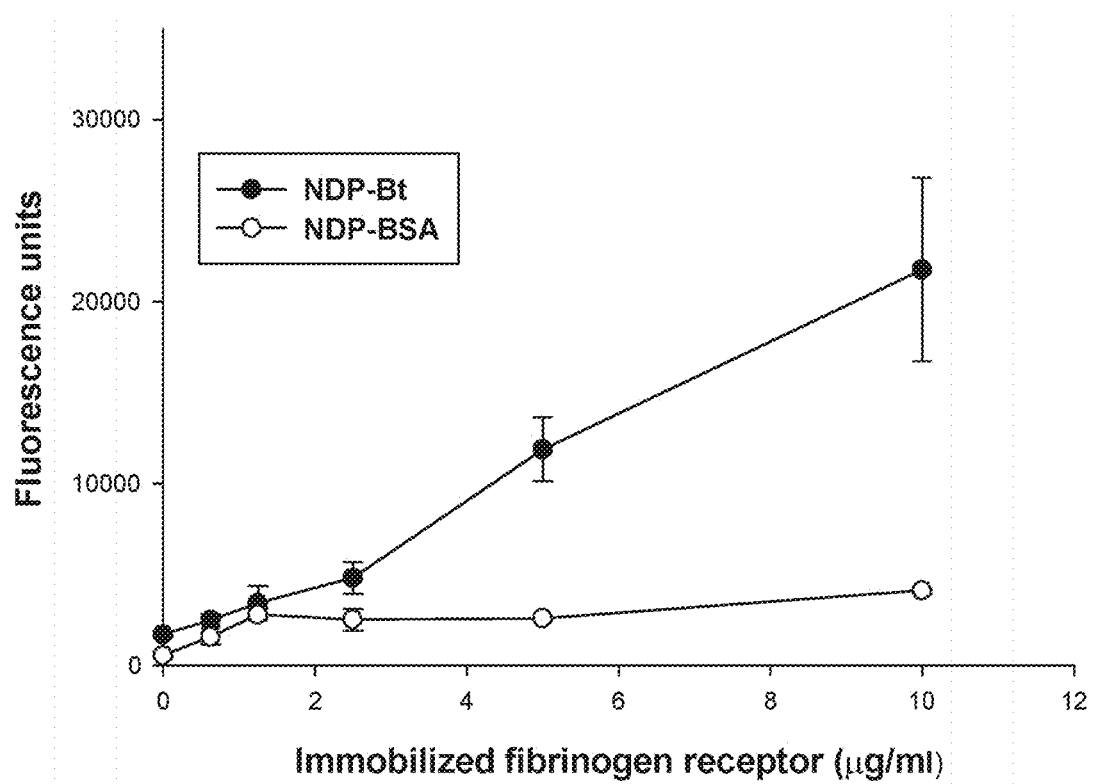
FIG. 12 presents a line graph showing adhesion of NDP-F-Bt and NDP-BSA to immobilized PFR. PFR was immobilized on a 96-well plate by overnight incubation at 4° C. in PBS. The plate and NDPs were blocked with 3% BSA. NDPs coupled to 1 mg protein (Bt or BSA) were used in the experiment. NDPs (300 mg) were added to the wells. Incubation was performed for one hour at 37° C. in HBSS buffer containing calcium and magnesium at physiological concentrations. Unbound NDPs were intensively washed out six times using the same buffer with vacuum aspiration. Finally, HBSS (100 µl) was added to the wells and fluorescence was read using a fluorescence plate reader with 485 nm (excitation) and 530 (emission) wavelengths.
Figure 13:
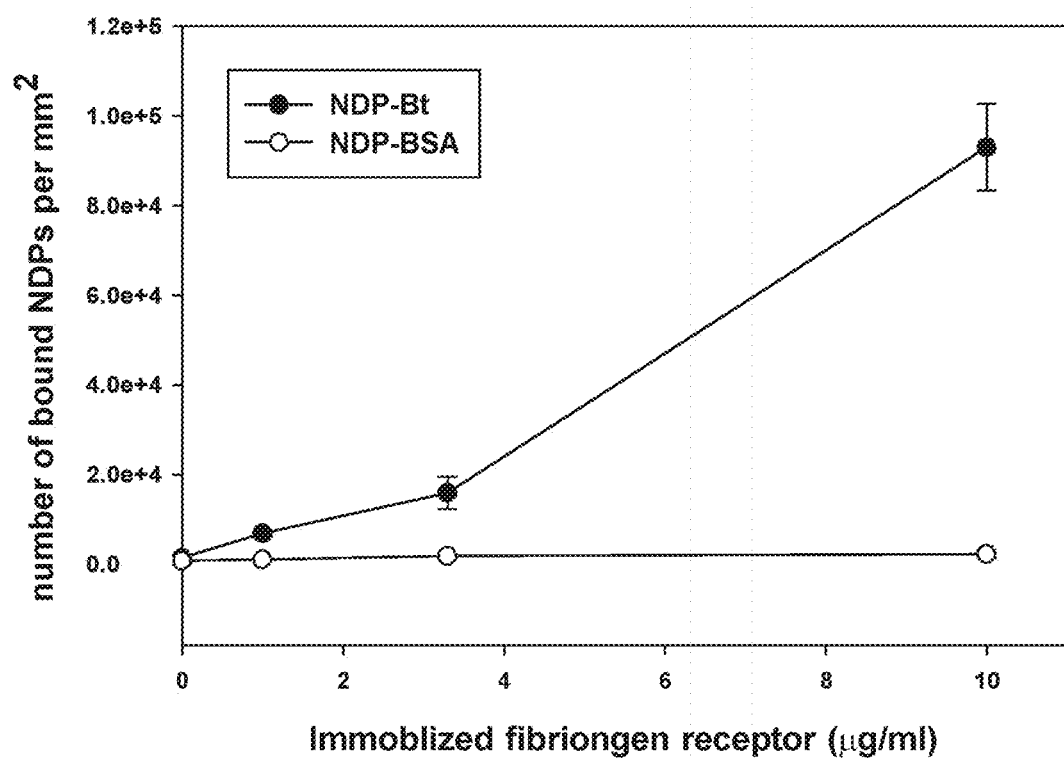
FIG. 13 presents a line graph showing quantitation of adhesion of NDP-F-Bt and NDP-BSA to immobilized fibrinogen receptor. Fibrinogen receptor was immobilized on 8-well glass chamber slides by overnight incubation at 4° C. The wells were blocked with 3% BSA, and NDPs previously also blocked by 3% BSA were added (50 mg per well per 200 ml) in HBSS containing calcium and magnesium at physiological concentrations. The adhesion procedure was performed as per FIG. 12. In the final step, the slide was prepared with mounting buffer (Vector Lab). Images were analyzed under fluorescence microscope (400×) using an oil objective. The numbers of NDPs were calculated using ImageJ software. Error bars represent SD for three independent pictures taken for each concentration of fibrinogen receptor.
Figure 14:
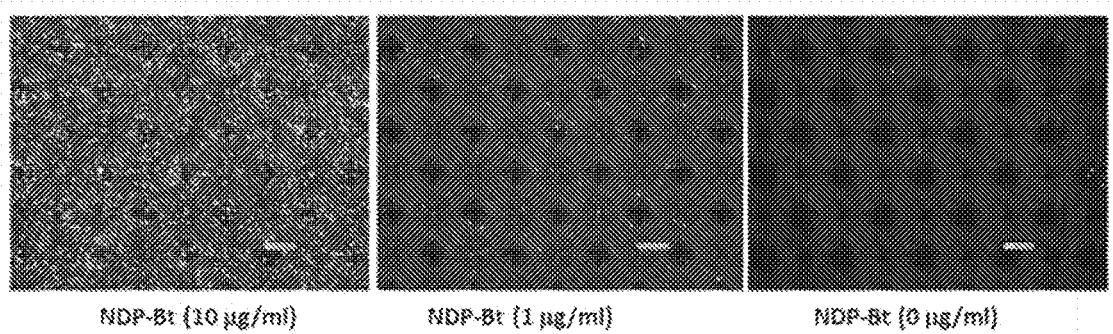
FIG. 14 depicts representative images of adhered NDP-F-Bt to immobilized PFR. PFR (concentrations indicated) was immobilized on an 8-well chamber slide, and the experiment was performed as described in FIG. 13. In the legend, the bars represent 20 µm.

Adhesion of NDP-Bt to immobilized fibrinogen receptor was performed in two formats based on the estimation of the fluorescence of attached NDPs. First, integrin was immobilized on a 96-well plate and adhered NDPs were detected using a fluorescence plate reader. The results obtained showed linear progression of the adhesion of NDP-Bt to increased concentration of immobilized purified receptor (FIG. 12). Adhesion of NDP-Bt was also monitored under fluorescence microscopy. The number of adhered NDPs was quantified using computer software (FIG. 13). Representative images of adhered NDP-Bt are presented in FIG. 14.

Figure 15:
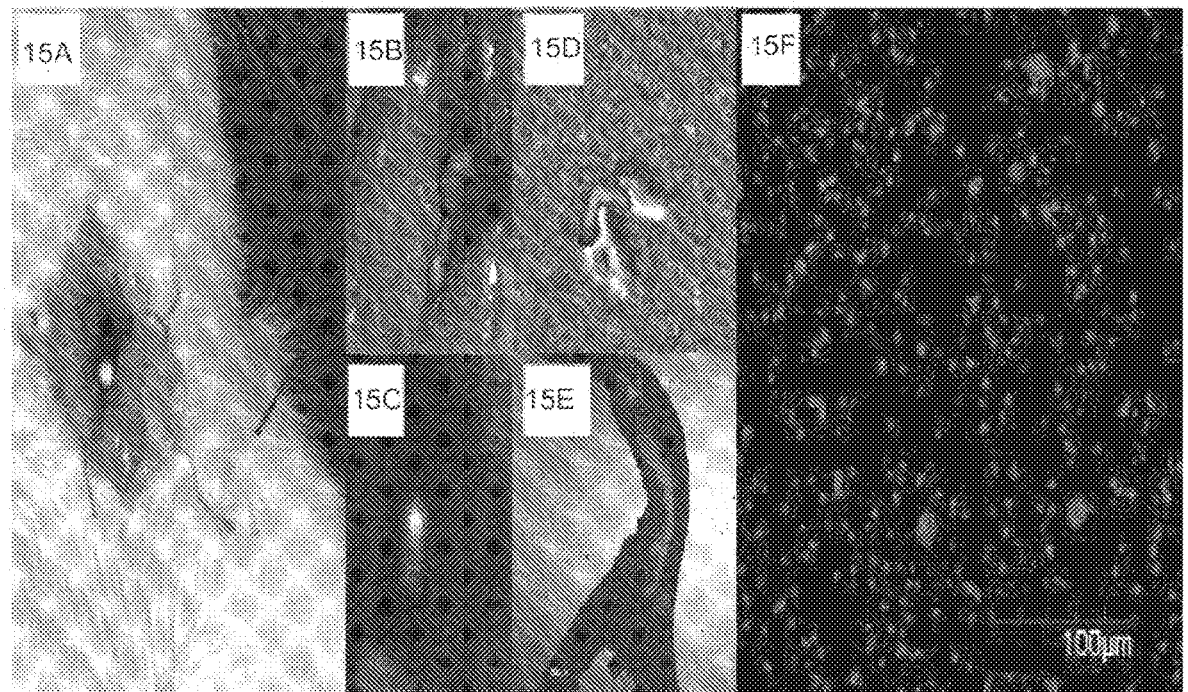
FIG. 15 shows pictures of fluorescent images taken by IVIS and confocal microscopy of carotid artery clots after treatment with FNDP via an external carotid artery infusion.

To further characterize the effects of the FNDP, fluorescent images were taken by IVIS and confocal microscopy of carotid artery clots after treatment with FNDP via external carotid artery infusion. The results are shown in FIG. 15. In two independent experiments, infusion of FNDP via the external carotid artery commenced 3-5 minutes after $FeCl_3$ application and continued over 15 minutes (5 minutes beyond the end of $FeCl_3$ infusion). The FNDP solution consisted of 1.5 ml of PBS where 5 mg/ml of FNDP was suspended (after vortexing of the solution). This route of infusion was selected so as to avoid possible "first pass" elimination of the particles by peripheral organs. Following completion of FNDP infusion, the rat was euthanized and subjected to imaging by IVIS and/or fluorescent microscopy. FIGS. 15A-D show imaging of fluorescence that was performed on an IVIS scanner designed for whole animal imaging using a 580-610 nm excitation and a 695-770 nm emission passband with a 2 second exposure. Auto-fluorescence was subtracted based on excitation at 445-490 nm. FIG. 15A shows an in situ carotid bifurcation region image, indicating fluorescence of carotid arterial clot after treatment visible via IVIS imaging after exposure of the carotid bifurcation zone. FIGS. 15B and 15C are high magnification images of fluorescence emanating from the carotid bifurcation in vivo, suggesting accumulation of FNDP in the clot. FIG. 15D is an ex vivo photograph of fluorescence of carotid artery bifurcation denoting one branch showing fluorescence corresponding to the clot location within the carotid bifurcation. FIGS. 15E and 15F are confocal images taken on an Olympus IX83 of FNDP in which fluorescence is detected at an excitation of 543 nm and an emission of 655-755 nm. Background fluorescence was collected from the same excitation, with emissions of 555-625 nm, and was subtracted from the foreground to reduce auto-fluorescence. FIG. 15E shows ex vivo fluorescence of the carotid artery at 4× magnification. FIG. 15F shows FNDP treated carotid arteries after they were flushed with RIPA lysis buffer and replicates were combined together to form a lysate. Lysate was then deposited onto a cover-glass and imaged at 20× magnification. Large numbers of FNDP at various aggregate sizes around platelets are visible.

Figure 16:
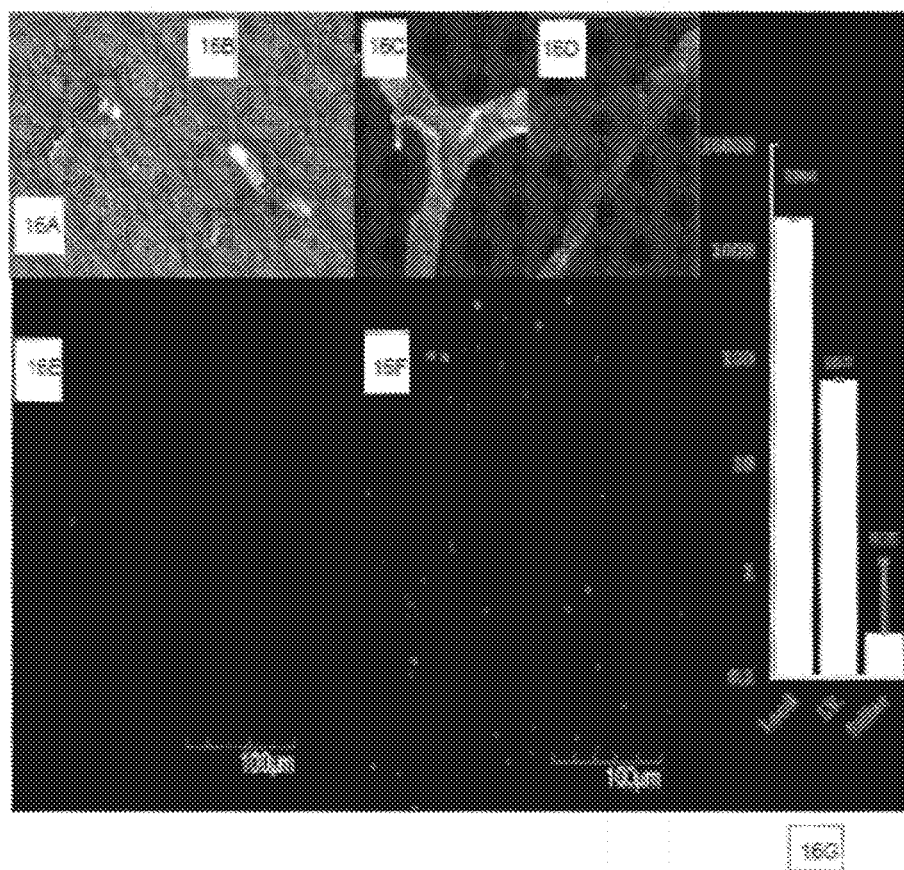
FIG. 16 shows fluorescent images taken by IVIS and confocal microscopy of carotid artery clots after intravenous treatment with FNDP.

FIG. 16 shows fluorescent images taken by IVIS and confocal microscopy of carotid artery clots after intravenous treatment with FNDP. After clot formation by ferric chloride, treatment with saline control or FNDP by intravenous infusion via tail vein or femoral vein was performed in three rats. FNDP were infused (over 10 min) as a suspension in PBS at 1 ml solution containing 1 mg/ml FNDP. Carotid arteries were removed from the animal for imaging and placed in 70% denatured ethanol for preservation until imaging. FNDP were conspicuously identified at the site of clot formation. FNDP were identified in each of the three specimens obtained following intravenous infusion, yet the three specimens were treated together as one for lysate inspection. FIGS. 16A and 16B show imaging of fluorescence as performed on an IVIS scanner designed for whole animal imaging using a 580-610 nm excitation and a 695-770 nm emission passband with a 2 second exposure. Autofluorescence was subtracted based on excitation at 445-490 nm. FIG. 8A shows an ex vivo fluorescent image of a carotid artery from saline-treated control. Auto-fluorescence could not be entirely eliminated, but was evenly distributed across control specimen. FIG. 16B shows an ex vivo fluorescent image of a carotid artery from an IV FNDP-treated animal, showing fluorescence localized to the branch with a clot. FIGS. 16C-16F show confocal images taken on an Olympus IX83. The figures show that FNDP fluorescence was detected at an excitation of 543 nm and an emission of 655-755 nm. Background fluorescence was collected from the same excitation, with emissions of 555-625 nm and was subtracted from the foreground to reduce auto-fluorescence. FIGS. 16C and 16D show ex vivo fluorescence of carotid artery at 4× magnification of saline treated and FNDP treated animals, respectively. Auto-fluorescence could not be entirely eliminated, but was evenly distributed across control specimens, while fluorescence was localized to the branch with clot in the IV treated animal. (See panels 16E and 16F.) Treated carotid arteries were flushed with RIPA lysis buffer and replicates were combined together to form a lysate. Lysate was then deposited onto a cover-glass and imaged at 20× magnification. In order to increase contrast for visual inspection, images were processed with an un-sharp mask in ImageJ.

FIG. 16E shows that the saline-treated control showed no detectable fluorescence. FIG. 16F shows that FNDP appear as frequent fluorescent spots in the treated samples. FIG. 16G presents a graph showing the number of FNDPs present in carotid clot lysates from animals treated locally via the external carotid artery or intravenously as compared with saline treated controls. FNDPs were counted in replicate images after thresholding in ImageJ.

Figure 17A:
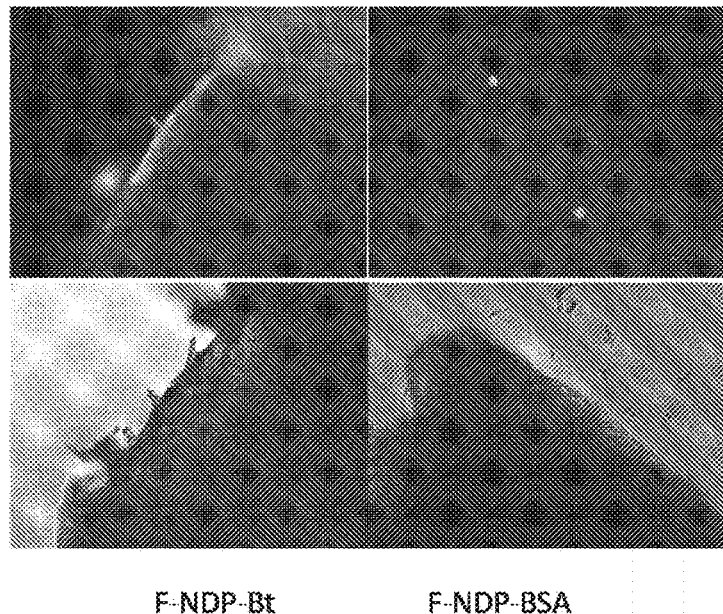
FIGS. 17A-17B show fluorescent microscopy of the specificity of the interaction of F-NDP-Bt for clot generation from rat blood plasma by thrombin (1 U/ml).
Figure 17B:
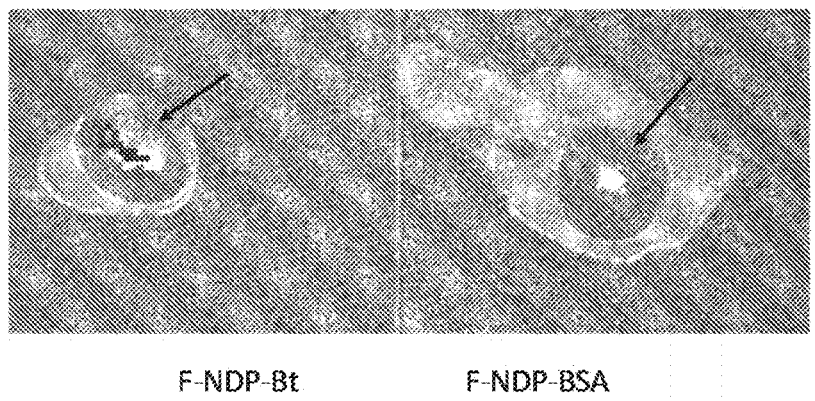

FIG. 17 depicts images of rat blood plasma clots following treatment with F-NDP-Bt and F-NDP-BSA. Rat blood was collected by heart puncture and centrifuged at 100×g for 20 minutes at room temperature to obtain platelet rich plasma (PRP). A thrombus was generated by adding thrombin (1 U/ml) and incubating for 15 minutes at 37° C. The clot that was formed was washed 3× by decanting with HBSS containing calcium and magnesium, and then sliced. Pieces of the clot were incubated with a suspension of F-NDP-Bt and F-NDP-BSA (50 µg/ml) in HBSS containing calcium and magnesium for 60 minutes at 37° C., and washed 3× with the same buffer as above, then applied on the glass slide for imaging. Images of plasma clots obtained from fluorescence microscope Olympus IX81analysis, under 100× magnification, are shown in FIG. 17A. Images of plasma clots obtained using an IVIS 50 imaging system are shown in FIG. 17B. Wavelengths used for measurement: excitation Cy5.5 BkG (580-610 nm), emission Cy5.5 (695-770 nm). For background subtraction: excitation GFP (445-490 nm), emission Cy5.5 (695-770 nm). Exposure time: 1 minute. Arrows in FIG. 17B point the localization of the clot.

FIG. 17 shows the specificity of interaction of F-NDP-Bt with a clot generated from rat blood plasma by thrombin (1 U/ml). Analysis of the clot under a fluorescence microscope (FIG. 17A) revealed that F-NDP-Bt accumulated on the surface of the thrombus to a high extent, although this accumulation was not evenly distributed. Fluorescence microscopy imaging identified areas with high green fluorescence intensity (represented by bright spots in the black and white image), which may indicate zones of the condensation of activated platelets. Fluorescence live imaging system (IVIS 50) also exhibited binding of F-NDP-Bt to the plasma clot (FIG. 17B). However, in this system the near infrared (NIR) detection was set up based on the optimization performed as presented in FIG. 9. Control nanoparticles, containing coupled BSA to the surface (F-NDP-BSA), interacted with the clot to a negligible level in both imaging assays. Detection of F-NDP-Bt by NIR suggested a usefulness of functionally active F-NDP-Bt for imaging in living organisms because the emission wavelength was localized within an "optical therapeutic window" (600-1300 nm).

Therefore, detection of F-NDP-Bt was performed in a rat model for verification of that hypothesis. The results are shown in FIG. 18. The skin areas of observation fields were prepared for implantation by hair shaving. The incision was made by scalpel and vessels were inserted under the skin of dead rats. The dead rats were placed in IVIS 50 Imaging System, and measurement of fluorescence under NIR spectrum was performed. Wavelengths used for measurement: excitation Cy5.5 BkG (580-610 nm), emission Cy5.5 (695-770 nm). For background subtraction: excitation GFP (445-490 nm), emission Cy5.5 (695-770 nm).

Figure 10:
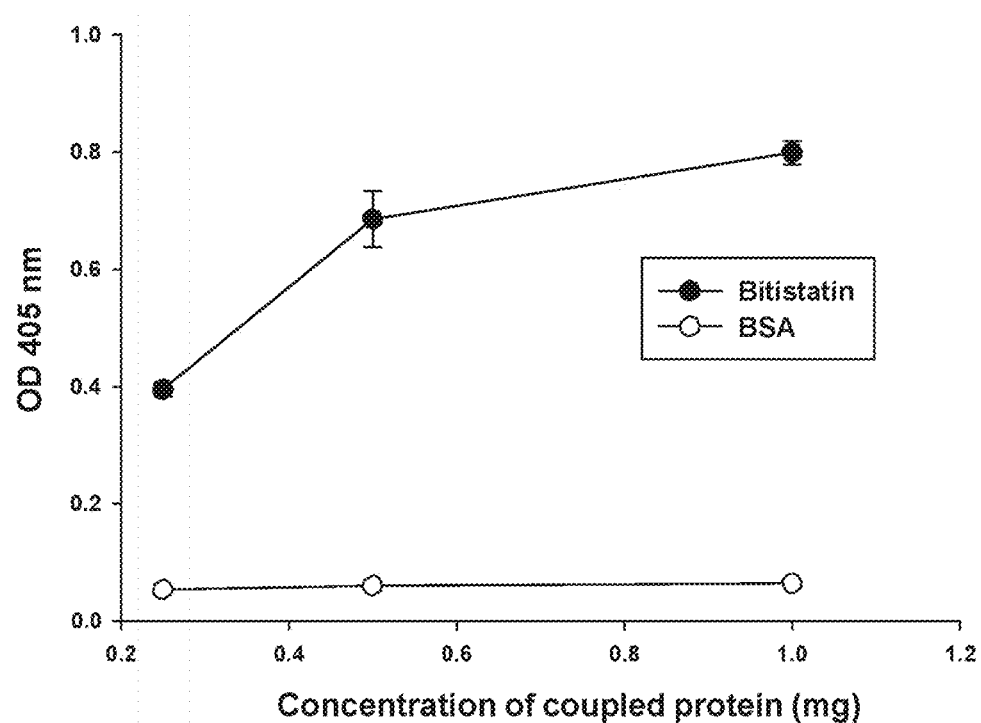
FIG. 10 presents a line graph indicating detection of Bt on NDP-Fs in a "semi-ELISA" assay. NDPs were coupled to Bt or BSA, which were used in concentrations as indicated on the X-axis, per 1 mg of NDP-Fs. 0.2 mg of each NDP sample was used for semi-ELISA in three replicates. The experiment was performed on a 96-well plate (U-shape bottom) with gentle rotation during incubations. NDPs were blocked with 10% goat serum before primary antibody against Bt was added. NDP samples were incubated with anti-Bt antibody for one hour at 37° C., and the plate was washed three times with PBST by centrifugation (1,000×g) at room temperature. Goat anti-rabbit IgG AP conjugated (Sigma Inc.), diluted 1:2000, was added and incubated for one hour as above. Final washing was performed as above and substrate (pNPP) was added to AP. Color was developed for 30 minutes, and NDP samples were centrifuged. The supernatant was transferred to a 96-well plate and read using an ELISA plate reader under 405 nm wavelength. Error bars represent standard deviation (SD) from three independent samples applied for the semi-ELISA procedure.
Figure 18A:
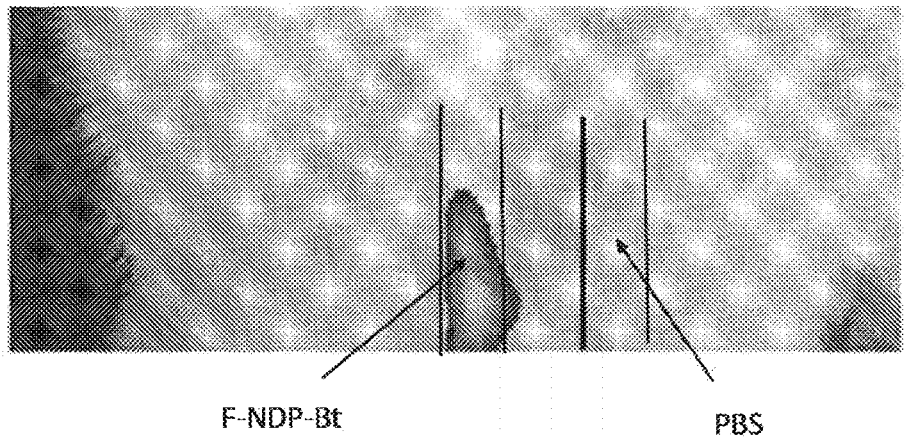
FIGS. 18A-18B show images of vessels filled with F-NDP-Bt implanted subcutaneously in a rat (post-mortem).
Figure 18B:
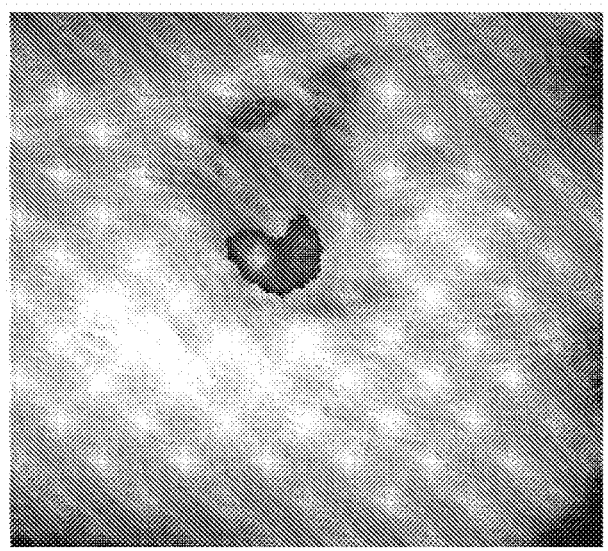
Figure 18C:
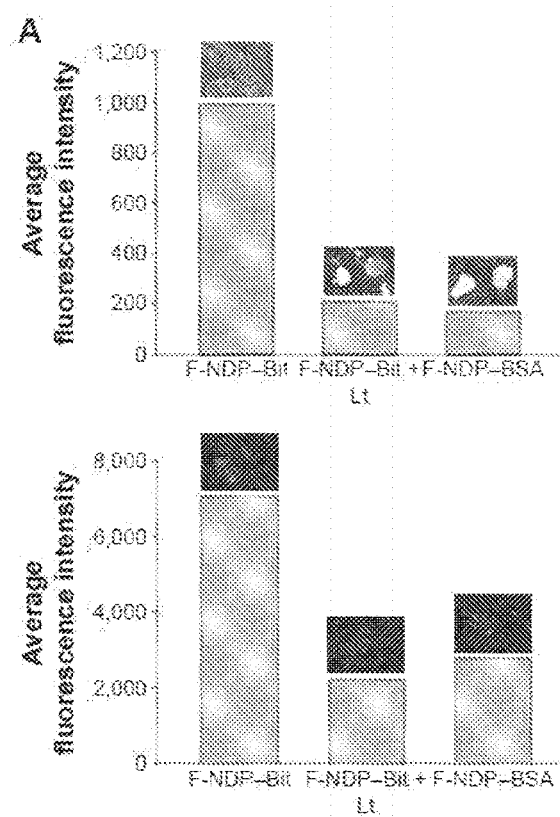
FIG. 18C shows plots of average fluorescence intensity for F-NDP-Bt, F-NDP-Bt+lotrafiban (lt), and F-NDP-BSA in thrombin-induced PRP clots.
Figure 18D:
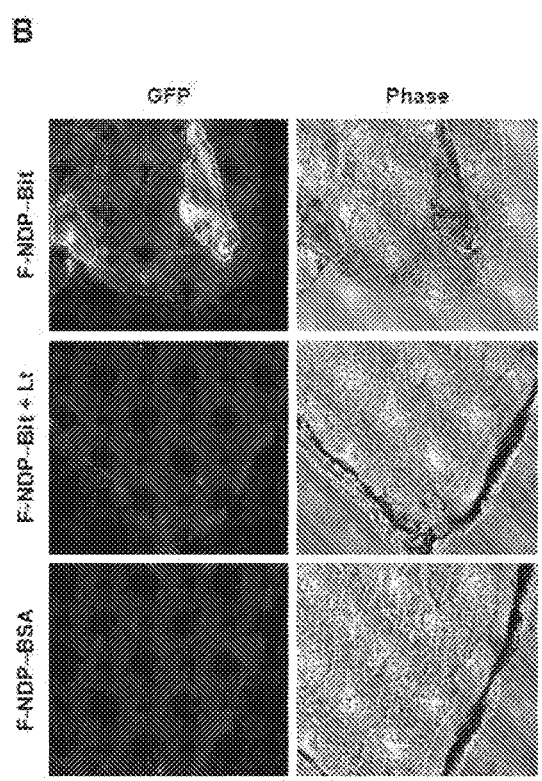
FIG. 18D shows representative images of the clots in FIG. 18C from IVIS.

A representative image of the implanted glass capillaries filled with F-NDP-Bt (4 mg/ml) or PBS (control) are shown in FIG. 18A. Exposure time was 5 seconds. FIG. 10B shows an image of a rat aorta filled with F-NDP-Bt. The rat aorta was dissected from a euthanized female rat, washed with PBS to remove residues of coagulated blood, and filled with 300 µl of F-NDP-Bt suspension (2 mg/ml) in PBS. The aorta was secured from both ends by knots of surgical sutures. Exposure time was 1 minute. FIG. 18A demonstrates NIR imaging of F-NDP-Bt, experimentally implanted under rat skin. Suspensions of F-NDP-Bt were infused into glass capillaries and into dissected rat aorta (FIG. 18B), before subcutaneous implantation. Clear images showed precise localization of both artificial (capillary) and natural (aorta) vessels in the rats.

Finally, the specificity of the interaction of F-NDP—Bit with the fibrinogen receptor present on activated platelets in a preformed PRP clot (FIGS. 18C-18D) was investigated. In two separate experiments, clots were incubated with F-NDP—Bit for 15 or 60 minutes, respectively. A clot was generated from rat PRP by thrombin (1 U/mL) and incubated with F-NDP—Bit (250 µg/mL) in the presence or absence of Lt (4.67 µmol/mL). (FIG. 18C) IVIS imaging was performed using GFP filters (excitation 445-490 nm, emission 515-575 nm). The clot was incubated with F-NDP—Bit for 15 minutes (upper panel) or 60 minutes (lower panel). Intensity of fluorescence was evaluated using IVIS Living Image 4.3.1 software. Insets above the bars represent respective images of clots from IVIS. (FIG. 18D) Phase-contrast and fluorescence microscope images of clots (100×). Areas of accumulation of F-NDP—Bit are framed in yellow. Irrespective of the duration of incubation, binding of F-NDP—Bit was always 4-5 fold higher than that of the nonspecific control particles (F-NDP—BSA). Furthermore, preincubation of the clots with lotrafiban (lt) reduced F-NDP—Bit binding to the level of the control F-NDP—BSA.

Bitistatin was purified from the venom of *Bitis arientans* (Latoxan Serpentarium, Valence, France) using two steps of reverse-phase HPLC. F-NDP, chemically surface-functionalized with carboxyl groups (—COOH), were purchased from Adamas Nanotechnologies (Raleigh. N.C., USA). Two strains of F-NDP were used: green fluorescent F-NDP based on N-V-N color centers (F-NDP(NVN)) at 700 nm ($2\times10^8$ particles/mg) and red fluorescent based on N-V (F-NDP (NV)) color centers at 100 nm ($5\times10^{11}$ particles/mg), 700 nm ($2\times10^8$ particles/mg), and 10,000 nm ($5\times10^5$ particles/mg). Isoflurane was purchased from Henry Schein (B34C16A Dublin, Ohio, USA). 70% Denatured Ethyl Alcohol and PE-10 tubing were purchased from Fisher Scientific (Pittsburgh, Pa., USA). Silk Suture was purchased from Roboz SUT-15-1, Roboz Surgical Instrument Co. (Gaithersburg, Md., USA). Parafilm and $FeCl_3$ was purchased from Sigma-Aldrich, (St. Louis, Mo., USA).

Bitistatin was coupled to the F-NDP of all types using EDC (1-ethyl-3-[3 dimethylaminopropyl] carbodiimide hydrochloride) as a hetero-bifunctional cross-linker. Coupling efficiency and preservation of Bitistatin activity on the various functionalized nanodiamond particles (F-NDP—Bit) were verified using a semi-ELISA methodology.

Example 6

The following example demonstrates the use of functionalized fluorescent nanodiamond particles (e.g., (F-NDP-Bt)) to bind to platelets and preferentially to activated platelets from humans. The data also shows that the particles do not substantially interfere with platelet aggregation.

Figure 19A:
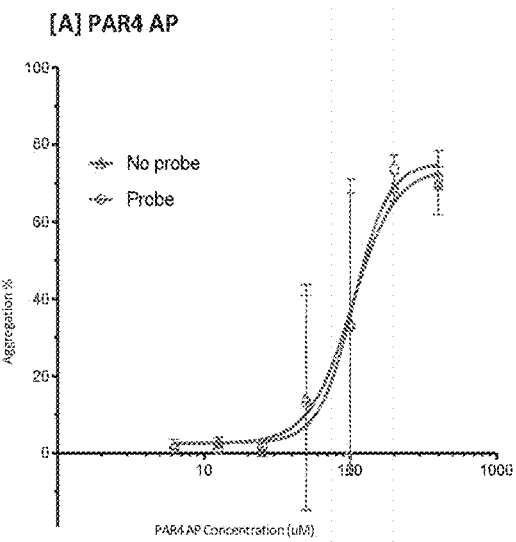
FIGS. 19A-19C show dose response curves with and without 700 nm diameter fluorescent nanodiamond particles functionalized with bitistatin (i.e. probe) for mean maximum platelet aggregation +/− standard deviation linear regression lines for proteinase-activated receptor 4 (PAR4 AP, FIG. 19A), adenosine diphosphate (ADP, FIG. 19B), and arachidonic acid (AA, FIG. 19C).
Figure 19B:
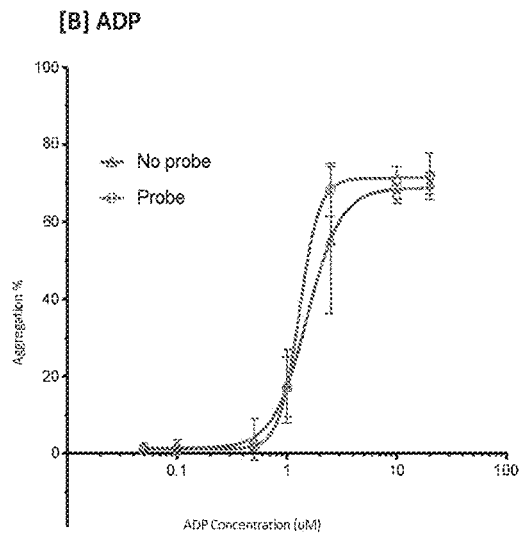
Figure 19C:
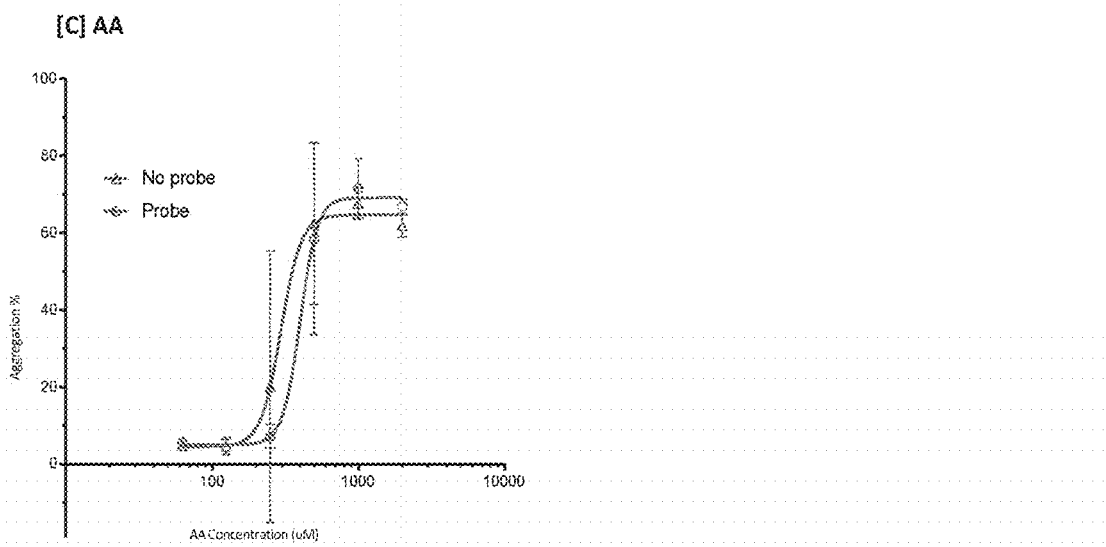

For example, FIGS. 19A-19C show dose response curves for aggregation of platelets with and without probe (i.e., F-NDP-Bt), determined as a function of concentration of proteinase-activated receptor 4 (PAR4 AP), adenosine diphosphate (ADP), and arachidonic acid (AA).

Figure 20A:
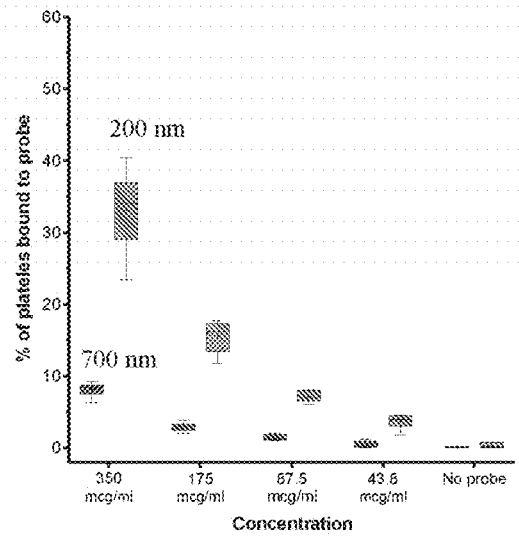
FIGS. 20A-20C show box plots of 700 nm and 200 nm diameter probes binding to platelet populations at various concentrations.
Figure 20B:
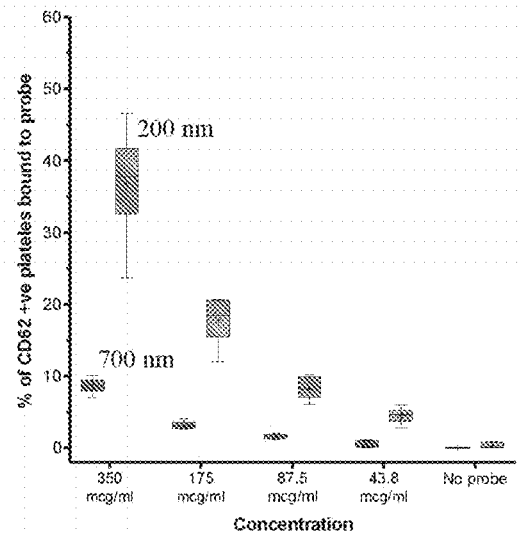
Figure 20C:
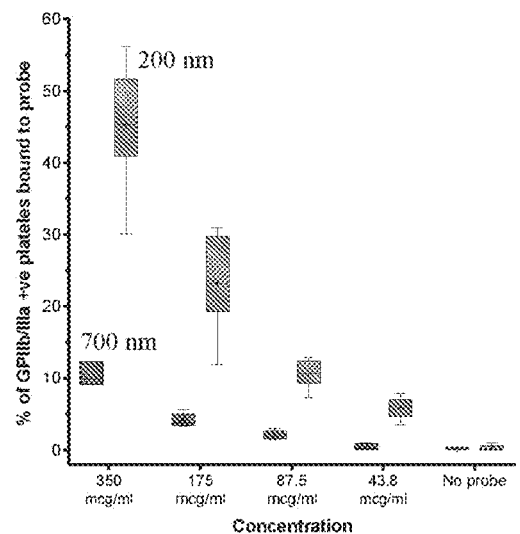
Figure 21:
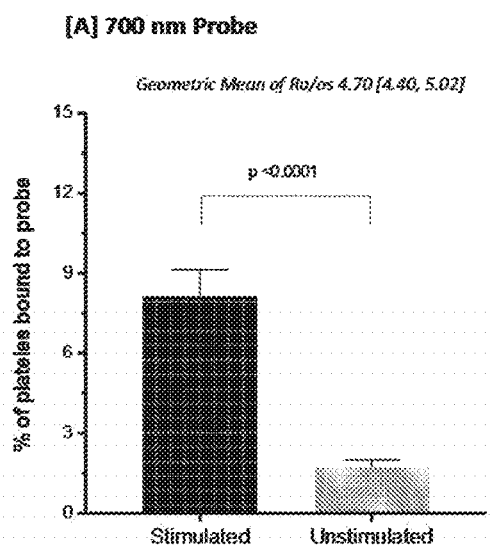
FIG. 21 shows a plot of percentage of platelets bound to 700 nm diameter probes for stimulated versus unstimulated platelet populations. Data shown are mean percentage (+/− standard deviation) of all platelets bound to the probe in simulated versus unsimulated platelets at a concentration of 350 mcg/mL of probe.
Figure 22:
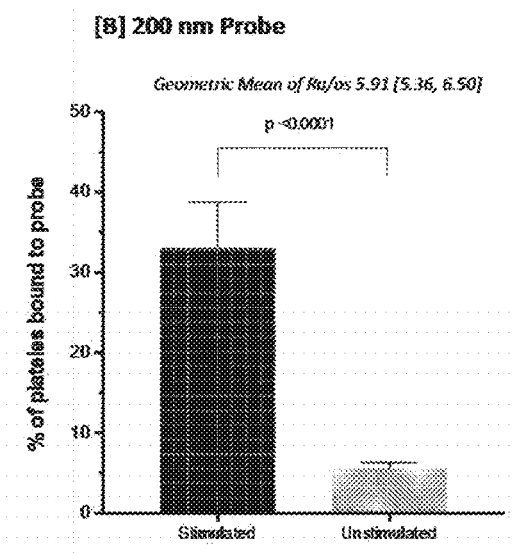
FIG. 22 shows a plot of percentage of platelets bound to 200 nm diameter probes for stimulated versus unstimulated platelet populations. Data shown are mean percentage (+/− standard deviation) of all platelets bound to the probe in simulated versus unsimulated platelets at a concentration of 350 mcg/mL of probe.
Figure 23A:
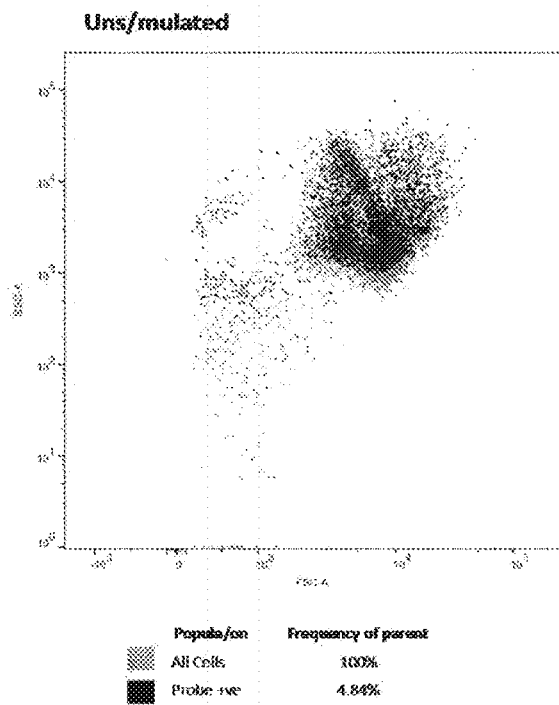
FIGS. 23A-23D show flow cytometry dotplots for unsimulated and simulated populations of cells and platelets.
Figure 23B:
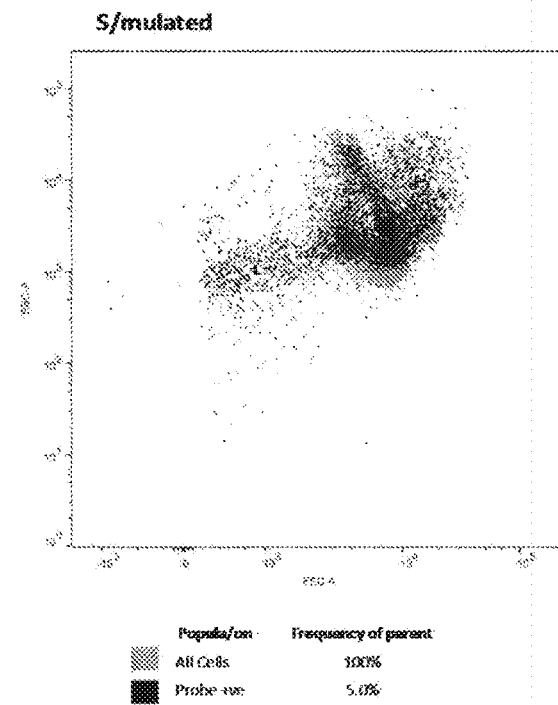
Figure 23C:
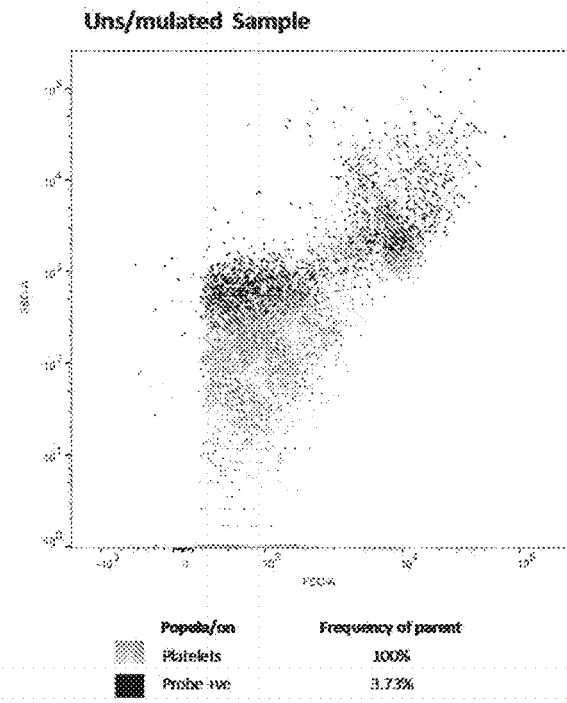
Figure 23D:
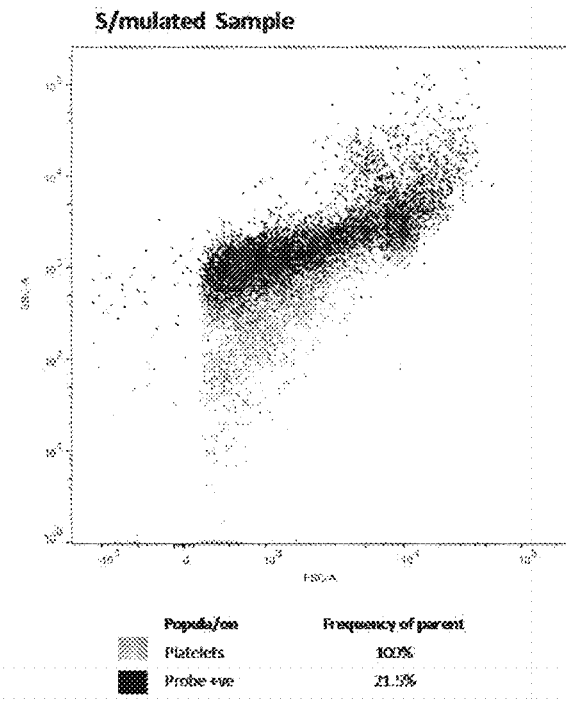
Figure 24A:
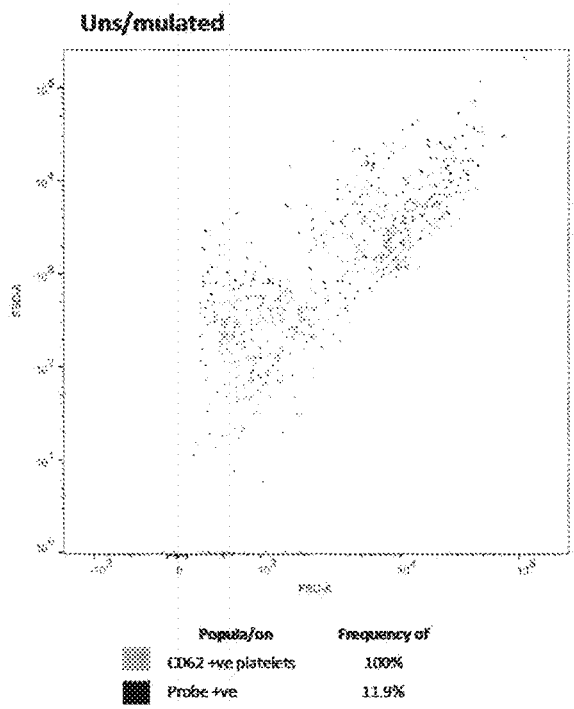
FIGS. 24A-24D show flow cytometry dotplots for unsimulated and simulated populations of cells and platelets.
Figure 24B:
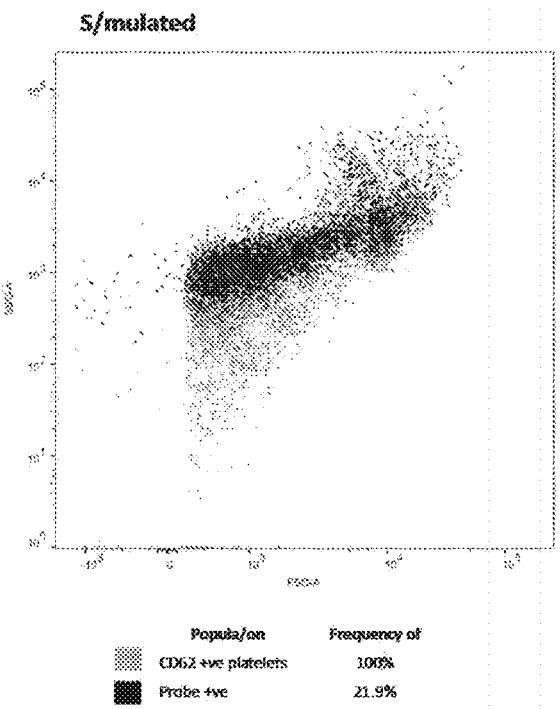
Figure 24C:
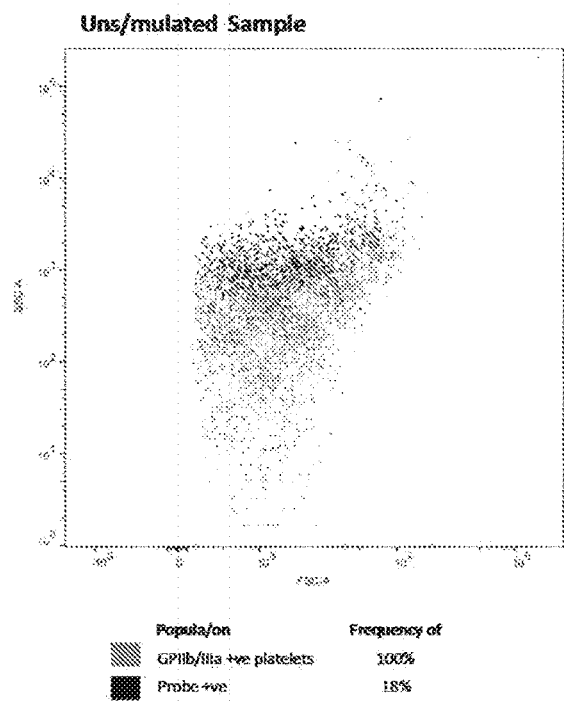
Figure 24D:
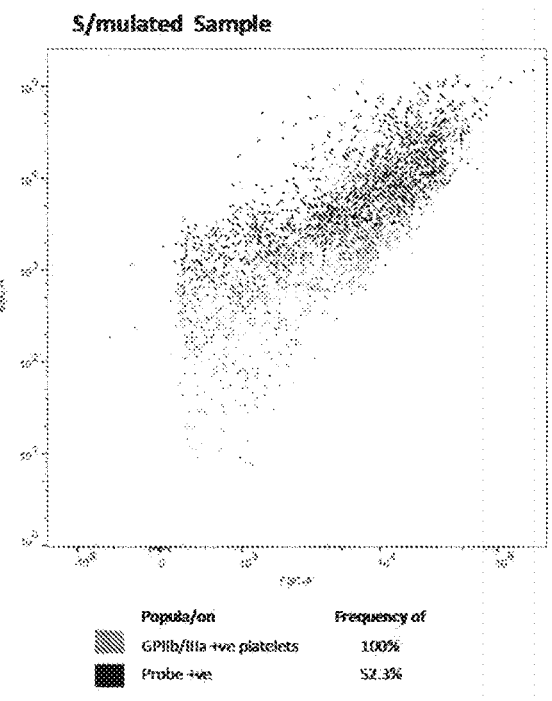

FIGS. 20A-20C show the ability of a F-NDP-Bt probe having an average particle diameter of 700 nm or 200 nm to bind to various platelet populations at different concentrations. FIGS. 21-222 shows the difference in binding of probes (700 nm or 200 nm in diameter) in stimulated versus unstimulated platelet populations.

Flow cytometry data of stimulated and unstimulated platelets are shown in FIGS. 23A-23D and FIGS. 24A-24D, using the F-NDP-Bt probes.

Example 7

The following example demonstrates an exemplary method for extracting, isolating, and/or quantifying F-NDP-(NV) in blood and/or biological tissues.

1. F-NDP-BSA NV 700 nm were prepared using a coupling protocol as described herein, in sterile conditions (see e.g., Example 8). Final concentrations of 5 mg/ml were be prepared in PBS for animal administration.

2. 4 doses of 1 ml (5 mg/ml in PBS) of F-NDP-BSA were injected per one subject (e.g., an animal). Blood (TBD) may be collected into 3.8% sodium citrate (in ratio 1:9) at different time intervals. Control group may be infused with equal volume of normal saline. Blood from PBS-injected animal may be collected in the same way treated samples were processed. At the conclusion of the protocol approximately 10 mL of blood may be collected.

3. Blood containing F-NDP-BSA may be lyophilized using SpeedVac system (SC110A Plus, Thermo Savant) with 4,680×g. Control animal may be used for preparation of standard curve. Standard curve may be prepared by mixing known amount of F-NDP-BSA with blood. 8 serial dilution will be prepared starting from the highest, 2 mg/ml particles density.

4. Dry mass of particles containing blood collected in the course of the experiment of may be dissolved in 12 N HCl at same volume staring volume of blood (approx. 1 ml). Solubilization may be performed by overnight incubation at 60° C.

5. Supernatant may be removed by centrifugation (17,000×g for 5 min at room temperature) and pellet re-suspended in the same volume original volume (e.g., water 1 ml). Centrifugation will be repeated one time for washing. At this point, particles may be condensed using smaller amount of water, to improve sensitivity. For example, final volume of water may be twice lower than volume of blood used for lyophilization, e.g., such that sensitivity for detection of F-NDP would be twice increased.

6. Suspension of F-NDP-BSA of investigated samples and standard curve may be applied on 96-well plate (100 microliters per well) and plate may be read in Tecan using NIR wavelength (excitation 570 nm, emission 670 nm). In parallel, number of particles per ml may be established by disposable hemocytometer (Incyto Inc., Cheonan-si, Korea), counting under fluorescence microscope, e.g., using an Olympus IX81 with TRICI wavelength and 400× magnification. Amount of F-NDP-BSA in investigated samples may be deducted from the standard curve.

Example 8

The following example demonstrates an exemplary method for sterilization and/or lyophilization of F-NDPs.

1. F-NDPs were suspended in 70% ethanol and incubate for 15 min at room temperature (23+/−2° C.), using gentle agitation on "Speci Mix Test Tube Rocker" (ThermoScientific Inc., Waltham, Mass. USA). Density of F-NDPs was approximately 0.5 mg/ml.

2. The suspension of F-NDPs may be centrifuged (e.g., 17,000×g for 5 min at room temperature). Supernatant (ethanol) may be removed by vacuum aspiration and pellet suspended in water or buffer (e.g., PBS or MES) and centrifuged once again under the same speed conditions for washing purposes.

3. F-NDPs were suspended in water or working buffer (e.g., MES if coupling to protein will be performed) in desired density (e.g. 1 mg/ml).

4. Lyophilization of F-NDPs may be performed using a SpeedVac system (SC110A Plus, Thermo Savant, and Holbrook, N.Y., USA). For example, polypropylene tubes 5 ml (Sarstedt Inc., Numbrecht, Germany) or 1.5 ml (Fisher Inc. Waltham, Mass. USA) were used for lyophilization. This system generally operates with concentrator set up for working in ambient temperature giving low drying rates. For example, application of high drying rates and work in a range of, for example, 43° C.-65° C. temperature may be harmful for some polypeptides and/or polynucleotides attached to the F-NDP. Concentrator may be used with 8,500 rpm maximal speed giving 4,680×g maximal force. Vacuum pump (model VLP120, Thermo Savant), may be set up for gas-ballast control "closed" position giving ultimate total pressure 1.5×10-3 Torr. Refrigerated vapor trap (model RVT400, Thermo Savant) may be used with 4 liter chamber capacity giving, approximate operating temperature −50° C.

Lyophilization may be performed from water or buffer suspension dependent on required purposes (e.g. PBS may be used for in vivo application for diagnostic approaches such as thromboembolic events in vasculature). Reconstitution of F-NDP may be performed using sterile deionized water, to the desired volume. All procedures may be performed in sterile conditions including all materials such as tubes and tips.

Figure 25A:
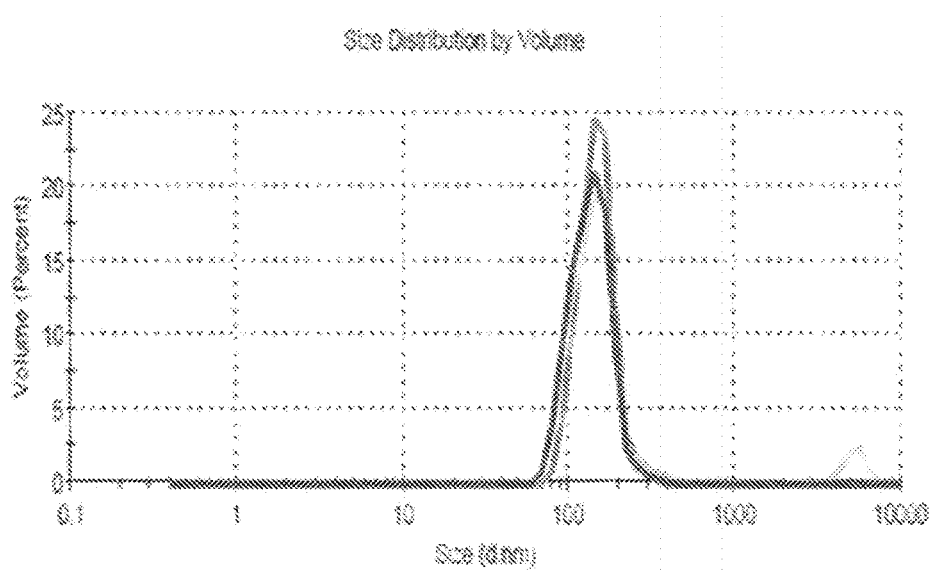
FIGS. 25A-25B show plots of volume versus size (FIG. 25A) and fluorescence intensity versus size (FIG. 25B) for F-NDPs before and after sterilization.
Figure 25B:
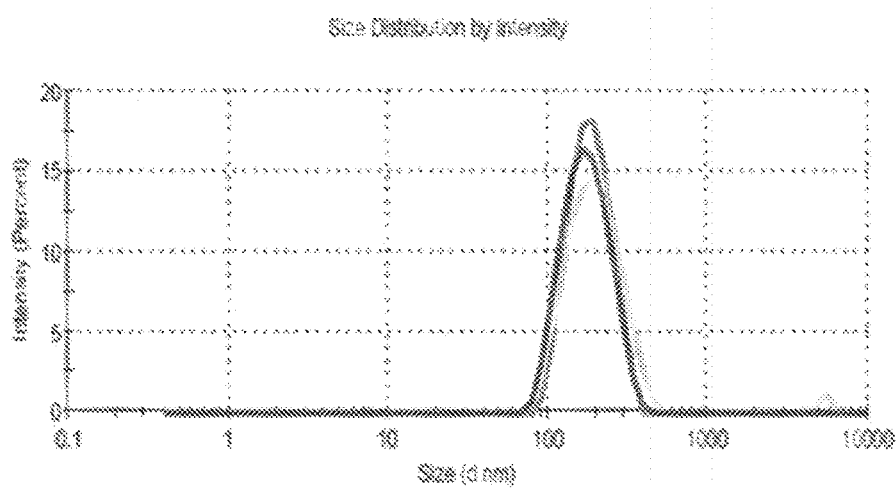

4. Measuring the effect of ethanol sterilization and lyophilization on size distribution may be performed using Zetasizer Nano ZS (Malvern Instruments Ltd., Westborough, Mass., USA). Working density of F-NDPs was estimated as 10 mg/ml. FIGS. 25A-25B show a high overlap of same F-NDPs for Particles Size Distribution (Malvern, PSD) assayed before and after sterilization.

Example 9

The following example demonstrates the ability of fluorescent-NanoDiamond particles (F-NDP) covalently conjugated with bitistatin (F-NDP—Bit) to detect vascular blood clots in vivo using extracorporeal near infrared (NIR) imaging. Specifically, NIR fluorescence properties of F-NDP were compared with color centers (NV vs. NVN) and sizes (100-10,000 nm). Optimal NIR fluorescence and tissue penetration across biological tissues (rat skin, porcine axillary veins and skin) was obtained for F-NDP(NV) with a mean diameter of 700 nm. Interavital imaging (IVIS) in vitro revealed that F-NDP(NV)—loaded glass capillaries could be detected across 6 mm of rat red-muscle barrier and 12 mm porcine skin, which to average vertical distance of a human carotid artery bifurcation from the surface of the adjacent skin (14 mm). In vivo, feasibility was demonstrated a rat model of $FeCl_3$-generated occlusive blood clots I carotid artery bifurcation. Following systemic infusions of F-NDP(NV)-Bit (3 or 15 mg/Kg) via the external carotid artery (ECA) or femoral vein (N=3), presence of the particles in the thrombi was confirmed both in situ via IVIS, and ex vivo, via confocal imaging. F-NDP(NV) presence in the vascular clots was further confirmed by direct counting of fluorescence particles extracted from clots following tissue solubilization. The data suggests that F-NDP(NV)-Bit associate with vascular blood clots, presumably by F-NDP(NV)-Bit binding to activated platelets within the blood clot. It is posited that F-NDP(NV)-Bit could serve as non-invasive platform technology for identification of vascular thrombi using NIR energy monitored by an extra-corporeal device.

Materials

Bitistatin was purified from the venom of *Bitis arientans* (Latoxan Serpentarium, Valence, France) using two steps of reverse-phase HPLC, as described above. F-NDP, chemically surface-functionalized with carboxyl groups (—COOH), were purchased from Adamas Nanotechnologies (Raleigh. N.C., USA). Two strains of F-NDP were used: green fluorescent F-NDP based on N-V-N color centers (F-NDP(NVN)) at 700 nm (2×108 particles/mg) and red fluorescent based on N-V (F-NDP(NV)) color centers at 100 nm (5×1011 particles/mg), 700 nm (2×108 particles/mg), and 10,000 nm (5×105 particles/mg). Isoflurane was purchased from Henry Schein (B34C16A Dublin, Ohio, USA). 70% Denatured Ethyl Alcohol and PE-10 tubing were purchased from Fisher Scientific (Pittsburgh, Pa., USA). 5-0 Silk Suture was purchased from Roboz SUT-15-1, Roboz Surgical Instrument Co. (Gaithersburg, Md., USA). Parafilm and FeCl3 was purchased from Sigma-Aldrich, (St. Louis, Mo., USA).

Coupling of Bitistatin to F-NDP

Bitistatin was coupled to the F-NDP of all types using EDC (1-ethyl-3-[3 dimethylaminopropyl] carbodiimide hydrochloride) as a hetero-bifunctional cross-linker. Coupling efficiency and preservation of Bitistatin activity on the various functionalized nanodiamond particles (F-NDP—Bit) were verified using a semi-ELISA methodology.

Characterization of NIR Emission of F-NDP(NV) and F-NDP(NVN)

NIR fluorescence profiles of F-NDP were characterized using a Tecan Infinite 200 PRO (Tecan AG, Mannedorf, CH). 100 μl of 3 mg/ml of 700 nm F-NDP(NV) or F-NDP(NVN) suspended in de-ionized (DI) water were loaded into 96-well polystyrene. Fluorescence was scanned for all wells with excitations from 230 nm-850 nm and emissions from 290 nm-850 nm (FIG. 1A) at 20 nm intervals. Data was processed in Matlab 2015b (Mathworks, Natick, Mass., USA). Background fluorescence was subtracted from empty wells without F-NDP and the resulting net fluorescence value was Log 10 transformed for visualization.

Glass capillaries (40 mm length, 1 mm internal diameter, (Thermo Fisher Scientific, Waltham, Mass., USA) were filled with equal volumes (30 microliters) of suspensions of F-NDP at concentrations from 0.06 and up to 4 mg/ml (1.8-120 μg total particle mass) and sealed at each end by plasticine (Hasbro, Pawtucket, R.I., USA). The NIR fluorescence intensity of the various suspensions in the capillaries were analyzed using an IVIS 50 Imaging System (PerkinElmer Inc., Akron Ohio) using an excitation filter set to 'Cy5.5 BkG' (580-610 nm) and an emission filter set to 'Cy5.5' (695-770 nm) as these filters matched the desired NIR emission profile detected as described above. Imaging was completed with 'binning' set to 4, and a 10 cm field of view, with exposure times between 2 and 40 seconds. For imaging through biological barriers (rat and porcine skins and rat muscles) auto-fluorescence was imaged with the blue-shifted excitation 'GFP' (445-490 nm) and the same emission filter 'Cy5.5' (695-770 nm) with similar imaging settings as above and subtracted from the foreground as modified from IVIS 50 protocol to compensate for the large stokes shift of the F-NDP(NV).12 This correction was used for a simplified spectral un-mixing: A ratio of auto-fluorescence between the channel of interest and blue-shifted excitation channel is defined in control tissue. The same ratio was then used to subtract auto-fluorescence from the channel of interest based on the blue-shifted excitation channel in the test specimen. This operates under the assumption that the fluorophore being detected may have minimal excitation at the blue-shifted wavelength. To assess tissue penetration of NIR florescence emission from F-NDP, capillaries were placed under shaved abdominal rat skin (obtained from euthanized rats), covered with dissected rat quadriceps muscle (2-5.9 mm thick), or covered with porcine skin (isolated from shoulder of pig obtained from a local butcher shop)

Generation of Carotid Arterial Blood Clot and F-NDP Infusion in Rat

Technical procedures of the $FeCl_3$-induced vascular thrombosis model are generally known in the art. Specific modifications used in this particular work are briefly summarized below. All animal procedures were performed according to the guidelines of the US Animal Welfare Act and approved by the Institutional Animal Care & Use Committee at SUNY Downstate Medical Center. In brief: adult male Sprague-Dawley rats (Charles River, 350 Gm +/−10% body weight), were anesthetized using 4% isoflurane (IF, induction, in chamber) followed by 1-2% IF (maintenance) adjusted throughout the procedure. Rats were held in the supine position and subjected to surgery using clean instruments and aided by binoculars. The left carotid artery was dissected and exposed at the bifurcation region. A 5-0 surgical silk suture was wrapped below the common carotid (CCA), external carotid (ECA), and internal carotid (ICA) arteries. A PE-10 cannula was then inserted in the ECA for studies where F-NDP(NV)-Bit were injected locally. A PE-10 cannula was also inserted into the left femoral vein for studies where F-NDP(NV)-Bit was infused intravenously (IV). The ICA stem was wrapped in Parafilm soaked in 50% $FeCl_3$ and kept in place for 10 minutes. Two to three minutes after placing the Parafilm onto the ICA, infusion of F-NDP(NV)-Bit suspension in PBS commenced either via the ECA (N=2, 15 mg/Kg in 1 mL), or via the femoral vein (N=6) at low dose (N=3, 3 mg/Kg in 1 mL PBS), or at high dose (N=3, 45 mg/Kg in 3 mL PBS). All infusions were completed over 10 minutes. Control rats were infused with vehicle at comparable volumes and duration.

Tissue Fixation Post F-NDP(NV)-Bit Infusion

Following the completion of particles infusion, anesthesia was augmented to produce deep hypnosis using 5% IF. The lower aorta was quickly isolated and cut to allow blood drainage. Tissue was fixed and residual blood removed by perfusion with 10 mL of 70% denatured ethanol. Dissection of both bilateral carotid artery bifurcation regions was completed after whole body imaging (IVIS). Vessels were suspended 70% denatured ethanol for further ex vivo NIR fluorescence evaluation.

In Situ and Ex Vivo Imaging of F-NDP(NV) Fluorescence by IVIS

Briefly, NIR fluorescence was detected using a 580-610 nm excitation and a 695-770 nm emission pass-band with 2 second exposure, 'binning' set to 4, and a 7 cm field of view as described above. Auto-fluorescence was subtracted based on excitation at 445-490 nm under otherwise similar imaging conditions. Carotid arteries were exposed before imaging to enable clear visualization for in situ images. Following in situ imaging, carotid arterial bifurcations were removed from animals and placed on a glass plate for imaging ex vivo using identical imaging parameters to those used for in situ imaging. For each artery, the mean fluorescence intensity of the images compensated for auto-fluorescence was calculated using ImageJ (NIH, Bethesda, Md., USA).

Ex Vivo Imaging of F-NDP(NV) by Fluorescence Microscopy

Gross images of the entire carotid bifurcation region extracted from clot bearing or contralateral vessels were evaluated on a Fluoview FV1000 (Olympus, Tokyo, Japan) laser scanning confocal microscope (LSCM) using a 4× objective. NIR fluorescence emitted from F-NDP(NV) was detected at an excitation of 543 nm and an emission of 655-755 nm. Confocal stacks were combined using a maximum intensity projection so that the entire vessel is brought into focus. The mean fluorescence intensity of F-NDP in each artery was calculated after subtraction of the local background using ImageJ.

Isolation of F-NDP(NV) from Vascular Clot

F-NDP were isolated from extracted carotid arteries by homogenization in RIPA lysis buffer (Teknova Inc. Hollister, Calif., USA) at 100 mg/ml. Aliquots (10 microliters) of the lysate suspension were applied on the microscope slides and analyzed under LSCM as above under 20× objective.

In animals treated with F-NDP(NV) via the femoral artery at high dose, F-NDP(NV) were isolated from extracted carotid arteries by solubilizing the clot bearing vessel segment in 12 N hydrochloric acid (HCl) (Thermo Fisher Scientific, Waltham, Mass., USA) overnight at 60° C. at 100 mg/ml. The solution was centrifuged (14,000×g at room temperature for 10 minutes) and the pellet was washed 1× with distilled water. The pellet containing the insoluble F-NDP(NV)-Bit was re-suspended in DI-water while keeping the initial mass/volume ratio. An aliquot of the suspension was applied to a hemocytometer (Incyto Inc., Cheonan-si, Korea), which was standardized for particles counting in an inverted fluorescence microscope (Olympus IX81) with 40× objective. Images of F-NDP(NV)-Bit were taken from each observation field for counting using TRITC filter cube. Numbers of particles were calculated for the entire solubilized tissue.

Statistical Analysis

Unless stated otherwise, each experiment in this example was performed independently three times in triplicate. No outlying data was excluded. Data are represented as mean±SD. Statistical analyses were done by the Student's t test using (SigmaPlot® 12 SPSS, Systat Software Inc., San Jose Calif., USA). $P<0.05$ was considered significant.

Results

Figures 26A, 26B, 26C:
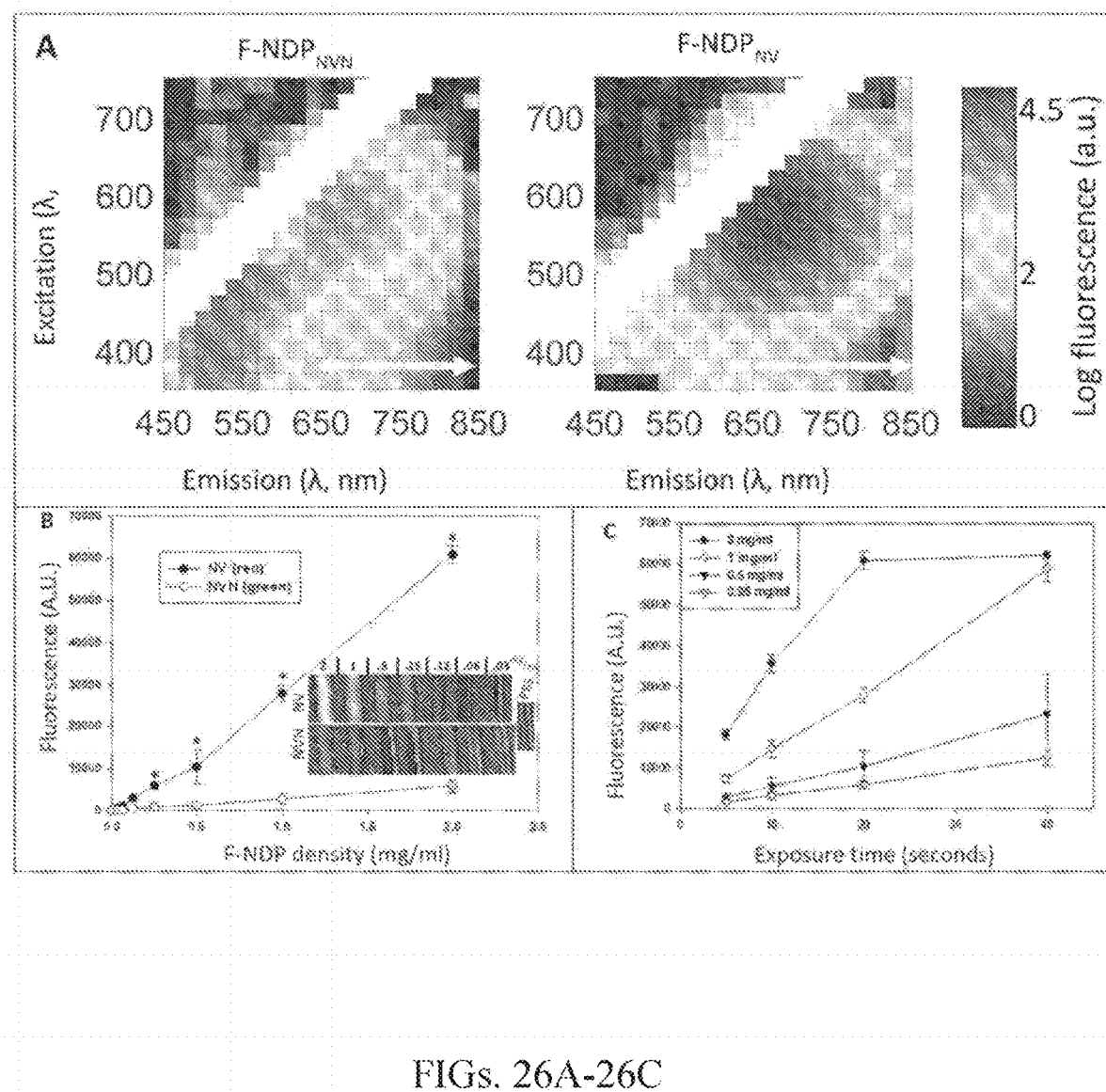
FIGS. 26A-26C show a comparison of NIR fluorescence intensity of F-NDP(NV) and F-NDP(NVN) in suspensions.
Figures 27A, 27B, 27C, 27D:
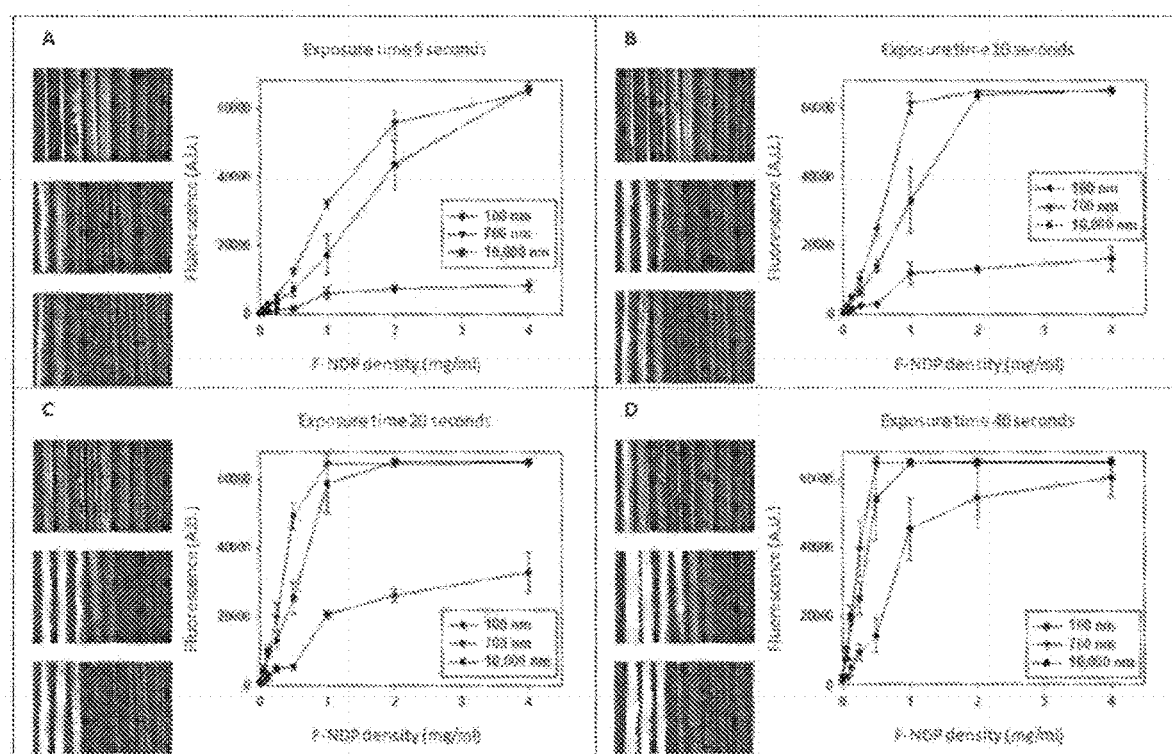
FIGS. 27A-27D show a comparison of intensity of fluorescence of different sizes of F-NDP(NV) under different exposure times in IVIS. Left panes shows representative images of F-NDP(NV), presented in concentrations as pointed on the plot. Sizes of particles are (from the top): 100, 700, and 10,000 nm, respectively. Error bars represent SD for three independent experiments.

Comparison of NIR fluorescence intensity of F-NDP (NVN) and F-NDP(NV) fluorescence profile measurements revealed NIR fluorescence in both N-V and N-V-N particles. However, fluorescence in the NIR region was 20 times greater in the N-V particles (FIG. 26A). This experiment also revealed the peak excitation of F-NDP(NV) at 570 nm and peak emission at 670 nm. Using this peak excitation and emission profile, NIR emission of the F-NDPs was compared in the IVIS in a dose response manner (FIG. 26B, FIG. 26C). Capillary studies revealed that under the same excitation conditions, NIR emission of the F-NDP(NV) was more effective than that of F-NDP(NVN) by approximately an order of magnitude (FIG. 26B).

Figures 28A, 28B, 28C, 28D, 28E, 28F, 28G, 28H:
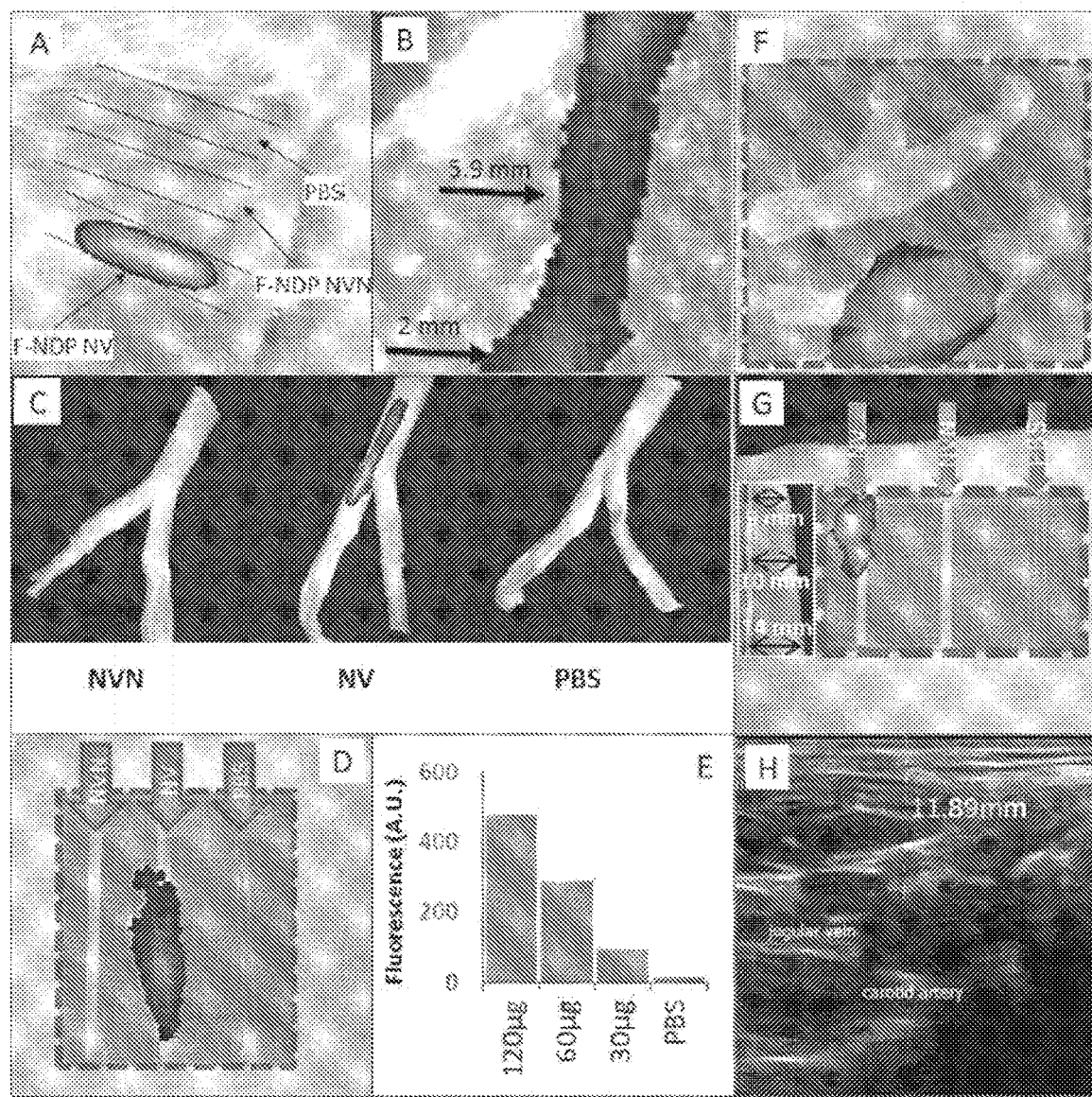
FIGS. 28A-28H show a comparison of the ability to detect F-NDP NIR fluorescence through different biological barriers using IVIS.

Fluorescent characteristics of F-NDP may vary with size of particle. The NIR emission of identical mass per mL of F-NDP(NV) was compared for particles of three different sizes (FIGS. 27A-27D). The lowest fluorescence intensity was observed for smallest (100 nm) particles, while the highest fluorescence emission was observed for 700 nm F-NDP. Fluorescence scaled linearly with exposure time revealing no bleaching at the higher exposure times tested. While fluorescence from the 700 nm F-NDP(NV) particles saturated the detector in less than 20 seconds, longer exposure times were required to clearly display fluorescence from the F-NDP(NVN) particles. It is noteworthy that for the same acquisition time the NIR emission of 700 nm and 10,000 nm was not augmented. In fact, at 0.5 mg/ml and 1 mg/ml, the emission of the 10,000 nm particles, was significantly lower than that of the 700 nm particles ($p<0.01$, FIG. 27A). We then tested the ability of NIR fluorescence emitted from equivalent sized (700 nm) F-NDP particles of the N-V and N-V-N strains of F-NDP to penetrate biological barriers as imaged in the IVIS (FIGS. 28A-28H). Capillaries filled with 4 mg/ml F-NDP(NV) particles could be imaged through rat skin (FIG. 28A) or quadriceps muscle (FIG. 28B) as well as porcine axillary vein (FIG. 28C) and 2.5 mm of defatted porcine skin (FIG. 28D), while capillaries filled with F-NDP(NVN) particles could not be visualized with similar imaging parameters in any of these circumstances. NIR fluorescence was monitored through 2.5 mm of defatted porcine skin at concentrations from 1-4 mg/ml (30-120 micrograms total) (FIG. 28E) as the signal did not penetrate full-thickness tissue. Porcine axillary veins loaded with 1 mL of 2 mg/mL of F-NDP(NV) particles could be visualized through 8 mm of porcine skin (FIG. 28F). As a final test of penetration capacity, an angled piece of full thickness porcine skin varying from 9 to 14 mm in thickness was laid on top of capillaries containing 20 mg/mL (600 µg total) of F-NDP(NV). A detectable signal from the F-NDP(NV) was recorded through the porcine skin up 12 mm in thickness. In contrast, no light emission was detected at equal conditions of F-NDP(NVN) (FIG. 28G). Noteworthy is data obtained by ultrasound imaging of human carotid arteries, where the carotid artery bifurcation distance from the skin surface was assessed at 14 mm below the skin surface. These findings suggest a translational prospect of F-NDP(NV) to detect blood clot in this area if comparable particle mass can be safely deposited on a blood clot in this region (FIG. 28H).

Detection of Blood Clot in Rat Model Using F-NDP(NV)-Bit

Figures 29A, 29N:
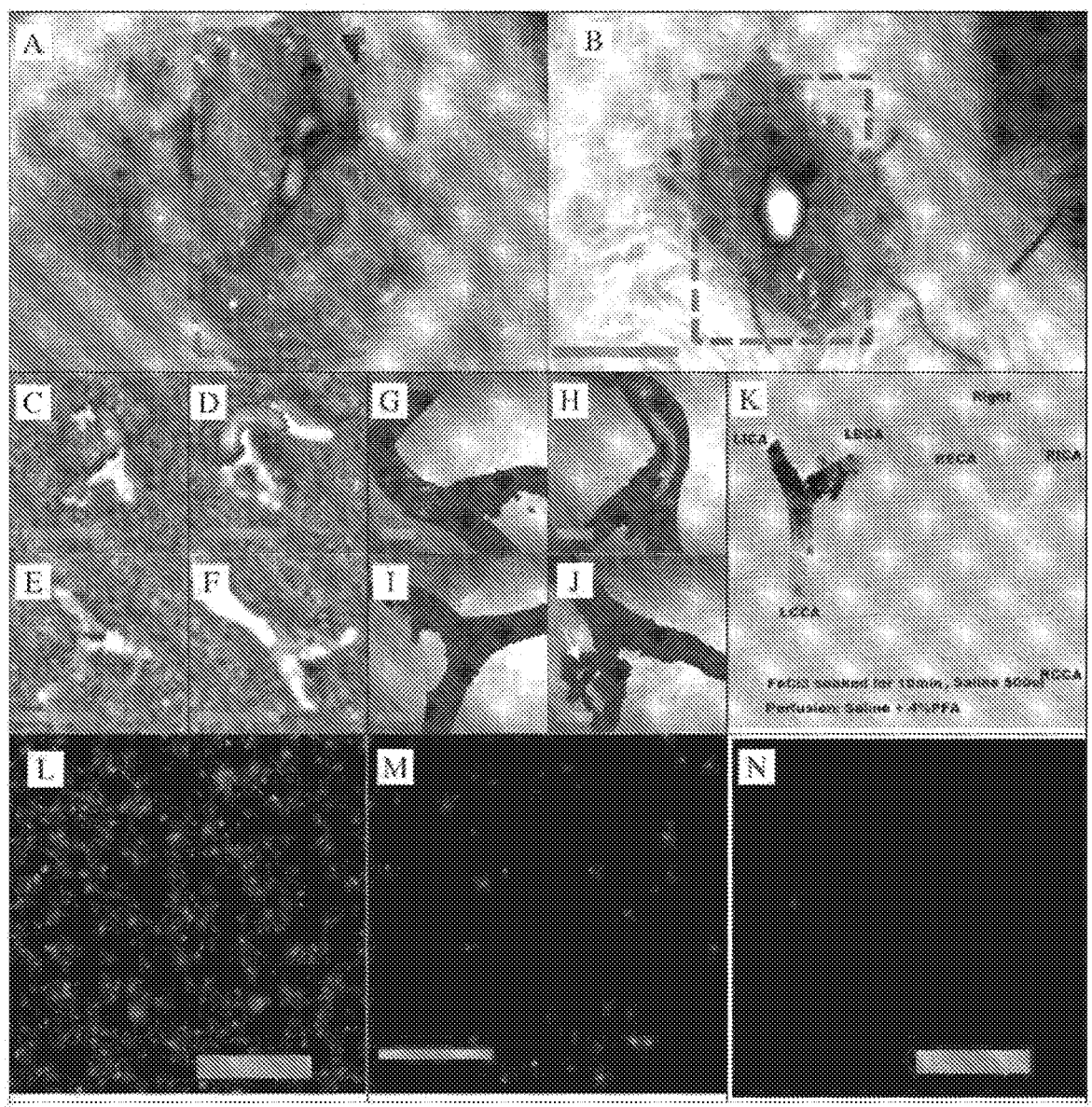
FIGS. 29A-29N show F-NDP(NV)-Bit infusion via external carotid artery. Carotid arteries clots are imaged in situ and removed from the animal for further direct imaging and analysis.

The results depicted in FIGS. 26A-28H suggest that F-NDP(NV) (700 nm) are the brightest of the particles tested and may be a useful F-NDP strain for imaging in vivo. Therefore, all subsequent in vivo studies were carried out with F-NDP(NV) coupled with Bit for detection of thrombi generated in the carotid artery bifurcation of rats. After clot formation and treatment with F-NDP(NV)-Bit via the ECA, carotid arteries were imaged in situ and removed from the animal for imaging and analysis. Injection of F-NDP via the ECA optimizes the exposure of the particles to the lesion site thus avoiding potentially confounding variables of distribution, uptake, and elimination. Imaging of fluorescence in the IVIS scanner demonstrated strong fluorescence in situ (FIG. 29A, FIG. 29B) in the vessel branches corresponding to the location of the clot in the exposed artery. After removing the carotid arterial bifurcations from treated and untreated animals, a strong fluorescent signal is detected (FIG. 29C, FIG. 29D vs FIG. 29E, FIG. 29F) in the $FeCl_3$-treated arteries. This was further validated by confocal imaging confirming co-location of clot and deposited particles (FIG. 29G, FIG. 29H vs FIG. 29I, FIG. 29J). As a final validation method, particles were imaged in pooled lysates (2 lesions), showing large numbers of fluorescence particles in F-NDP(NV—treated animals as compared to their absence in animals treated with vehicle (FIG. 29K). Following in the initial proof of feasibility direct administration of the F-NDP(NV)-Bit via ECA, a low (3 mg/Kg) and high (15 mg/kg) dose of F-NDP(NV)-Bit were infused systemically into animals via the femoral vein. The results from animals treated with the low dose were inconclusive, as the signal was not consistently above the fluorescence level detected from carotid bifurcation isolated from control animals treated with vehicle only. Despite this, pooled lysates (3 lesions) showed that F-NDP particles had been logged in the clots, while no particle associated fluorescence was detectable from vehicle treated animals (FIG. 29L).

Figures 30A, 30S:
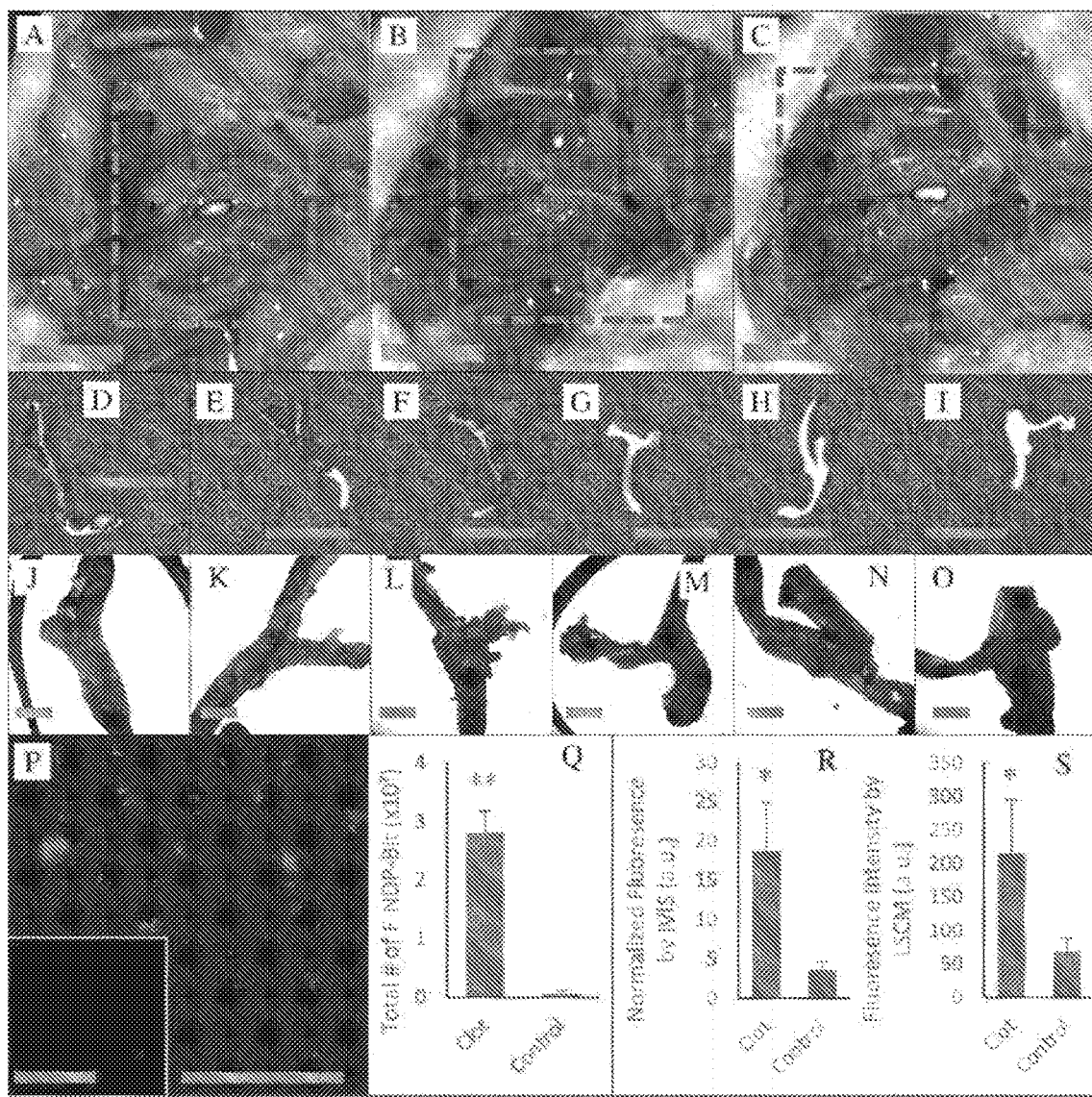
FIGS. 30A-30S shows F-NDP(NV)-Bit intravenous infusion.

After IV injection of the high dose of F-NDP(NV)-Bit, clot-associated fluorescence was demonstrated in situ in all treated animals (FIGS. 30A-30C). Arteries with $FeCl_3$- generated lesions and the contralateral control were then dissected and imaged independently by IVIS and confocal microscopy. A strong fluorescence signal in the treated artery was observed by both IVIS (FIGS. 30D-30F vs FIGS. 30G-30I) and confocal imaging (FIGS. 30J-30L vs FIGS. 30M-30O). The difference in brightness to that of the control artery was statistically significant (FIG. 30R, FIG. 30S) with p<0.05. Lysates collected by dissolving the carotid arteries also demonstrated a large number of fluorescent particles residing in the lesioned artery and a low, but consistent, number of particles in the contralateral control arteries (FIG. 30P). This difference was highly statistically significant (FIG. 30Q) with p<0.01.

The two main objectives of the example described above were 1) characterization of the two strains of the F-NDP (F-NDP(NV) and F-NDP(NVN)) in terms of their NIR emission parameters and 2) identification of the F-NDP strain, which emits sufficient energy that most likely penetrates biological tissues over a distance required for the translational application in human NIR vascular pathology imaging. Given the prospect of longer (minutes) scale of imaging procedures in humans an important consideration in selection F-NDP includes the stability/durability of the NIR emission. Nanoparticles in general tend to have reduced toxicity with increased diameter. Specifically, nanodiamonds display reduced toxicity (as compared to e.g. nanotubes) with increasing diameter (tested up to 100 nm), suggesting that the 700 nm F-NDP(NV) used in this study may be safe. Preliminary studies suggest no mortality or morbidity in rats injected via venous port, with 700 nm F-NDP(NV) at 45 mg/kg while evaluated for weight and neurobehavioral tests for up to 5 days.

The first objective was to systematically investigate the emission attributes each of F-NDP across four independent variables: a) the fluorescence spectrum and brightness resulting from the atomic manipulations (N-V, N-V-N); b) particles total mass relationships to emission intensity; c) the relationship of particle diameter to emission intensity and d) speed and extent of NIR acquisition kinetics. These variables have been exercised 'head to head' between N-V and N-V-N strains using IVIS technology, which were considered all well suited for such comparison in due to its sensitivity and its non-invasive NIR light detection capability. The data presented in FIGS. 26A-27D point to the prospect of the F-NDP(NV) strain as useful for in vivo NIR fluorescent penetration through biological tissues. For example, in this example the 700 nm F-NDP(NV) exhibited 10-60 higher NIR emission intensity than the F-NDP(NVN). Of note, NIR emission from F-NDP(NV) was not directly correlated with particle size, and was maximized for 700 nm F-NDP(NV). At constant particle mass loading, the 700 nm particles were ~4 times brighter in IVIS images, and consistently and across all acquisition periods tested; NIR fluorescence emission from 10,000 nm particles was weaker than from e 700 nm particles (FIG. 2). While 10,000 nm F-NDP(NV) may be not likely to be useable for IV injection, the 10,000 nm particles demonstrated that under equal mass conditions particle brightness was not correlated with diameter, but may be maximized for particles of a specific diameter range.

Commensurate with the physical properties delineated for the F-NDP(NV) (FIGS. 26A-27D) the data in FIGS. 28A-28H further support the potential of the F-NDP(NV) to support in vivo vascular clot imaging. FIG. 3 presents several conditions where tissues penetration of NIR fluorescence emitted from F-NDP(NV) was tested. The maximum distance detectable by NIR through porcine skin, used as a human skin analog, (FIG. 28G) was 12 mm. FIG. 28H presents an ultrasound recording of normal human carotid artery bifurcation annotated for the ICA, ECA and CCA. The linear dashed bar in FIG. 28H indicates 11.89 mm depth of the human carotid artery bifurcation from the vertical distance from the neck surface. Considering the dense epidermis of porcine shoulder skin as compared to human neck and the distance of the IVIS camera from the target to be monitored versus the use of a similar hand-held device placed directly on the skin, it is posited that NIR fluorescent imaging of a clot bin the carotid artery bifurcation is likely to be within an achievable diagnostic opportunity. Furthermore, NIR fluorescence recorded in FIG. 28H represents a source generated from ~670 ug of 700 nm F-NDP(NV) particles. The same amount of particles tagged onto human clot in this region could enable clot detection by NIR fluorescence imaging. Results in FIG. 30Q indicates a minimum of 0.7% of injected dose was captured in the lesion of interest ($2 \times 10^8$ particles/mg in dose), which would imply a required dose of approximately 100 mg (1.4 mg/kg) to reach a similar emission profile in human. In preliminary studies in rat, doses as high as 45 mg/kg were well tolerated for 5 days without any adverse events recorded (data not shown).

In vivo studies were performed with an F-NDP(NV)-Bit covalently coupled with bitistatin. The procedure used EDC-mediated covalent heterobifunctional coupling, yielding a stable amide bond, which is resilient in biological systems. These F-NDP(NV)-Bit, were administered systemically to anesthetized rats subjected to an established carotid artery clot procedure at the site of the bifurcation. In the pilot translational study F-NDP(NV)-Bit were first administered via the ECA ('high dose', 15 mg/Kg) or via the femoral artery ('low dose', 3 mg/Kg). This experimental design was selected since pharmacokinetics and particles distribution dynamics are as yet unknown. Therefore, to avoid possible loss of significant amount of particles via 'first path' elimination or tissue distribution (potential 'false negative' outcome), injection via the ECA ascertains maximum exposure of the particles to the clot in the targeted region. To assess and confirm specific co-localization of F-NDP(NV)-Bit in the blood three independent methods were deployed: a) IVIS total body imaging (FIG. 29A, FIG. 29B); b) LSCM of extracted vessels carrying clots (FIG. 29C, FIG. 29D) and c) direct count of particles extracted from clot-bearing vessels after solubilization of all organic material (FIG. 29L). Association of F-NDP(NV) by infusion of a high dose of F-NDP (NV)-Bit via the ECA is easily detected by all three methods. However, infusion of a low dose (3 mg/Kg) of F-NDP (NV)-Bit via the femoral vein failed to detect emission by either IVIS or by LSCM (FIG. 4E-F). A low amount of particles was counted in the clot extract (FIG. 29M), yet it is not clear whether this very small number is specifically clot associated, loaded into the vessel wall via "vasa-vasorum" or both. It is clear however that the low dose of F-NDP(NV)-Bit did not produce a credible emission signal that could be detected by IVIS or LSCM, even if particles were in fact target to the clot. Next, F-NDP(NV)-Bit was intravenously administered at a higher dose (15 mg/Kg, N=3). As illustrated in FIGS. 30A-30C, all three animal tested displayed a strong fluorescence signal emanating from the carotid bifurcation zone (IVIS), as also clearly visible in the fluorescence of isolated vessels (FIGS. 30D-30I) and under inspection by LSCM (FIGS. 30J-30O). Particles were also present in large numbers in solubilized clot-bearing vessels (FIG. 30P). FIGS. 30Q-30S show the quantitative analysis of the robust deposition of particles in clot-bearing vessels vs. the control contralateral.

In summary in this example evidence was demonstrated that the F-NDP(NV) deployed in this study can associate with clot in vivo, such as a thrombus formed in a rat carotid artery bifurcation model. The proof-of-concept here is based on three independent measures or the NIR fluorescence detected at the in situ clot formation, including direct counting of fluorescence particles isolated from the extracted clot. The data demonstrates the possibility to detect by NIR fluorescence imaging emitted from F-NDP (NV) over a distance corresponding to that present in vascular pathology (e.g. clot in the carotid artery bifurcation). If successfully translated to clinical practice, this minimally invasive procedure, conducted in ambulatory settings, could enhance preventative measures, such as earlier initiation of anti-thromboembolic medications.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A fluidic device, comprising:
   a sample inlet;
   a reservoir in fluidic communication with the sample inlet, the reservoir comprising a plurality of fluorescent nanodiamond particles;
   a plurality of a first species bound to the plurality of fluorescent nanodiamond particles; and
   a detection region in fluidic communication with the reservoir, the detection region comprising a plurality of a second species bound to the detection region,
   wherein the first species is a disintegrin.

2. A fluidic device as in claim 1, further comprising a control region in fluidic communication with the detection region, the control region comprising a plurality of a third species bound to the control region.

3. A fluidic device as in claim 1, wherein the plurality of first species and the plurality of second species are each configured to bind to an analyte.

4. A fluidic device as in claim 2, wherein in the third species is capable of binding to the first species.

5. A fluidic device as in claim 1, wherein the fluorescent nanodiamond particles have an emission wavelength of greater than or equal to 250 nm and less than or equal to 1000 nm.

6. A fluidic device as in claim 1, further comprising an absorbent region in fluidic communication with the control region.

7. A fluidic device as in claim 1, wherein the disintegrin is selected from the group consisting of albolabrin, applagin, barbourin, batroxostatin, bitistatin, obtustatin, schistatin, echistatin, elegantin, eristicophin, flavoridin, halysin, kistrin, mojastin, rubistatin, tergeminin, salmosin and triflavin.

8. A fluidic device as in claim 1, wherein the first species is covalently bound to the plurality of fluorescent nanodiamond particles.

9. A fluidic device as in claim 1, wherein the plurality of fluorescent nanodiamond particles comprise an atomistic-type defect.

10. A fluidic device as in claim 9, wherein the atomistic-type defect is a nitrogen-vacancy defect, a nitrogen-vacancy-nitrogen defect, or an Si-vacancy defect.

11. A fluidic device as in claim 1, wherein the plurality of fluorescent nanodiamond particles is fluorescent as a result of an intrinsic property of the nanodiamond particle.

* * * * *